(12) United States Patent
Hansen et al.

(10) Patent No.: US 8,992,937 B2
(45) Date of Patent: Mar. 31, 2015

(54) DISULFIDE TRAP MHC CLASS I MOLECULES AND USES THEREFOR

(75) Inventors: Ted H. Hansen, North Potomac, MD (US); Daved Fremont, Saint Louis, MO (US); Janet Connolly, North Potomac, MD (US); Lonnie Lybarger, Tucson, AZ (US); Michael Miley, Cary, NC (US); Vesselin Mitaksov, Ballwin, MO (US); Steven Truscott, Royal Oak, MI (US)

(73) Assignee: Washington University, Saint Louis, MO (US)

( * ) Notice: Subject to any disclaimer, the term of this patent is extended or adjusted under 35 U.S.C. 154(b) by 1655 days.

(21) Appl. No.: 11/846,491

(22) Filed: Aug. 28, 2007

(65) Prior Publication Data

US 2009/0117153 A1    May 7, 2009

Related U.S. Application Data

(60) Provisional application No. 60/840,521, filed on Aug. 28, 2006.

(51) Int. Cl.
*A61K 39/00* (2006.01)
*A61K 39/385* (2006.01)
*C07K 7/06* (2006.01)
*C07K 14/74* (2006.01)
*C07K 14/00* (2006.01)

(52) U.S. Cl.
CPC ......... *A61K 39/385* (2013.01); *A61K 2039/605* (2013.01); *C07K 7/06* (2013.01); *C07K 14/70539* (2013.01); *C07K 2319/00* (2013.01)
USPC ...................... 424/192.1; 424/193.1; 530/350

(58) Field of Classification Search
None
See application file for complete search history.

(56) References Cited

U.S. PATENT DOCUMENTS

2003/0166277 A1 * 9/2003 Zauderer et al. .............. 435/372

OTHER PUBLICATIONS

Engelhard (Curr. Opin. Immunol. 1994, 6: 13-23).*
Guo, et al (Nature, 1992 360: 364-366).*
Truscott et al (J. Immunol. 2007, 178: 6280-6289).*
Mitaksov et al (Chemistry & Biology, 2007, 14: 909-922).*
Truscott et al (J. Biol. Chem. 2008, 283(12): 7480-7490).*
Trowsdale and Campbell (Cur. Prot. Immunol. 1998, A.1K.1-A.1K.14, Supplement 27, John Wiley & Sons, Inc.).*
Olsen et al (Inf. Immun. 1998, 66(3): 944-949).*
UniProt Accession No. Q95460, 2014.*
Altamirano et al, Ligand-independent assembly of recombinant human CD1 by using oxidative refolding chromatography, PNAS, 2001, 98:3288-3293.
Balendiran et al, The three-dimensional structure of an H-2Ld-peptide complex explains the unique interaction of Ld with beta-2 microglobulin and peptide, PNAS, 1997, 94:6880-6885.
Beck et al, Slower processing, weaker beta 2-M association, and lower surface expression of H-2Ld are influenced by its amino terminus, J Immunol, 1986, 137:916-923.
Connolly, The peptide p2Ca is immunodominant in allorecognition of Ld by beta chain variable region V beta 8+ but not V beta 8-strains, PNAS, 1994, 91:11482-11486.
Connolly, Solvent-accessible surfaces of proteins and nucleic acids, Science, 1983, 221:709-713.
Cresswell et al, Thiol oxidation and reduction in MHC-restricted antigen processing and presentation, Immunol Res, 1991, 19:191-200.
Fremont et al, Crystal structure of an H-2Kb-ovalbumin peptide complex reveals the interplay of primary and secondary anchor positions in the major histocompatibility complex binding groove. PNAS, 1995, 92:2479-2483.
Fremont et al, Structures of an MHC class II molecule with covalently bound single peptides, Science, 1996, 272:1001-1004.
Holler et al, In vitro evolution of a T cell receptor with high affinity for peptide/MHC, PNAS, 2000, 97:5387-5392.
Huang et al, Cancer immunotherapy using a DNA vaccine encoding a single-chain trimer of MHC class I linked to an HPV-16 E6 immunodominant CTL epitope, Gene Ther, 2005, 12:1180-1186.
Jaramillo et al, Recognition of HLA-A2-restricted mammaglobin-A-derived epitopes by CD8+ cytotoxic T lymphocytes from breast cancer patients, Breast Cancer Res Treat, 2004, 88:29-41.
Kersh et al, Structural and functional consequences of altering a peptide MHC anchor residue, J Immunol, 2001, 166:3345-3354.
Lie et al, Peptide ligand-induced conformation and surface expression of the Ld class I MHC molecule, Nature, 1990, 344:439-441.
Lie et al, The specific binding of peptide ligand to Ld class I major histocompatibility complex molecules determines their antigenic structure, J Exp Med, 1991, 173:449-459.
Lybarger et al, Virus subversion of the MHC class I peptide-loading complex, Immunity, 2003, 18:121-130.
Lybarger et al, Enhanced immune presentation of a single-chain major histocompatibility complex class I molecule engineered to optimize linkage of a C-terminally extended peptide, J Biol Chem, 2003, 278:27105-27111.
Matsumura et al, Emerging principles for the recognition of peptide antigens by MHC class I molecules, Science, 1992, 257: 927-934.

(Continued)

*Primary Examiner* — Michael Szperka
*Assistant Examiner* — Marianne Dibrino
(74) *Attorney, Agent, or Firm* — Zackson Law LLC; Saul L. Zackson

(57) ABSTRACT

A disulfide trap, comprising an antigen peptide covalently attached to an MHC class I heavy chain molecule by a disulfide bond extending between two cysteines, is disclosed. In some configurations, a disulfide trap, such as a disulfide trap single chain trimer (dtSCT), can comprise a single contiguous polypeptide chain. Upon synthesis in a cell, a disulfide trap oxidizes properly in the ER, and can be recognized by T cells. In some configurations, a peptide moiety of a disulfide trap is not displaced by high-affinity competitor peptides, even if the peptide binds the heavy chain relatively weakly. In various configurations, a disulfide trap can be used for vaccination, to elicit CD8 T cells, and in multivalent MHC/peptide reagents for the enumeration and tracking of T cells. Also disclosed are nucleic acids comprising a sequence encoding a disulfide trap. Such nucleic acids, which can be DNA vectors, can be used as vaccines.

22 Claims, 49 Drawing Sheets

(56) References Cited

OTHER PUBLICATIONS

Miley et al, Structural basis for the restoration of TCR recognition of an MHC allelic variant by peptide secondary anchor substitution, J Exp Med, 2004, 200:1445-1454.

Mitaksov et al, Structural definition of the H-2Kd peptide-binding motif, J Biol Chem, 2006, 281:10618-10625.

Myers et al, Kb, Kd, and Ld molecules share common tapasin dependencies as determined using a novel epitope tag, J Immunol, 2000, 165:5656-5663.

Primeau et al, Applications of major histocompatibility complex class I molecules expressed as single chains, Immunol Res, 2005, 32:109-121.

Wang et al, Requirements for the selective degradation of endoplasmic reticulum-resident major histocompatibility complex class I proteins by the viral immune evasion molecule mK3, J Virol, 2005, 79:4099-4108.

Wilson and Fremont, Structural analysis of MHC class I molecules with bound peptide antigens, Semin Immunol, 1993, 5:75-80.

Yu et al, Cutting edge: single-chain trimers of MHC class I molecules form stable structures that potently stimulate antigen-specific T cells and B cells, J Immunol, 2002, 168:3145-3149.

* cited by examiner

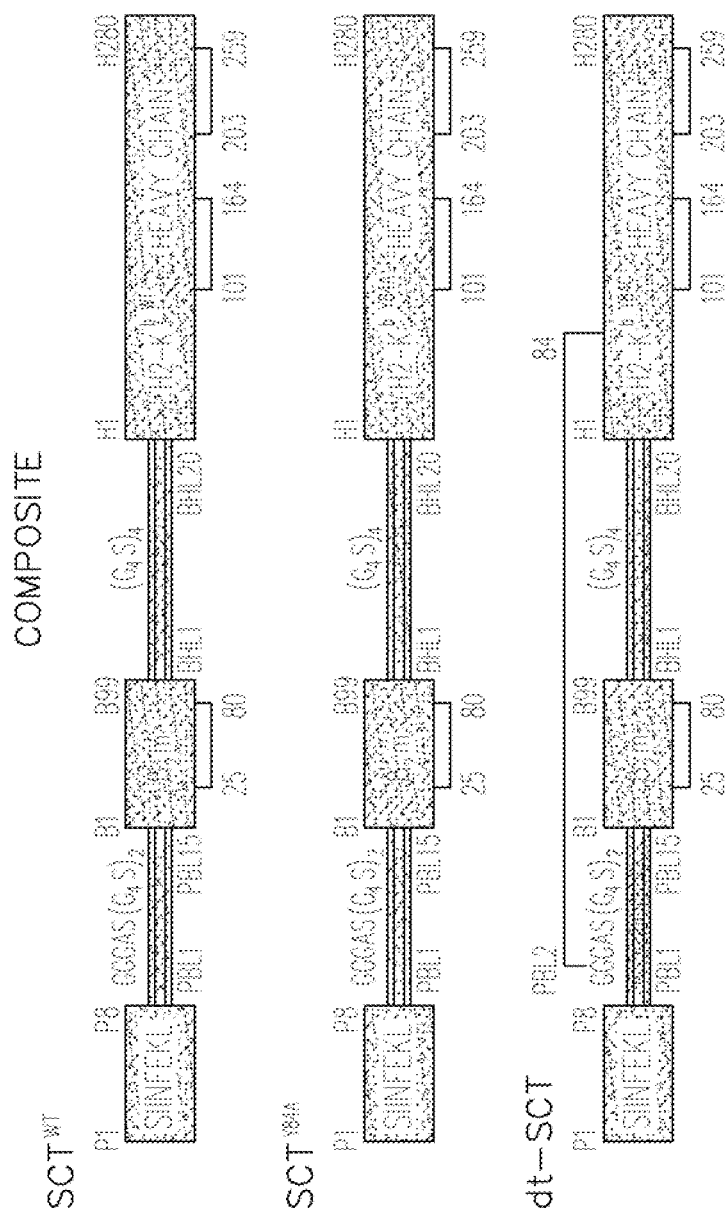

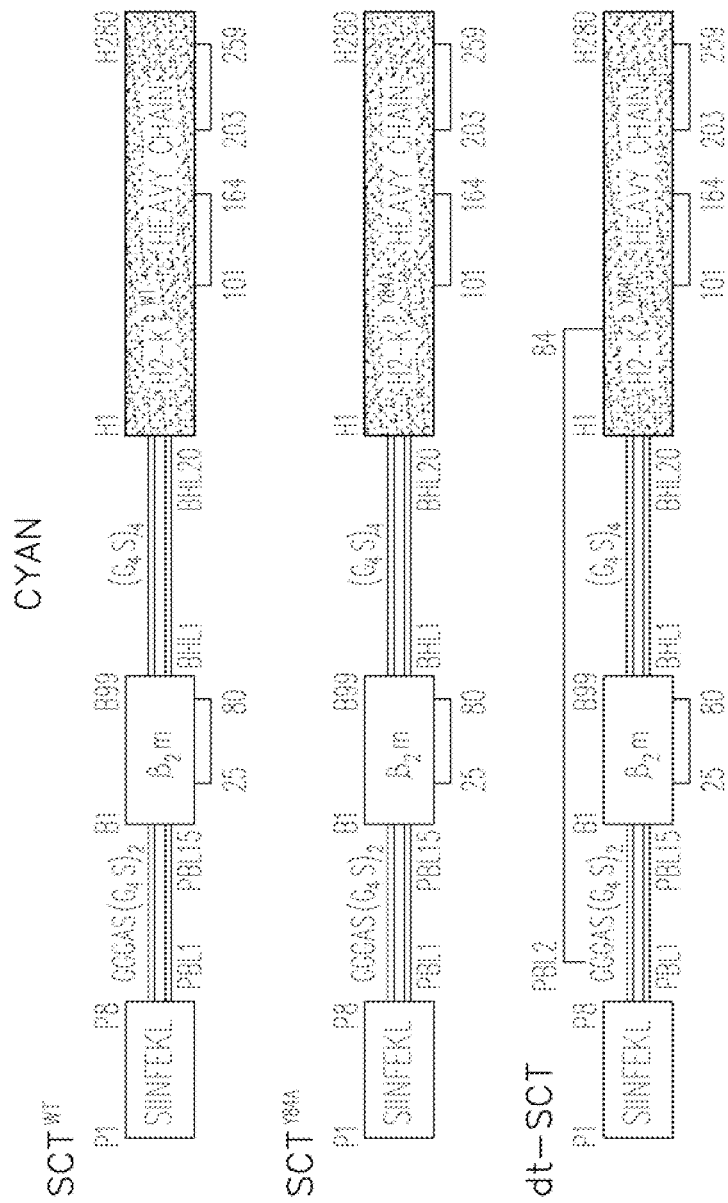

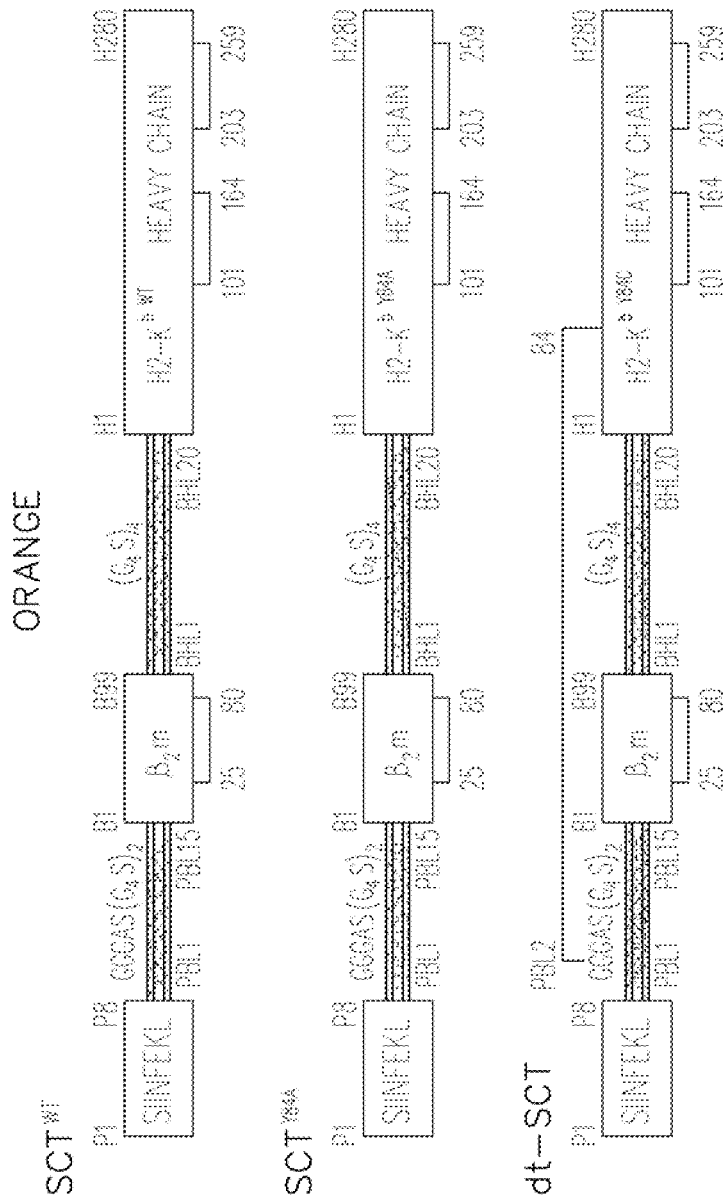

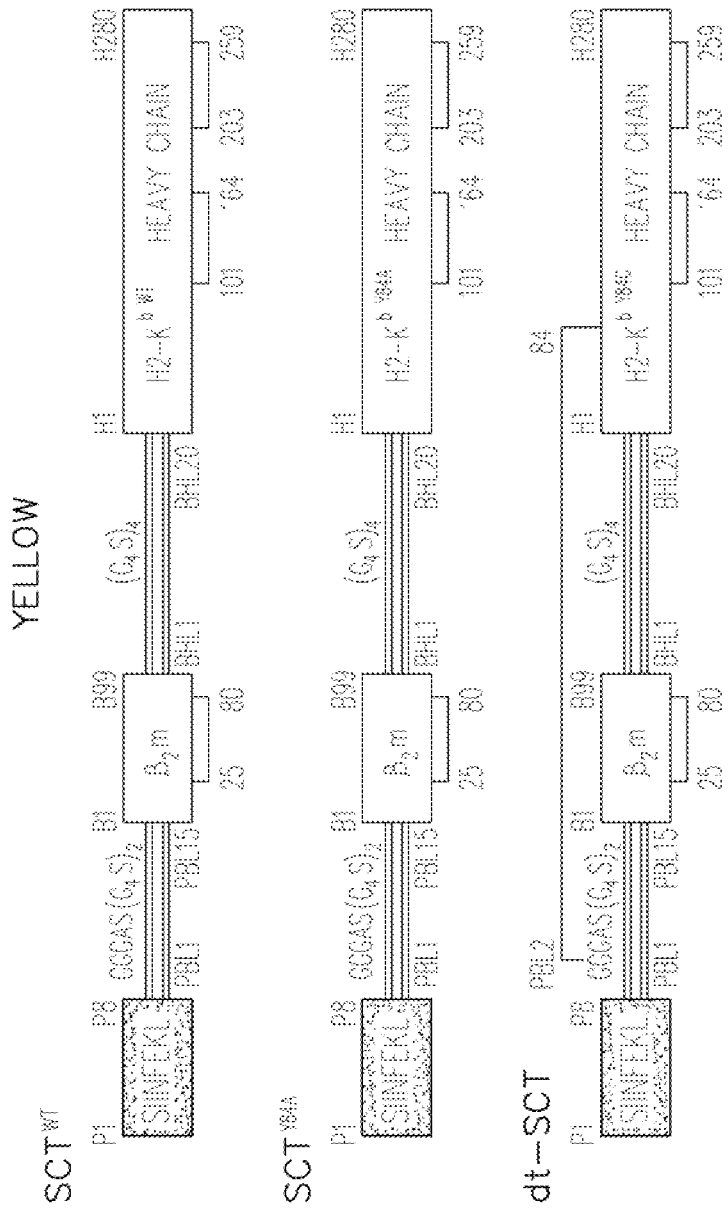

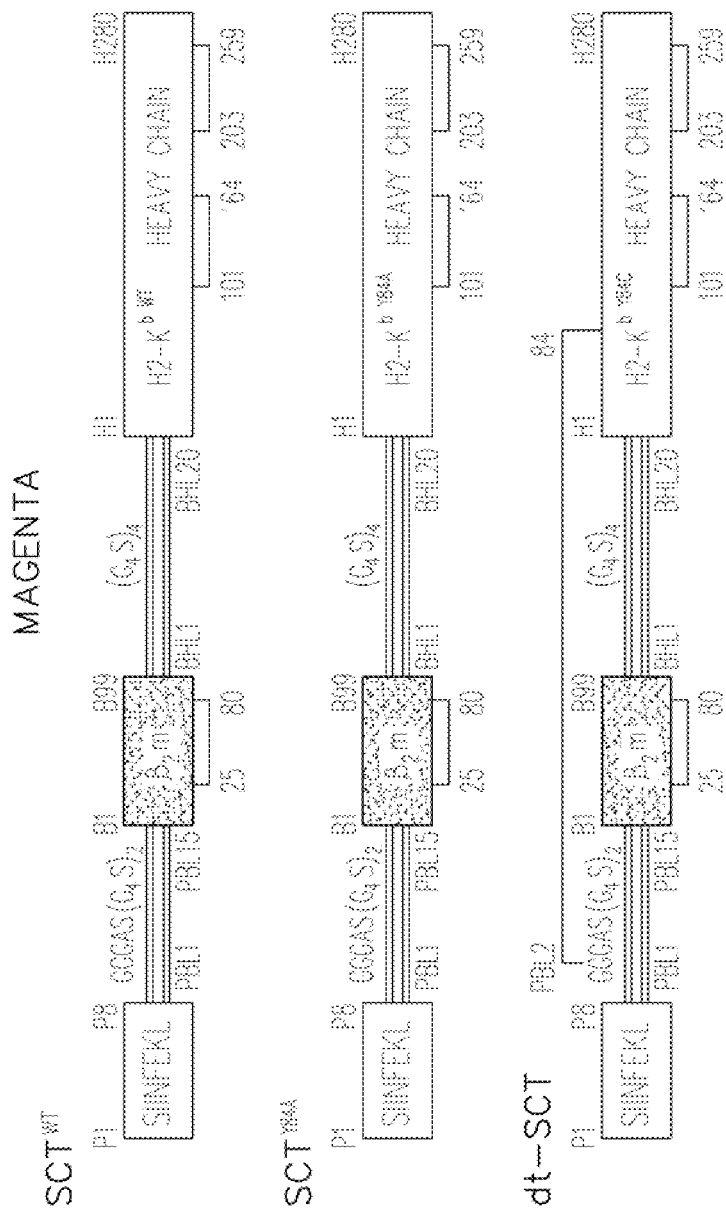

COMPOSITE

YELLOW

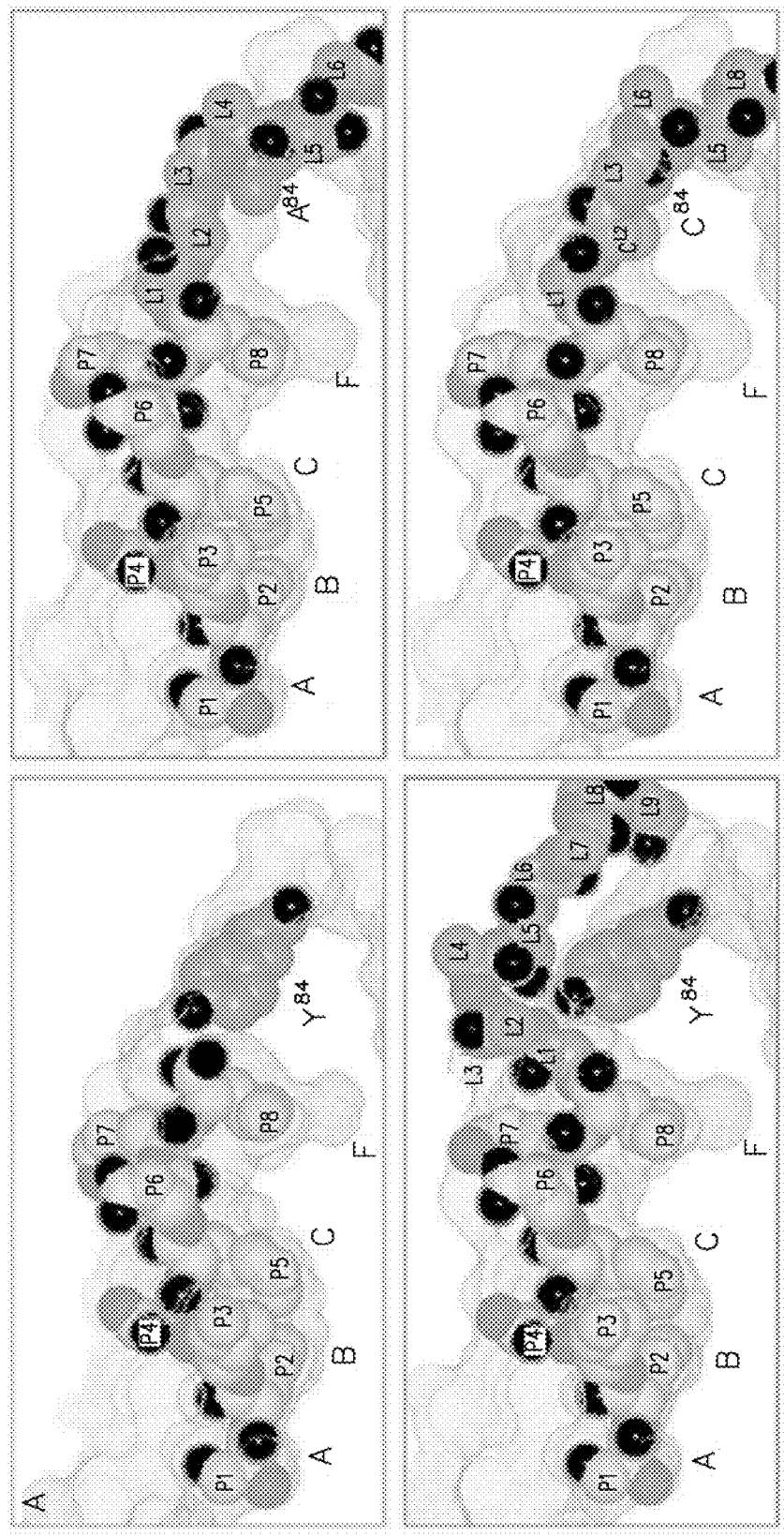
FIG. 9C RED

DARK BLUE

ORANGE

LIGHT BLUE

GREEN

PURPLE

SILVER / GRAY

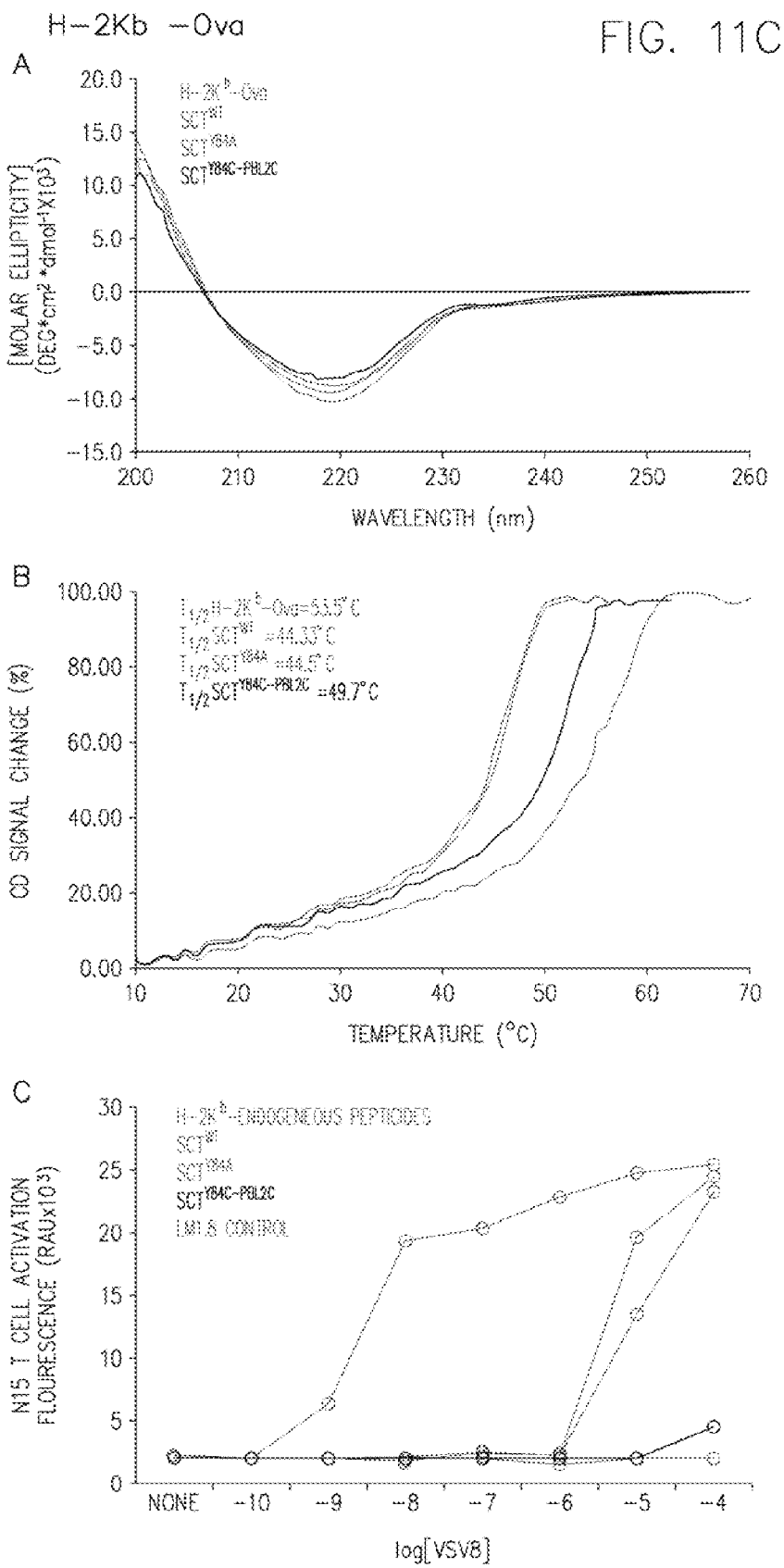

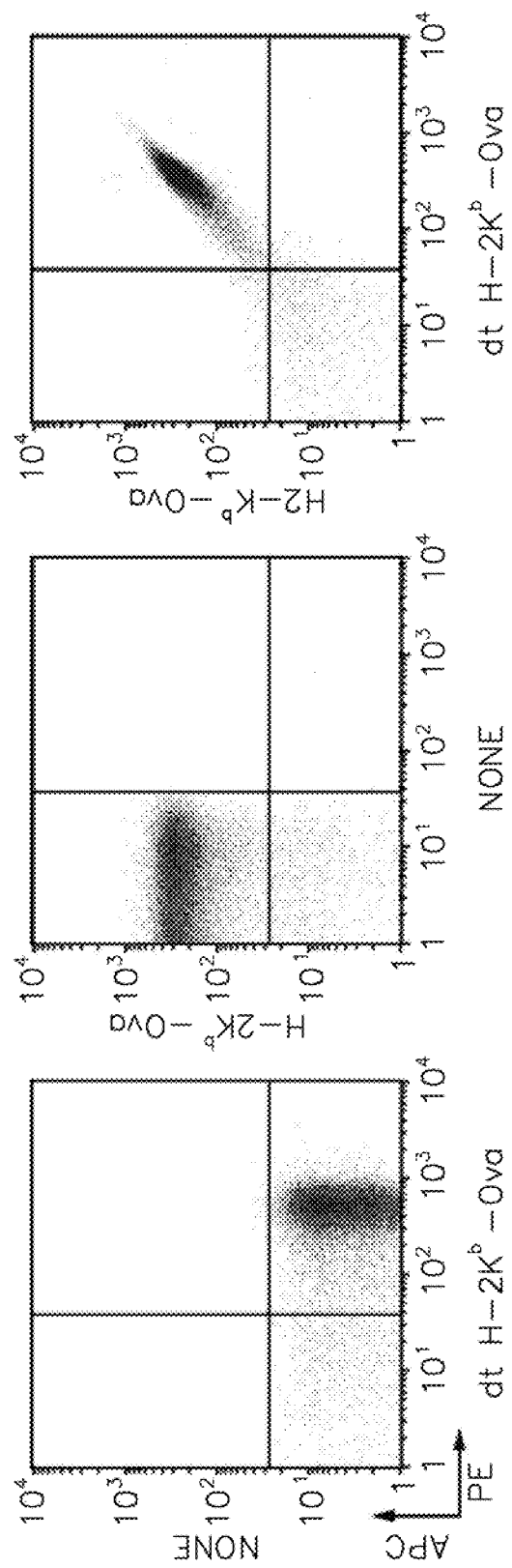

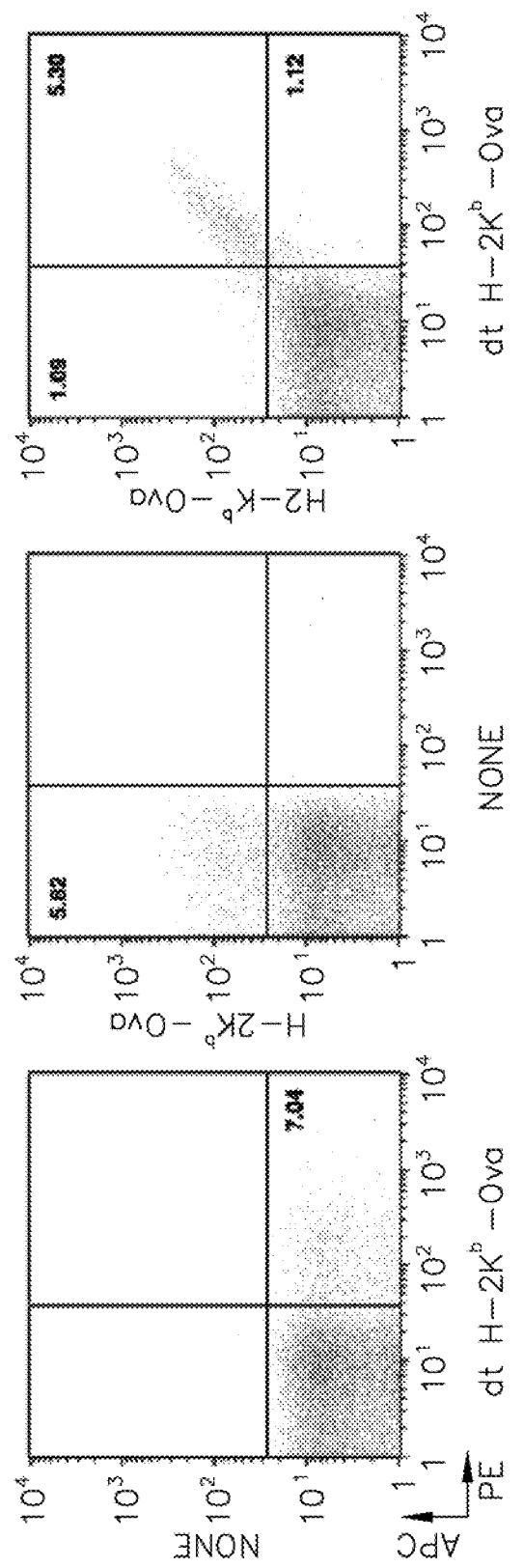

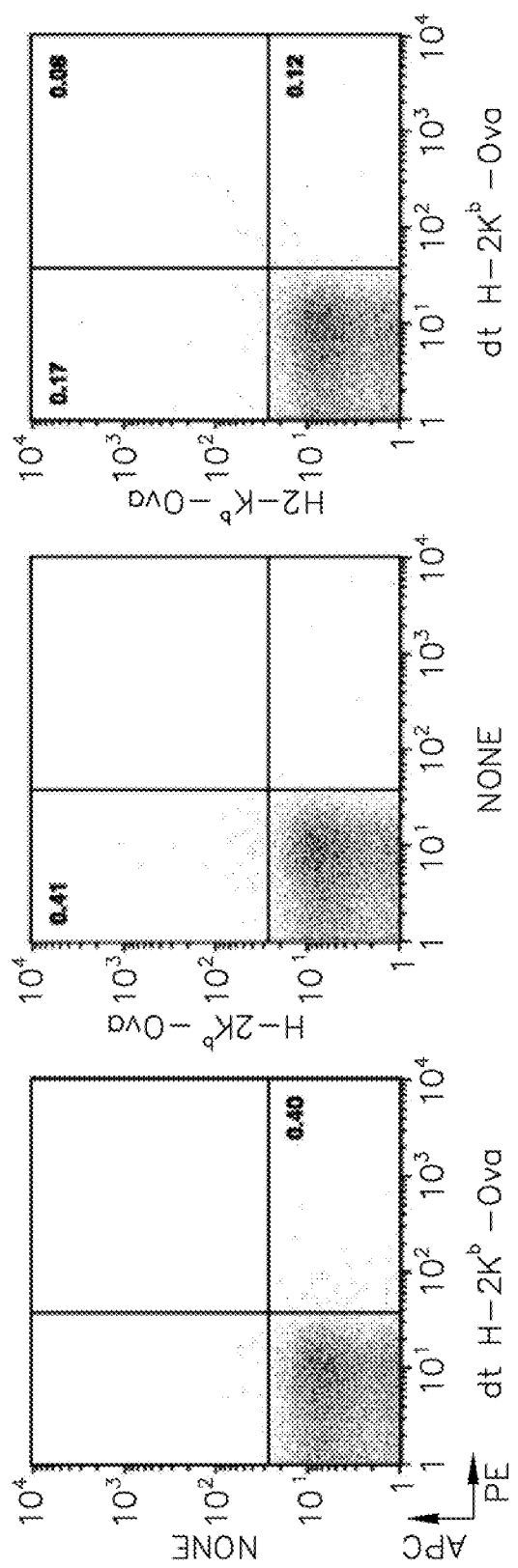

SEQUENCE LISTING

<160> NUMBER OF SEQ ID NOS: 38

<210> SEQ ID NO 1
<211> LENGTH: 9
<212> TYPE: PRT
<213> ORGANISM: cytomegalovirus

<400> SEQUENCE: 1

Asn Leu Val Pro Met Val Ala Thr Val
1               5

<210> SEQ ID NO 2
<211> LENGTH: 9
<212> TYPE: PRT
<213> ORGANISM: Epstein-Barr Virus

<400> SEQUENCE: 2

Gly Leu Cys Thr Leu Val Ala Met Leu
1               5

<210> SEQ ID NO 3
<211> LENGTH: 9
<212> TYPE: PRT
<213> ORGANISM: Influenza A virus

<400> SEQUENCE: 3

Gly Ile Leu Gly Phe Val Phe Thr Leu
1               5

<210> SEQ ID NO 4
<211> LENGTH: 9
<212> TYPE: PRT
<213> ORGANISM: homo sapiens

<400> SEQUENCE: 4

Ile Met Asp Gln Val Pro Phe Ser Val
1               5

```
<210> SEQ ID NO 5
<211> LENGTH: 9
<212> TYPE: PRT
<213> ORGANISM: homo sapiens

<400> SEQUENCE: 5

Tyr Leu Glu Pro Gly Pro Val Thr Val
1               5

<210> SEQ ID NO 6
<211> LENGTH: 9
<212> TYPE: PRT
<213> ORGANISM: HTLV

<400> SEQUENCE: 6

Leu Leu Phe Gly Tyr Pro Val Tyr Val
1               5

<210> SEQ ID NO 7
<211> LENGTH: 10
<212> TYPE: PRT
<213> ORGANISM: homo sapiens

<400> SEQUENCE: 7

Leu Ile Tyr Asp Ser Ser Leu Cys Asp Leu
1               5                   10

<210> SEQ ID NO 8
<211> LENGTH: 10
<212> TYPE: PRT
<213> ORGANISM: Hepatitis B virus

<400> SEQUENCE: 8

Phe Leu Pro Ser Asp Phe Phe Pro Ser Val
1               5                   10

<210> SEQ ID NO 9
<211> LENGTH: 9
<212> TYPE: PRT
<213> ORGANISM: Hepatitis B virus

<400> SEQUENCE: 9

Cys Leu Thr Phe Gly Arg Glu Thr Val
1               5

<210> SEQ ID NO 10
<211> LENGTH: 9
<212> TYPE: PRT
<213> ORGANISM: HIV

<400> SEQUENCE: 10

Ser Leu Tyr Asn Thr Val Ala Thr Leu
1               5

<210> SEQ ID NO 11
<211> LENGTH: 10
<212> TYPE: PRT
<213> ORGANISM: homo sapiens

<400> SEQUENCE: 11

Lys Leu Leu Gly Pro His Val Glu Gly Leu
1               5                   10

<210> SEQ ID NO 12
```

```
<211> LENGTH: 9
<212> TYPE: PRT
<213> ORGANISM: Influenza A virus

<400> SEQUENCE: 12

Ser Arg Tyr Trp Ala Ile Arg Thr Arg
1               5

<210> SEQ ID NO 13
<211> LENGTH: 9
<212> TYPE: PRT
<213> ORGANISM: homo sapiens

<400> SEQUENCE: 13

Val Met Ala Pro Arg Thr Leu Ile Leu
1               5

<210> SEQ ID NO 14
<211> LENGTH: 18
<212> TYPE: PRT
<213> ORGANISM: artificial
<220> FEATURE:
<223> OTHER INFORMATION: OVAp.beta2m.Kb construct.

<400> SEQUENCE: 14

Ser Ile Ile Asn Phe Glu Lys Leu Gly Gly Gly Ala Ser Gly Gly Gly
1               5                   10                  15

Gly Ser

<210> SEQ ID NO 15
<211> LENGTH: 18
<212> TYPE: PRT
<213> ORGANISM: artificial
<220> FEATURE:
<223> OTHER INFORMATION: OVAp.beta2m.Kb construct.  Heavy chain
      mutation Y84A.

<400> SEQUENCE: 15

Ser Ile Ile Asn Phe Glu Lys Leu Gly Gly Gly Ala Ser Gly Gly Gly
1               5                   10                  15

Gly Ser

<210> SEQ ID NO 16
<211> LENGTH: 18
<212> TYPE: PRT
<213> ORGANISM: artificial
<220> FEATURE:
<223> OTHER INFORMATION: OVAp.beta2m.Kb construct.  Heavy chain
      mutations T80C, Y84A.

<400> SEQUENCE: 16

Ser Ile Ile Asn Phe Glu Lys Leu Gly Gly Gly Ala Ser Gly Gly Gly
1               5                   10                  15

Gly Ser

<210> SEQ ID NO 17
<211> LENGTH: 18
<212> TYPE: PRT
<213> ORGANISM: artificial
<220> FEATURE:
<223> OTHER INFORMATION: OVAp.beta2m.Kb construct.  Heavy chain
      mutations T80C, Y84A.

<400> SEQUENCE: 17

Ser Ile Ile Asn Phe Glu Lys Leu Cys Gly Gly Ala Ser Gly Gly Gly
```

<210> SEQ ID NO 18
<211> LENGTH: 18
<212> TYPE: PRT
<213> ORGANISM: artificial
<220> FEATURE:
<223> OTHER INFORMATION: OVAp.beta2m.Kb construct. Heavy chain mutations T80C, Y84A.

<400> SEQUENCE: 18

Ser Ile Ile Asn Phe Glu Lys Leu Gly Cys Gly Ala Ser Gly Gly Gly
1               5                   10                  15

Gly Ser

<210> SEQ ID NO 19
<211> LENGTH: 18
<212> TYPE: PRT
<213> ORGANISM: artificial
<220> FEATURE:
<223> OTHER INFORMATION: OVAp.beta2m.Kb construct. Heavy chain mutation Y84C.

<400> SEQUENCE: 19

Ser Ile Ile Asn Phe Glu Lys Leu Gly Gly Gly Ala Ser Gly Gly Gly
1               5                   10                  15

Gly Ser

<210> SEQ ID NO 20
<211> LENGTH: 18
<212> TYPE: PRT
<213> ORGANISM: artificial
<220> FEATURE:
<223> OTHER INFORMATION: OVAp.beta2m.Kb construct. Heavy chain mutation Y84C.

<400> SEQUENCE: 20

Ser Ile Ile Asn Phe Glu Lys Leu Gly Cys Gly Ala Ser Gly Gly Gly
1               5                   10                  15

Gly Ser

<210> SEQ ID NO 21
<211> LENGTH: 18
<212> TYPE: PRT
<213> ORGANISM: artificial
<220> FEATURE:
<223> OTHER INFORMATION: OVAp.beta2m.Kb construct. Heavy chain mutation Y84C.

<400> SEQUENCE: 21

Ser Ile Ile Asn Phe Glu Lys Leu Gly Gly Cys Ala Ser Gly Gly Gly
1               5                   10                  15

Gly Ser

<210> SEQ ID NO 22
<211> LENGTH: 18
<212> TYPE: PRT
<213> ORGANISM: artificial
<220> FEATURE:
<223> OTHER INFORMATION: OVAp.beta2m.Kb construct. Heavy chain mutation Y84C.

<400> SEQUENCE: 22

Ser Ile Ile Asn Phe Glu Lys Leu Gly Gly Gly Cys Ser Gly Gly
1               5                   10                  15

Gly Ser

<210> SEQ ID NO 23
<211> LENGTH: 18
<212> TYPE: PRT
<213> ORGANISM: artificial
<220> FEATURE:
<223> OTHER INFORMATION: OVAp.beta2m.Kb construct. Heavy chain
      mutations Y84A, N86C.

<400> SEQUENCE: 23

Ser Ile Ile Asn Phe Glu Lys Leu Gly Gly Gly Ala Cys Gly Gly
1               5                   10                  15

Gly Ser

<210> SEQ ID NO 24
<211> LENGTH: 18
<212> TYPE: PRT
<213> ORGANISM: artificial
<220> FEATURE:
<223> OTHER INFORMATION: OVAp.beta2m.Kb construct. Heavy chain
      mutation Y84A.

<400> SEQUENCE: 24

Ser Ile Ile Asn Tyr Glu Lys Leu Gly Gly Gly Ala Ser Gly Gly
1               5                   10                  15

Gly Ser

<210> SEQ ID NO 25
<211> LENGTH: 18
<212> TYPE: PRT
<213> ORGANISM: artificial
<220> FEATURE:
<223> OTHER INFORMATION: OVAp.beta2m.Kb construct. Heavy chain
      mutation Y84C.

<400> SEQUENCE: 25

Ser Ile Ile Asn Tyr Glu Lys Leu Gly Cys Gly Ala Ser Gly Gly
1               5                   10                  15

Gly Ser

<210> SEQ ID NO 26
<211> LENGTH: 19
<212> TYPE: PRT
<213> ORGANISM: artificial
<220> FEATURE:
<223> OTHER INFORMATION: SCT Ld construct

<400> SEQUENCE: 26

Gln Leu Ser Pro Phe Pro Phe Asp Leu Gly Gly Gly Ala Ser Gly
1               5                   10                  15

Gly Gly Ser

<210> SEQ ID NO 27
<211> LENGTH: 19
<212> TYPE: PRT
<213> ORGANISM: artificial
<220> FEATURE:
<223> OTHER INFORMATION: QL9 Ld construct Y84A

<400> SEQUENCE: 27

Gln Leu Ser Pro Phe Pro Phe Asp Leu Gly Gly Gly Ala Ser Gly Gly

```
<210> SEQ ID NO 28
<211> LENGTH: 19
<212> TYPE: PRT
<213> ORGANISM: artificial
<220> FEATURE:
<223> OTHER INFORMATION: QL9 Ld construct Y84C, L2C (dtSCT)

<400> SEQUENCE: 28

Gln Leu Ser Pro Phe Pro Phe Asp Leu Gly Cys Gly Ala Ser Gly Gly
1               5                   10                  15

Gly Gly Ser

<210> SEQ ID NO 29
<211> LENGTH: 8
<212> TYPE: PRT
<213> ORGANISM: Gallus gallus

<400> SEQUENCE: 29

Ser Ile Ile Asn Phe Glu Lys Leu
1               5

<210> SEQ ID NO 30
<211> LENGTH: 8
<212> TYPE: PRT
<213> ORGANISM: Homo sapiens

<400> SEQUENCE: 30

Ser Ile Tyr Arg Tyr Tyr Gly Leu
1               5

<210> SEQ ID NO 31
<211> LENGTH: 8
<212> TYPE: PRT
<213> ORGANISM: Vesicular stomatitis virus

<400> SEQUENCE: 31

Arg Gly Tyr Val Tyr Gln Gly Leu
1               5

<210> SEQ ID NO 32
<211> LENGTH: 9
<212> TYPE: PRT
<213> ORGANISM: mus musculus

<400> SEQUENCE: 32

Gln Leu Ser Pro Phe Pro Phe Asp Leu
1               5

<210> SEQ ID NO 33
<211> LENGTH: 9
<212> TYPE: PRT
<213> ORGANISM: murine cytomegalovirus

<400> SEQUENCE: 33

Tyr Pro His Phe Met Pro Thr Asn Leu
1               5

<210> SEQ ID NO 34
<211> LENGTH: 15
<212> TYPE: PRT
<213> ORGANISM: artificial
```

```
<220> FEATURE:
<223> OTHER INFORMATION: [G4S]3 linker

<400> SEQUENCE: 34

Gly Gly Gly Gly Ser Gly Gly Gly Gly Ser Gly Gly Gly Gly Ser
1               5                   10                  15

<210> SEQ ID NO 35
<211> LENGTH: 20
<212> TYPE: PRT
<213> ORGANISM: artificial
<220> FEATURE:
<223> OTHER INFORMATION: [G4S]4 linker

<400> SEQUENCE: 35

Gly Gly Gly Gly Ser Gly Gly Gly Gly Ser Gly Gly Gly Gly Ser Gly
1               5                   10                  15

Gly Gly Gly Ser
            20

<210> SEQ ID NO 36
<211> LENGTH: 8
<212> TYPE: PRT
<213> ORGANISM: artificial
<220> FEATURE:
<223> OTHER INFORMATION: Ova5y variant of Ova peptide

<400> SEQUENCE: 36

Ser Ile Ile Asn Tyr Glu Lys Leu
1               5

<210> SEQ ID NO 37
<211> LENGTH: 10
<212> TYPE: PRT
<213> ORGANISM: artificial
<220> FEATURE:
<223> OTHER INFORMATION: peptide for heavy chain H-2KbY84C

<400> SEQUENCE: 37

Ser Ile Ile Asn Phe Glu Lys Leu Gly Cys
1               5                   10

<210> SEQ ID NO 38
<211> LENGTH: 20
<212> TYPE: PRT
<213> ORGANISM: artificial
<220> FEATURE:
<223> OTHER INFORMATION: [G4S]5 linker

<400> SEQUENCE: 38

Gly Gly Gly Ser Gly Gly Gly Ser Gly Gly Gly Ser Gly Gly Gly Ser
1               5                   10                  15

Gly Gly Gly Ser
            20
```

DISULFIDE TRAP MHC CLASS I MOLECULES AND USES THEREFOR

CROSS-REFERENCE TO RELATED APPLICATIONS

This application claims priority to Provisional Application Ser. No. 60/840,521 filed on Aug. 28, 2006, which is incorporated herein by reference in its entirety.

STATEMENT REGARDING FEDERALLY SPONSORED RESEARCH OR DEVELOPMENT

This work was supported at least in part by National Institutes of Health grants AI055849 and AI27568.

INTRODUCTION

A critical threshold density of cell surface MHC/peptide complexes is required to prime naïve CD8 T cells and to activate cytolytic CD8 effectors. Although the affinity of the peptide for the MHC is a major factor in determining the immunogenicity of any particular peptide antigen, immunodominant peptides in CD8 T cell responses to pathogens are not always the tightest class I binders (1). This is because immunodominance is also influenced by levels of donor protein in the cytosol, by the relative efficiency of processing particular epitopes, and by pathogen interference with antigen presentation. Moreover, the T cell repertoire has a major impact on determining which peptides are immunodominant in CD8 T cell responses (1-3). The fact that certain antigenic peptides are difficult to process and/or are relatively weak binders has considerable implications on vaccination strategies to pathogens and tumors (4). This is particularly the case in primary CD8 T cell responses that require cross priming. In the case of cross-priming, professional APCs which have acquired antigen exogenously, rather than by endogenous synthesis in the cytosol, will only be able to activate T cells if class I/peptide complexes have a sufficient half-life (5).

Tetramers and other multivalent staining reagents used to enumerate CD8 T cell populations in response to pathogens or tumors are also highly influenced by class I peptide binding affinity. Such reagents are typically made with soluble recombinant class I heavy chains expressed in bacteria and refolded with synthetic peptides (6). The production and stability of a tetramer is determined by the affinity of the peptide for the MHC, thus limiting the study of T cells specific for lower-affinity complexes.

Class I major histocompatibility complex (MHC) proteins serve a critical role in the adaptive immune response by binding short peptide fragments intracellularly and presenting them at the cell surface for surveillance by cytotoxic T lymphocytes (CTLs) (69-72). Structural studies of human and murine MHC class I proteins have revealed that peptides of 8-10 residues in length are presented to T cell receptors (TCRs) in the context of a narrow groove formed by two antiparallel α-helices positioned above an eight-strand, antiparallel β-sheet (73-77). This peptide-binding platform is comprised of the α1 and α2 domains of a polymorphic heavy chain (HC), which also contains an immunoglobulin-like α3 domain. The surface expression of peptide-MHC complexes requires the association of this heavy chain with an invariant, light chain, β2-microglobulin ($\beta_2$m), which forms extensive contacts with both the α3 domain and the peptide-binding platform.

The ability of MHC proteins to activate T cells is critically dependent on the amount of peptide-MHC expressed at the cell surface (58, 60, 78). However, certain MHC-presented epitopes that have the capacity to activate the immune response are not expressed efficiently at the plasma membrane. This is because the cell-surface density of these protein complexes can be influenced by a variety of factors such as, for example, efficiency of antigen processing (79, 80), specificity of peptide translocation into the ER (81), interference by viral pathogens (1), and the kinetic stability of the peptide-MHC complex itself (82). Although T cell responses to such peptide-MHC complexes tend to be subdominant, the efficient induction of such responses has been shown to be crucial in achieving a broader and more effective antiviral and antitumor immunity (7, 9, 83-85). We have engineered peptide-MHC complexes as single chain trimers (SCTs) (10, U.S. patent application Ser. No. 11/397,377 filed Apr. 4, 2006). These engineered proteins comprise an antigenic peptide followed by a flexible linker that connects the C terminus of the peptide to the N terminus of β2-microglobulin (($\beta$2m), and another flexible linker, which connects the C terminus of β2m to the N terminus of the heavy chain (10). In some configurations, SCTs can have the format: secretion signal sequence-antigenic peptide-linker 1-mature β2-microglobulin-linker 2-mature class I heavy chain (FIG. 1A). In some configurations, Linker I can have sequence GGGGSGGGGSGGGGS (SEQ ID NO: 34) and linker 2 can have sequence GGGGSGGGGSGGGGSGGGGS (SEQ ID NO: 35). SCTs and nucleic acids which encode them have applications as DNA vaccines to tumors, as tetramers for enumerating populations T cells, and as probes of lymphocyte development (4, 10, 11, 13, 16-19).

To characterize peptide binding by an SCT, we have focused most of our attention on the SCT construct of the well-characterized Kb/OVA complex. This SCT was found to have remarkable qualities including extended cell surface half-life and the ability to stimulate potently T cells that recognize native Kb/OVA (10) We also chose the Kb/OVA complex because of the large number of immunological reagents that are available. We found this SCT is 1000-fold more refractory to exogenous peptide binding compared to Kb loaded with endogenous peptides. However, the SCT was more susceptible to exogenous peptide binding compared to native Kb/OVA (11).

Initial studies with these prototypic SCTs have shown that when transfected they assemble rapidly in the ER, show extended surface half-life, and are refractory to binding of exogenous peptide in comparison to $K^b$ loaded with endogenous peptides (10).

The ability of SCTs to retain binding of a single peptide has been exploited for the production of multimeric staining reagents, which have been used for T cell expansion and diagnostics (86-89). This property of SCTs also affords novel opportunities for the production of tumor vaccines due to the feet that some CTL epitopes recognized by cancer patents appear to bind their respective MHCs with relatively weak affinity (90). Furthermore, since the single-chain peptide is preprocessed and preloaded, an SCT expressed following vaccination with DNA comprising a sequence encoding the SCT can be a potent in vivo stimulator of CD8 T cells (13, 16), SCT technology is therefore a highly efficacious method for tumor vaccination. In strong support of this conclusion, incorporation of a tumor-specific peptide into an SCT was recently shown to elicit robust CTL responses and complete protection against a lethal tumor challenge in a mouse model (4, 16). Lastly, SCTs have been successfully used as novel probes for the study of NK cell biology (17, 18) and T cell activation (19).

In spite of these exciting and diverse applications of SCTs, certain limitations regarding their general applicability have been recently noted. One such limitation is that SCTs constructed with relatively low affinity peptides do not assemble as efficiently nor do they prevent the binding of exogenous peptide as effectively as SCT formed with relatively high affinity peptides. These limitations were presumed to reflect impaired F pocket anchoring resulting from the linker extension (11).

Although SCT tetramers retain the ability to bind antigen-specific T cells (11, 102, 103), there are certain limitations to using SCT material. First, excess peptide cannot be used during in vitro refolding of solubilized *E. coli* inclusion bodies of SCTs. This means that refolding efficiency may not be optimal for some SCT constructs. The second limitation is a problem with expression in *E. coli*. Endogenous bacterial methionyl aminopeptidase activity must cleave initiator N-formyl methionine (fMet) off of the SCT to reveal the correct antigen sequence for binding in the SCT groove. However, this cleavage event is not universal; it depends on the size of amino acid side chain which follows the initiator fMet (104, 105). Thus expression of SCTs for tetramers is limited to those that have antigenic peptide sequences that allow for fMet cleavage.

SUMMARY

The present inventors disclose molecules designated herein as "disulfide traps." A disulfide trap comprises an MHC antigen peptide covalently attached to an MHC class I heavy chain. The covalent linkage between the antigen peptide and the MHC class I heavy chain comprises a disulfide bond, which extends between a pair of oxidized cysteines (i.e., a cystine). The cysteines comprising the disulfide bond comprise a first cysteine and a second cysteine. A first cysteine, is comprised by a linker extending from the carboxy terminal of an MHC antigen peptide, and a second cysteine is comprised by an MHC class I heavy chain, in particular an MHC class I heavy chain which has a non-covalent binding site for the antigen peptide, in some configurations, a disulfide trap can comprise one contiguous polypeptide chain as well as a disulfide bridge. In other configurations, a disulfide trap can comprise two contiguous polypeptide chains which are attached via the disulfide bridge as the only covalent linkage.

In various configurations of a disulfide trap, the sequence extending from the carboxy terminal of the peptide can comprise at least one amino acid in addition to the cysteine, including one or more glycines, one or more, alanines, and/or one or more serines. In some configurations, the sequence extending form the carboxy terminal of the peptide can comprise a carboxy-terminal cysteine.

In various configurations, the second cysteine can be a mutation in the MHO class I heavy chain. In some aspects, the mutation can be a cysteine which substitutes for an amino acid of the MHC class I heavy chain, or a cysteine addition to the MHC class I heavy chain. In various configurations, the second cysteine can be situated from about 1 to about 100 amino acids from the amino terminal of the MHC class I heavy chain, in some aspects, the second cysteine can be a Y84C substitution (i.e., a substitution of tyrosine-84 of a MHC class I heavy chain with a cysteine). In other aspects, the second cysteine can be a T80C substitution (i.e., a threonine-80 to cysteine substitution) or an A86C substitution (i.e., an alanine-86 to cysteine substitution).

The present inventors have also developed disulfide trap single chain trimer (dtSCT) molecules. The inventors have found that a disulfide bond can effectively trap an antigen peptide in the class I groove of an SCT if the SCT comprises a first cysteine in a Gly-Ser linker extending between the C-terminus of the peptide and the $\beta_2$-microglobulin, and a second cysteine in a proximal heavy chain position. In various configurations, a disulfide trap such as a dtSCT does not succumb to high concentrations of competitor peptide, even when the dtSCT is based on a low-affinity complex. The present inventors have also obtained similar results for dtSCT's comprising either Kb/OVA sequences or a second MHC allele, H-2Ld, known for its relatively poor peptide-binding capacity (14, 15).

In some configurations, a disulfide trap can comprise any antigen that can bind a corresponding MHC class I heavy chain or MHC class I-like antigen presenting molecule such as CD1 (Altamirano, M. M., et. al., Proc. Nat'l. Acad. Sci. 98: 3288-3293, 2001). In some aspects, an antigen peptide sequence can be that of a peptide which can be presented by an MHC class I molecule, in various configurations, an antigen peptide sequence can comprise from about 8 to about 15 contiguous amino acids. In some configurations, the antigen peptide sequence can comprise 9 contiguous amino acids. In various aspects, a peptide sequence can be that of a protein fragment, wherein the protein is a pathogen protein or a cellular protein, such as, for example, a protein expressed by a cancer cell. In some aspects, an antigen can comprise an antigen peptide such as that of an HLA-A restricted peptide or HLA-B restricted peptide, such as an HLA-A*0201-restricted peptide. In some aspects, an antigen peptide can have a sequence as set forth in Table 1:

TABLE 1

Antigen Peptide Sequences*

| Name | Source | Sequence | Identification |
|---|---|---|---|
| CMVpp65 | Cytomegalovirus | NLVPMVATV | SEQ ID NO: 1 |
| EBV BMLF I | Ebstein-Barr virus | GLCTLVAML | SEQ ID NO: 2 |
| fluM1 | Influenza A virus | GILGFVFTL | SEQ ID NO: 3 |
| G209-2M | human melanoma | IMDQVPFSV | SEQ ID NO: 4 |
| G280-9V | human melanoma | YLEPGPVTV | SEQ ID NO: 5 |

*Sequences are presented using standard single-letter amino acid abbreviations as follows:
A = alanine; C = cysteine; D = aspartic acid; E = glutamic acid; F = phenylalanine; G = glycine; H = histidine; I = isoleucine; K = lysine; L = leucine; M = methionine; N = asparagine; P = proline; Q = glutamine; R= arginine; S = serine; T = threonine; V = valine; W = tryptophan; Y = tyrosine.

In some aspects, the MHC class I heavy chain can be an HLA-A, an HLA-B, an HLA-C, an HLA-E, an HLA-F, or an HLA-G class I heavy chain, and an antigen can comprise an antigen peptide corresponding to the MHC class I heavy chain, such as an HLA-A, an HLA-B, an HLA-C, an HLA-E, an HLA-F, or an HLA-G restricted peptide, respectively.

In some aspects, the present inventors have developed methods for producing disulfide trap molecules including dtSCT's. These methods include expressing a nucleic acid vector in a suitable host cell, wherein the vector comprises a promoter and/or an IRES operably linked to a sequence encoding a polypeptide comprising the primary amino acid sequence of a disulfide trap (including a dtSCT). Following translation of an mRNA, a disulfide bridge forms between the cysteines of the nascent polypeptide chain. A disulfide trap synthesized within a host cell can be recognized at the cell surface by both antibodies and T cells specific for the peptide-receptor complex. In other aspects, a disulfide trap can be produced by separately expressing a) an antigen peptide comprising an extension at its carboxy terminus, wherein the extension comprises a cysteine, and b) an MHC class I heavy chain comprising a cysteine.

In some aspects, the present inventors disclose vaccines against tumors and pathogens such as bacteria and viruses. These vaccines comprise either a disulfide trap, a nucleic acid comprising a sequence encoding a disulfide trap, or a combination thereof.

In some aspects, the present inventors disclose multivalent MHC/peptide complexes comprising a disulfide trap. In various applications, such multivalent complexes can be used for enumerating populations of T cells during infections or malignancies, or a probes for identifying cells such as subsets of T cells. Such probes can be used, for example, to monitor T cell-specific immune responses during infection or malignancy.

To extend the novel applications of SCT for vaccines and probes for pathogen surveillance, we took a structure-based approach to engineer three consecutive SCT designs that are characterized here biophysically and functionally in the context of their high resolution crystal structures. Progressive generations of SCTs show dramatic improvements in linker accommodation, C-terminal peptide anchoring, and improved refractoriness to exogenous peptide binding. These modifications in SCT design were made without disrupting the MHC fold as determined by structural comparisons, highly sensitive T cells assays, and expressing SCTs as tetramers to stain pathogen-specific T cells.

Although the data presented here use the well-defined $K^b$-Ova model system, SCT approaches clearly extend to other mouse and human class I peptide-MHC complexes. To date we and others have reported SCT constructs with human HLA-A2, -B27, -E or mouse H2-$K^b$, -$L^d$, -$D^b$ each bound by several different respective peptide ligands (18). This general applicability of the SCT format is in large part reflected by the highly conserved atomic basis of C terminal peptide anchoring. Thus we fully expect that the new SCT designs will also extend to other mammalian class I peptide-MHC complexes.

SCTs have now undergone three generations of design. In our initial protein engineering studies we determined the order in which to connect each component into the SCT and the optimal length of each spacer allowing efficient surface presentation (10). In the second generation we re-engineered the peptide-binding groove to accommodate the linker between the antigenic peptide and $\beta_2$m (11). Lastly, in the third generation, disclosed herein, we introduce a disulfide trap. Without being limited by theory, a disulfide trap in the F pocket is believed to enhance the association of the peptide for the MHC within the SCT format. Our structural data show that the Y84A and Y84C mutations restructure the $K^b$ groove to open a channel allowing the linker to freely extrude from the peptide-binding platform. In addition, experimental electron density maps for the $SCT^{Y84C-PBL2C}$ protein show the presence of a disulfide bond between $Cys^{PBL2}$ and $Cys^{84}$. We also present experimental evidence that the presence of this disulfide bridge increases the thermal stability of the SCT format and effectively prevents binding of competitor peptides. Consequently, such disulfide traps have many applications, such as, for example, as vaccines against pathogens and tumors, or for staining reagents to enumerate pathogen-specific T cells. In particular, disulfide traps are noteworthy for physiologically important antigenic peptides that are not tight binders.

We have tested the capacity of a disulfide trap to compensate for poor peptide binding, using a disulfide-trapped SCT constructed with a weakly binding variant of Ova (Ova5y, SIINYEKL) SEQ ID NO: 36) (50, 78). We show that introduction of the disulfide trap in the Ova5y-based SCT significantly improves its surface expression and completely prevents exogenous peptides exchange of the weaker Ova5y analog. These results indicate that the disulfide-trap is able to enhance the association of weakly binding peptides within the SCT format. In addition, disulfide traps were successfully employed to make a SCT with an $L^d$ heavy chain and the QL9 peptide (31). $L^d$-QL9 complexes have poor surface stabilities and have proven to be difficult to refold as recombinant proteins. The disulfide-trapped form of $L^d$-QL9 is resistant to peptide competition akin to the one observed with Kb-based $SCT^{Y84C-PBL2C}$, indicating that disulfide trap technology can be applied to different MHC allelic forms, including ones with peptides of relatively poor binding affinities.

Induction of subdominant T cell responses has been shown to be critically important in producing a broadly effective immunity against tumors (84, 90) and pathogens (7, 9, 83). Such T cell responses are typically the result of less efficient antigen processing or weaker peptide-MHC association. Due to their preassembled nature SCT proteins bypass antigen processing, express efficiently at the cell surface, and exhibit extended cell surface half-fifes (10, 11). These properties make SCT proteins ideal for vaccine design. Recently, two studies on the use of SCT in DNA vaccinations for cancer prevention have been reported. In one of these studies a DNA construct encoding a breast cancer epitope derived from mammoglobin-A presented in the context of HLA-A2 as a SCT was used successfully in vaccination of doubly transgenic HLA-A2$^+$/hCD8$^+$ mice to induce the specific expansion of epitope-positive CTLs (16). While in the second study, C57BL/6 mice vaccinated with SCT proteins presenting an immunodominant epitope derived from HPV-16 E6 protein in the context of H-2$K^b$ exhibited significantly increased E6 peptide-specific responses compared to mice immunized, with DNA encoding E6 protein. Moreover 100% of the mice vaccinated with the SCT encoding DNA were protected against lethal challenge with E6-expressing tumors (4). It should be noted that these vaccine applications were done with first generation SCTs. SCTs incorporating disulfide traps offer further advantages for vaccines due to their improved stability and refractoriness to exogenous peptide binding.

In a second application, disulfide traps can be used for multimeric staining reagents to enumerate antigen-specific, CD8$^+$ T cells. Evidence for this conclusion is that tetramers with certain suboptimally binding peptides have been difficult to make or are particularly unstable once made (6). We disclose herein tetramers with only a disulfide-trapped peptide rather than an entire dtSCT. More specifically we determined that a soluble heavy chain with a Y84C mutation, produced in E. coli, can be refolded in the presence of a synthetic peptide with a GC extension. As reported herein, this approach can produce, in some configurations, disulfide trap tetramers, such as, for example, tetramers with disulfide-trap $K^b$-Ova. Such tetramers can stain T cells generated to the native $K^b$-Ova complex even in the context of a pathogen infection.

Some non-limiting advantages of using disulfide-trap tetramers over single-chain-trimer-(SCT)-based tetramers are disclosed herein. Although SCT tetramers retain the ability to bind antigen-specific T cells (11, 102, 103), there are certain limitations to using SCT material. First, excess peptide cannot be used during in vitro refolding of solubilized E. coli inclusion bodies of SCTs. This means that refolding efficiency may not be optimal for some SCT constructs. The second limitation is a problem with expression in *E. coli*. Endogenous bacterial methionyl aminopeptidase activity must cleave initiator N-formyl methionine (fMet) off of the SCT to reveal the correct antigen sequence for binding in the SCT groove. However, this cleavage event is not universal; it depends on the size of amino acid side chain which follows the initiator fMet (104, 105). Thus expression of SCTs for tetramers is limited to those that have antigenic peptide sequences that allow for fMet cleavage. Both of these limitations are obviated with the use of disulfide-trap technology. Excess peptide can be added to drive formation of the class I complexes during the in vitro refolding, and there is no limitations on the peptide sequence. This represents a more versatile approach for generating covalently linked MHC reagents, and can dramatically improve their shelf life and quality of staining, especially of those utilizing weaker-binding peptides. Such reagents allow for a more comprehensive T cell enumeration for diagnostics and study of T cell immune responses to pathogens and tumors.

BRIEF DESCRIPTION OF THE DRAWINGS

FIG. 12. Application of disulfide-trap (dt) technology for reagent generation; dtH-2 Kb-Ova tetramer staining of splenocytes from infected mice. A, Conventional and disulfide-trap tetramer staining of OT-1 T Cells OT-1 transgenic, splenocytes were harvested and stained with anti-CD8 and conventional tetramer conjugated to ARC (H-2Kb-Ova-APC, y-axis); disulfide-trap tetramer conjugated to PE (dtH-2Kb-Ova-PE, x-axis); or both tetramers. B, B6 mice were infected intravenously with 5×103 cfu of L.m.-Ova. After 7 days, splenocytes were harvested and stained as described above. C, As a negative control splenocytes from infected mice were stained with a Kb tetramer loaded with an irrelevant (SIYR) peptide. Flow cytometry was used to detect tetramer staining of CD8+ lymphocytes; dead cells were excluded by propidium iodide staining. The percentage of tetramer-stained CD8 T cells is given for relevant quadrants. Both tetramers stain similar numbers of CD8 T cells and the vast majority of antigen-specific CD8 T cells were positive for both tetramer formats, validating the specificity and utility of the tetramers constructed using disulfide-trap technology. Representative data are shown for one of four L.m.-Ova-infected mice.

DETAILED DESCRIPTION

Figure 1:
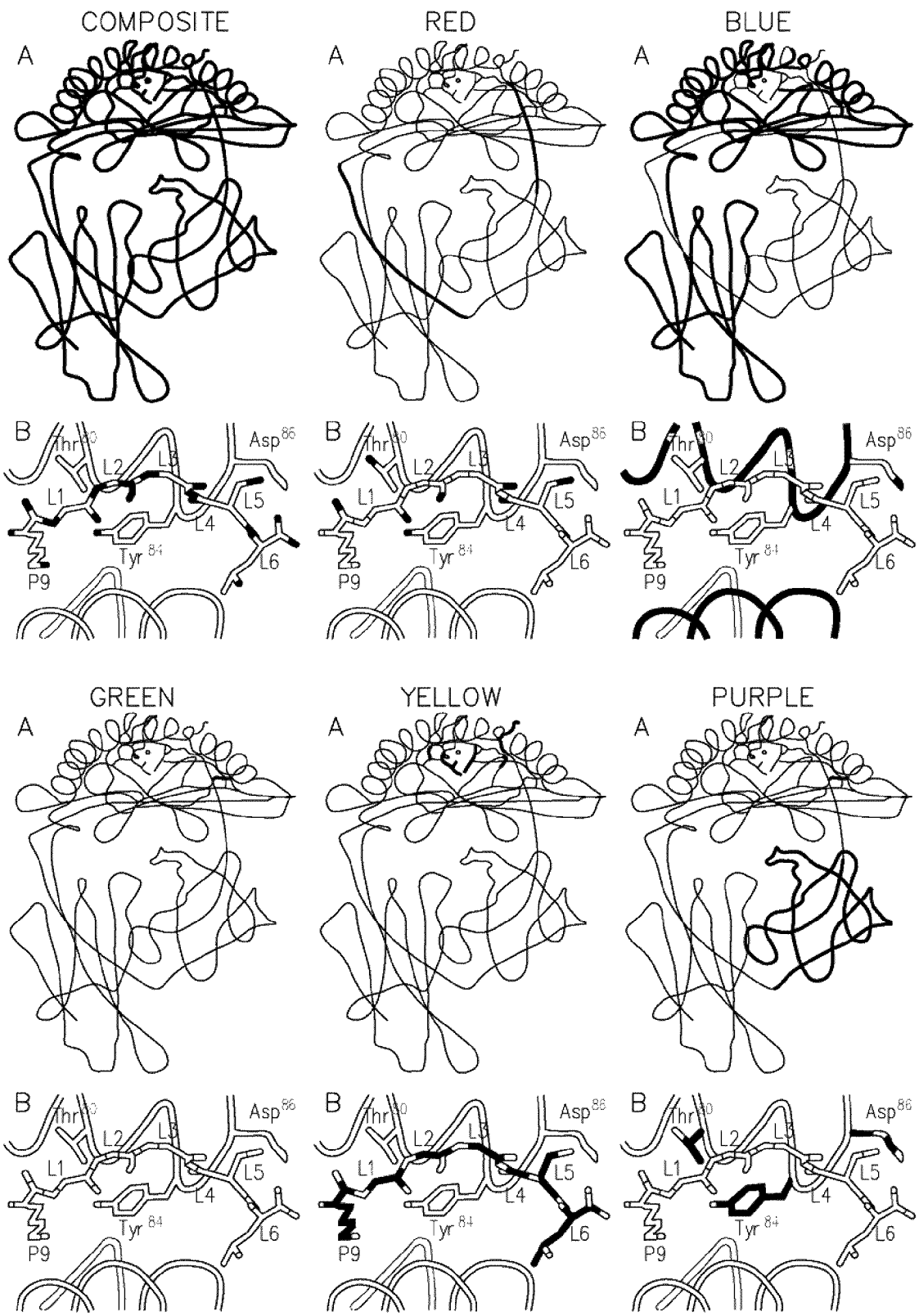
FIG. 1. A structure-based approach to engineering a disulfide bond in the Kb/OVA SCT. A, Schematic representation of the SCT based on the published structure for Kb/OVA (PDB code: 1VAC), including Gly-Ser linkers (red) and hypothetical location of the engineered disulfide bond (yellow). B, Analysis of superimposed class I and class II structures to select residues for cysteine mutagenesis. Kb heavy chain (blue) aligned with the 1-Ek-bound hemoglobin peptide (yellow, PDB code: 1FNE), which features covalent attachment with a Gly-Ser linker to the β chain of class II. This structure-based visual provided a framework for examining distances between residues on the class I heavy chain and along the first SCT linker. Three residues on the Kb heavy chain were selected for mutagenesis (purple): T80, Y84, and N86. Appropriately spaced residues in the linker were matched with each of these three heavy chain positions (see Table 2 and FIG. 2). The second linker position is also shown in purple for clear indication of the disulfide bond position in dtSCT constructs (Y84C, L2C). C, Schematic of HLA class I single-chain trimer (SCT) format and positioning of the disulfide trap. HLA SCTs were expressed in mammalian cells using the SCT format originally described by Yu, et al. (10). The signal peptide is precisely cleaved within the endoplasmic reticulum to reveal the antigenic sequence that folds into the HLA peptide-binding groove. Flexible linkers bridge the three summits of the class I heterotrimer and allow for presentation of a pre-processed CD8 epitope from a single open-reading frame. The first SCT linker perturbs conserved MHC interactions that normally engage, the peptide carboxyl group; however, this decrease in C-terminal anchoring was offset by the introduction of a disulfide bond (red in original) which locks the peptide securely into the HLA groove. Adapted from original color figure; panels highlight original colors against a dimmed background.

The present inventors have constructed disulfide trap molecules, such as SCTs which incorporate a disulfide trap. In various configurations, these novel dtSCT constructs can better accommodate the linker in the SCT groove, and can restore F pocket anchoring. The crystal structures of these SCT constructs along with their functional characterization indicate they can be widely applicable over a broader range of peptide affinities, greatly facilitating SCT-based approaches for pathogen surveillance.

The methods and compositions described herein utilize laboratory techniques well known to skilled artisans and can be found in laboratory manuals such as Sam brook, J., et al. Molecular Cloning: A Laboratory Manual, 3rd ed. Cold Spring Harbor Laboratory Press, Cold Spring Harbor, N.Y., 2001; Spector, D. L. et al, Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999.

A disulfide trap disclosed herein comprises an MHC antigen peptide covalently attached to an MHC class I heavy chain. The MHC antigen peptide can be any MHC antigen peptide, such as, for example, an antigen peptide disclosed in U.S. patent application Ser. No. 11/397,377 filed Apr. 4, 2006. The covalent linkage between the antigen peptide and the MHC class I heavy chain comprises a disulfide bond, which extends between a pair of oxidized cysteines (i.e., a cystine). The cysteines comprising the disulfide bond can comprise a first cysteine and a second cysteine. A first cysteine can be comprised by an oligopeptide, comprising the antigen peptide sequence and, extending from the carboxy terminal of antigen peptide, an extension comprising a cysteine. In various configurations, the sequence extending from the carboxy terminal of the peptide can comprise at least one amino acid in addition to the cysteine, such as, for example, one or more glycines, one or more, alanines, and/or one or more serines.

In various configurations, a second cysteine can be comprised by an MHC class I heavy chain, in particular an MHC class I heavy chain which has a non-covalent binding site for the antigen peptide, such as an MHC class I heavy chain disclosed in U.S. patent application Ser. No. 11/397,377.

In various configurations, the second cysteine can be a mutation in the MHC class I heavy chain. In some aspects, the mutation can be a cysteine which substitutes for an amino acid of the MHC class I heavy chain, or a cysteine addition to the MHC class I heavy chain. In various configurations, the second cysteine can be situated from about 1 to about 100 amino acids from the amino terminal of the MHC class I heavy chain. In some aspects, the second cysteine can be a Y84C substitution (i.e., a substitution of tyrosine-84 of a MHC class I heavy chain with a cysteine). In other aspects, the second cysteine can be a T80C substitution (i.e., a threonine-80 to cysteine substitution) or an A86C substitution (i.e., an alanine-86 to cysteine substitution). In some configurations, a disulfide trap can further comprise a Y84A substitution (i.e., a tyrosine-84 to alanine substitution).

The present inventors have also developed disulfide trap single chain trimer (dtSCT) molecules. The inventors have found that a disulfide bond can effectively trap an antigen peptide in the class I groove of an SCT if the SCT comprises a first cysteine in the Gly-Ser linker extending between the C-terminus of the peptide and the $\beta_2$-microglobulin, and a second cysteine in a proximal heavy chain position. A disulfide trap such as a dtSCT does not succumb to high concentrations of competitor peptide, even when the dtSCT is based on a low-affinity complex. Similar results have been for dtSCTs comprising either Kb/OVA sequences or a second MHC allele, H-2Ld, known for its relatively poor peptide-binding capacity (14, 15).

In some aspects, the present inventors have developed methods for producing disulfide trap molecules including dtSCT's. These methods include expressing a nucleic acid vector in a suitable host cell, wherein the vector comprises a promoter and/or an IRES operably linked to a sequence encoding a polypeptide comprising the primary amino acid sequence of a disulfide trap (including a dtSCT). Following translation of an mRNA, a disulfide bridge forms between the cysteines of the nascent polypeptide chain. A disulfide trap synthesized within a host cell can be recognized at the cell surface by both antibodies and T cells specific for the peptide-receptor complex.

The inventors herein disclose the engineering of a disulfide bond to lock peptide into the MHC class I binding groove. This disulfide trap was introduced into class I molecules expressed as single chain trimers, or SCTs. Some SCTs have been crystallized and high resolution structures analyzed. These structures verify the native class I conformation of the SCTs, as well as provide an anatomical basis for our biochemical and functional characterizations of the SCTs.

Some SCTs are class I MHC molecules expressed in the format: peptide-GGGGSGGGGSGGGGS (SEQ ID NO: 34)-mature β2m-GGGGSGGGGSGGGGSGGGGS (SEQ ID NO: 35)-mature class I heavy chain (FIG. 1A). These SCTs exhibit extended cell surface half-life and resistance to exogenous peptide binding, compared to Kb loaded with endogenous peptides (10). However, they are more susceptible to peptide replacement when compared to Kb loaded with OVA peptide (11). These findings are explained by the crystal structure of these SCTs, in which the spacer extending from the peptide disrupts the hydrogen bonding network that normally anchors the C-terminus of the peptide. These combined structure/function observations strongly support the model that the cell surface stability of the SCT and its refractoriness to exogenous peptide binding both reflect the ability of these SCTs to rebind quickly the covalently attached peptide.

Figure 5:
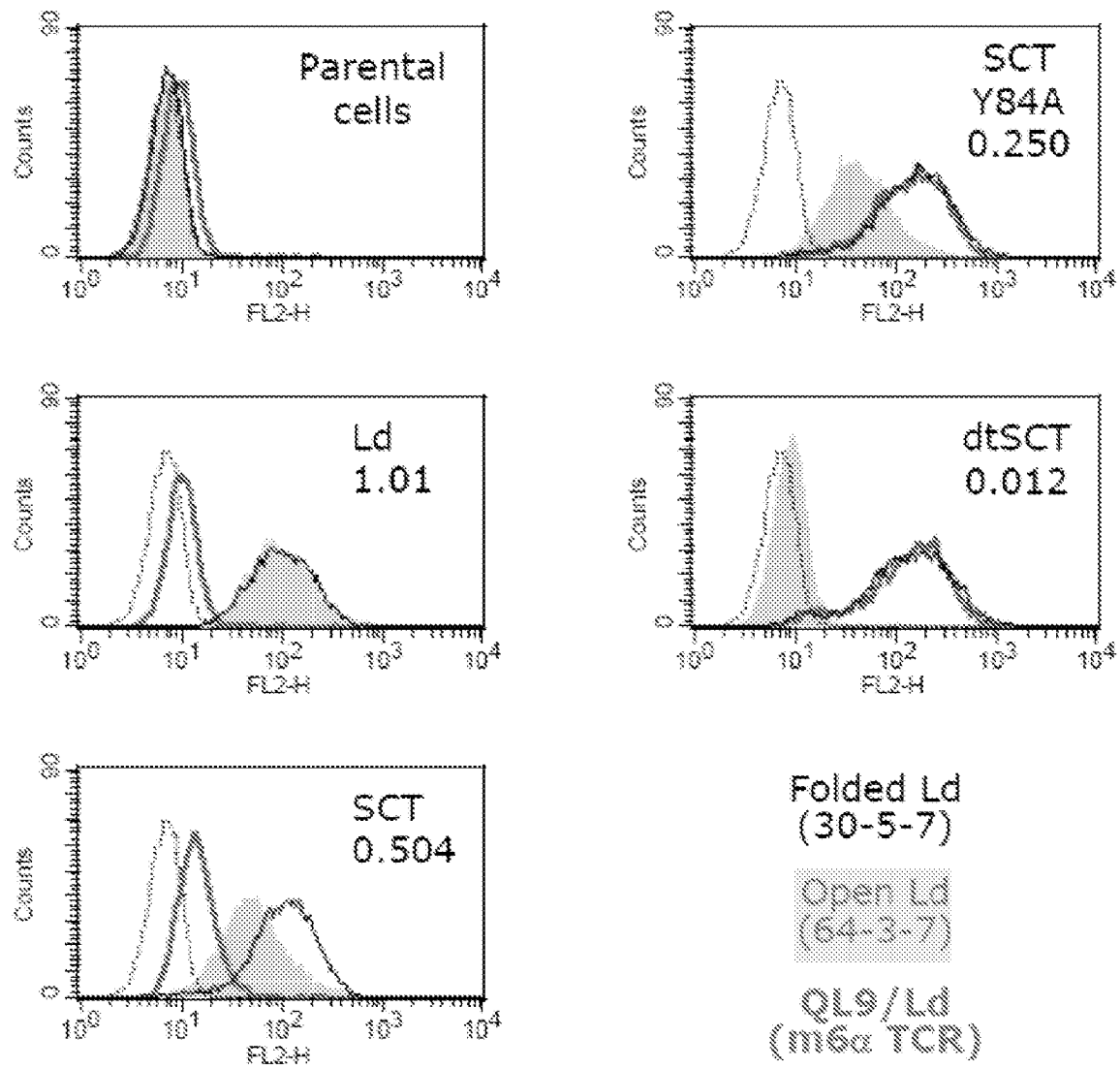
FIG. 5, Serological analysis of native Ld and QL9.β$_2$m.Ld SCT and dtSCT constructs. B6/WT3 (H-2$^b$) fibroblasts were transduced with native Ld, QL9.β$_2$m.Ld (first generation SCT), QL9.β$_2$m.Ld Y84A (second generation SCT), or QL9.β$_2$m.Ld dtSCT (third generation SCT). These cells were stained and analyzed by flow cytometry with a panel of three different reagents: mAb 30-5-7 (thin black line), specific for folded (peptide-occupied) Ld; mAb 64-3-7 (shaded in light gray), specific for open (peptide-empty) Ld; and the m6α TCR (thick dark gray line), a high-affinity recombinant TCR reagent specific for the Ld/QL9 complex. Background staining with secondary antibody alone is shown (dotted black line). Along with the label for each histogram is the ratio of open class I conformers to folded conformers (mAb 64-3-7 MFI/mAb 30-5-7 MFI).

Some other SCTs include the heavy chain substitution Y84A, which opens the peptide binding groove where the linker exits (11). The crystal structure of an SCT comprising Y84A shows that the linker adopts a more extended conformation compared to SCTs comprising Y84, In SCTs comprising Y84, the linker arches out and around heavy chain residues in the F pocket. This linker protrusion explains the improved detection of the latter by mAb 25-D1.16 (11) and by the TCR staining reagent m6α, in the case of the Ld SCT (FIG. 5).

Although functional SCTs have been constructed from a number of different mouse and human class I MHC/peptide complexes, SCTs constructed with high affinity peptides are clearly superior. The reason for this is now clear. As noted above, SCTs have disrupted F pocket anchoring and are thus dependent upon rebinding of the linker-attached peptide. Consequently, SCTs made with lower affinity peptides have higher steady state levels of peptide-empty conformers at the cell surface (see, e.g. FIG. 5).

The data presented herein confirm that the engineering of the disulfide bond was achieved at heavy chain position 84 and the second position on the linker extending from the C-terminus of the peptide. Migration of the dtSCT in non-reducing SDS-PAGE, as well as the ability of dtSCTs to exclude formidable concentrations of high-affinity competitor peptide, is consistent with formation of the disulfide bond in cells. This conclusion is further confirmed by electron density data from dtSCT crystals. In addition, we demonstrate herein that dtSCTs of two distinct MHC/peptide complexes are recognized by antibodies, TCR reagents, and T cells specific for native class I/peptide complexes. Accordingly, the disulfide-trap approach presented here befits other H-2 and HLA complexes. Moreover, we show herein that dtSCT construction offers great utility for studying lower affinity MHC/peptide complexes, as weak Kb/peptide and Ld/peptide complexes can both be expressed with a disulfide trap and, furthermore, exclude competitor peptides. As revealed by crystal structure, cysteine residues in the dtSCT provide not only a disulfide bond, but also better linker accommodation and, unexpectedly, additional hydrogen bonds. These hydrogen bonds improve peptide anchoring in the F pocket of the dtSCT groove, compared to SCTs that do not comprise a disulfide trap.

Recent, applications of SCTs have begun to provide unique insights into our understanding of the complex role of MHC class I molecules in lymphocyte development and function (17-19). In a seminal study of the role of class I in natural killer (NK) cell development, Kim et al. examined NK cells from mice that expressed the OVA.$\beta_2$m.Kb SCT as a transgene, but not $\beta_2$m or other class I genes (17). These experiments established that expression of a single MHC class I molecule selectively licenses NK functional activity only in NK precursors with an inhibitory receptor specific for this MHC class I molecule. The SCT also promises to play a pivotal role in studies of CD8 T cell development. To study the development of CD8 T cell in the context of a single class I/peptide complex, we have expressed the OVA.$\beta_2$m.Kb SCT as a transgene and bred to a Kb-, Db-, $\beta_2$m-deficient background. Importantly, the covalently attached OVA excludes the binding of endogenous peptides, as demonstrated by the strong primary CTL response of T cells from these mice when cultured with cells expressing Kb loaded with endogenous peptides. However, previous studies of CD4 T cell development established that it is imperative to absolutely ablate endogenous peptide binding in order to make definitive conclusions about the role of peptide in thymic selection (61-63). Thus, transgenic mice that express a disulfide-trap OVA.$\beta_2$m.Kb SCT provide important tools for approaching a key outstanding question in αβ T cell development, i.e., the relationship between the MHC-bound selecting peptide in the thymus vs. the activating peptide in periphery.

Disulfide traps, including dtSCTs, have clinical applications. There are already four reports demonstrating that vaccination with plasmid DNA encoding an SCT leads to generation of specific antibodies and/or CTL. In the report by Yu et al., DNA encoding the OVA.$\beta_2$m.Kb SCT was used to vaccinate BALB/c mice (10). BALB/c mice vaccinated with plasmid encoding SCT were found to generate anti-Kb/OVA antibody, demonstrating that the SCTs are expressed as intact structures by DNA vaccination. Furthermore, in a recent report by Primeau et al. (13), syngeneic immunization of plasmid DNA encoding SCT was found to elicit antigen-specific. CTLs. Extending these findings are two exciting recent studies showing that SCT DNA vaccination is highly effective for priming T cells in clinically relevant model systems. In one of these studies, mice doubly transgenic for HLA-A2 and human CD8 were vaccinated with DNA encoding an SCT that included HLA-A2 and a breast cancer-associated peptide derived from mammaglobin (16). This vaccination with SCT DNA was reported by Jaramillo et al. to induce a significant expansion of CTLs capable of specific detection of A2 positive human breast cancer cells. Another recent study by Huang et al. tested SCT DNA vaccination in a mouse model of human papillomavirus (HPV)-induced tumors such as cervical cancer (4). The HPV oncoprotein E6 is responsible for malignant transformation and is consistently expressed in HPV-associated tumors. Peng et al. identified an immunodominant CTL epitope, of the E6 protein that binds to the mouse class I molecule Kb (64) and this E6 epitope was then incorporated into an SCT (E6p.$\beta_2$m.Kb). In this study, B6 mice were vaccinated with plasmid DNA encoding either the SCT or the intact E6 protein alone, DNA vaccination of B6 mice with the SCT elicited high levels of CTL, whereas DNA vaccination with only E6 displayed little response over background. Furthermore, DNA vaccination with SCT protected mice against a lethal tumor challenge, whereas vaccination with DNA encoding E6 or OVA-$\beta$2m-Kb SCT did not. These experimental findings represent the first evidence that SCTs can have a significant advantage over protein-based vaccine approaches in a clinically relevant model system. The success of SCTs was credited to the fact they are antigen processing-independent, do not need to compete with endogenous peptide, and are more stable at the cell surface due to their covalent nature (4). Each of these DNA vaccination approaches used first generation SCTs. Although SCT-based DNA vaccines show great promise, they can be improved even further by incorporation of the disulfide trap. Certain vaccines can elicit T cell responses to peptide determinants that bind relatively poorly to the MHC, in which case the use of dtSCTs can have a significant impact on the stability of antigenic determinants, and thus the level of vaccine protection.

Disulfide traps such as dtSCTs can be used as probes for cell staining. For example, a dtSCT multimer can be used as a high sensitivity FACS staining reagent, in comparison, tetramers for several defined CD8 T cell epitopes have been difficult to construct or are very unstable once constructed (65). Furthermore, in vivo applications of recombinant MHC molecules to modulate CD8 responses can require reagents with longer in vivo half-lives and greater thermal stability (66-68). dtSCT crystal structure reveals that an analogous disulfide trap can be incorporated into soluble, recombinant class I molecules without the SCT linkers. This can be done by refolding the class I heavy chain harboring a Y84C mutation with recombinant $\beta_2$m and a synthetic peptide having a GC extension. This approach works for at least Kb/OVA complexes: the disulfide trap forms properly upon in vitro refolding, and dtMHC tetramers bind T cells specific for the native complex. Accordingly, the present teachings include the construction of stable multimers of lower-affinity MHC/peptide complexes and make possible more comprehensive analyses off cell responses to pathogens and tumors.

EXAMPLES

The following examples are illustrative, and are not intended to be limiting.

The following materials and methods were used in the examples presented herein.

Cell Lines and Antibodies—Triple knockout fibroblasts ($^{Kb-/-Db-/-}\beta$2m$^{-/-}$; 3KO) are a transformed murine embryo fibroblast line derived from 3KO obtained from Stephen Jennings, (Louisiana State University Health Sciences Center). LM1.8 cells are L cells (H-2$^k$) transfected with ICAM (22) and were obtained from Dr. Phillipe Kourilsky (INSERM, Institut Pasteur, Paris, France). Monoclonal antibodies (mAbs) include the following: B8-24-3, which recognizes folded K$^b$ (American Type Culture Collection); Y3, which recognizes folded H-2K molecules (23); 25-D1.16 (a gift of Dr. Jonathan Yewdell, National Institutes of Health), which recognizes K$^b$+SIINFEKL (SEQ ID NO: 29) peptide (24); and 64-3-7, which recognizes open (peptide-free) forms of Ld and other class I molecules tagged with the 64-3-7 epitope (25).

In some experiments, HeLa cells (human cervical carcinoma) transfected with 64-3-7 epitope-tagged HLA-B27 were used (37). Transfection of HeLa cells with cDNAs encoding A2 and B27 SCTs was performed using FuGene6 (Roche Diagnostics, Indianapolis, Ind.). Stable transfectants were selected and maintained in 0.6-1.2 mg/mL geneticin (Life Technologies, Grand Island, N.Y.), identified by flow cytometry, and cloned by limiting dilution. All cells were maintained in RPMI 1640 (Life Technologies) supplemented with 10% FCS (HyClone Laboratories, Logan, Utah), 2 mM L-glutamine, 0.1 mM nonessential amino acids, 1.25 mM HEPES, 1 mM sodium pyruvate, and 100 U/ml penicillin/streptomycin (all from the Tissue Culture. Support Center, Washington University School of Medicine, St. Louis, Mo.).

In some experiments, antibodies mAb BB7.2 and mAb ME-1 were used for immunoprecipitation and flow cytometry. BB7.2 is directed against folded A2 molecules (109), while ME-1 is directed against folded B27 (110). mAb HCA2 (a gift of H. Ploegh, Harvard Medical School, Boston, Mass.) recognizes unfolded A2 molecules (111). Open/peptide empty conformers of human class I molecules or SCT constructs were also detected by mAb 64-3-7 epitope-tagging (25, 31, 54-56). This antibody was also used for immunoprecipitations and immunoblots of epitope-tagged A2 and B27 and the corresponding SCT constructs.

Peptides—The OVA$_{257-264}$ peptide (SIINFEKL) (SEQ ID NO: 29) (26), SIYR peptide (SIYRYYGL) (SEQ ID NO: 30) (27), VSV8 peptide (RGYVYQGL) (SEQ ID NO: 31) (28), the QL9 peptide (QLSPFPFDL)) (SEQ ID NO: 32) (29-31), and the MCMV pp89 peptide (YPHFMPTNL) (SEQ ID NO: 33) (32) were synthesized on an Applied Biosystems Model 432A peptide synthesizer. Peptides were dissolved directly in culture media and incubated with cells for 5 hours or overnight before cytofluorometry or CTL assays.

DNA Constructs and Retroviral Transduction—Constructs were generated using standard techniques and confirmed by DNA sequence analysis. SCTs such as the OVA.$\beta_2$m.Kb SCT sequence were described previously (10, and U.S. patent application Ser. No. 11/397,377 which is incorporated by reference herein in its entirety), and the QL9.$\beta$2 m.Ld SCT was constructed similarly as follows. In amino-to-carboxy terminal order, the SCT comprises a secretion signal sequence such as that of $\beta_2$ m$^b$, followed by an antigen peptide sequence, then a first linker of 15 residues, GGGGSGGGGSGGGGS (SEQ ID NO: 34). An alanine residue can occupy the fourth position of the first linker (see Table 2), which can correspond to a convenient restriction site in a DNA construct encoding the SCT. This first linker is followed by the mature $\beta$2-microglobulin $\beta_2$-m$^b$ sequence, the second linker of 20 residues, GGGGSGGGGSGGGGSGGGGS (SEQ ID NO: 35), then the mature class I sequence. A dtSCT (such as QL9$\beta$2 m.Ld SCT) can also comprise a Y84A mutation, first described in the OVA.$\beta_2$ m.Kb SCT (11). This mutation and the cysteine mutations shown in Table 2 can be introduced by site-directed mutagenesis (QUIKCHANGE II XL, Stratagene).

TABLE 2

SCT constructs with zero, one, or two engineered cysteines

| | Sequence at N-terminus | Identification | Heavy chain mutation(s) |
|---|---|---|---|
| OVAp.β$_2$m.Kb construct | | | |
| SCT | SIINFEKLgggasggggs . . . | SEQ ID NO: 14 | None |
| Y84A | SIINFEKLgggasggggs . . . | SEQ ID NO: 15 | Y84A |
| T80C only | SIINFEKLgggasggggs . . . | SEQ ID NO: 16 | T80C, Y84A |
| T80C. L1C | SIINFEKLCggasggggs . . . | SEQ ID NO: 17 | T80C, Y84A |
| T80C, L2C | SIINFEKLgCgasggggs . . . | SEQ ID NO: 18 | T80C, Y84A |
| Y84C only | SIINFEKLgggasggggs . . . | SEQ ID NO: 19 | Y84C |
| Y84C, L2C (dtSCT) | SIINFEKLgCgasggggs . . . | SEQ ID NO: 20 | Y84C |
| Y84C, L3C | SIINFEKLggCasggggs . . . | SEQ ID NO: 21 | Y84C |
| Y84C, L4C | SIINFEKLgggCsggggs . . . | SEQ ID NO: 22 | Y84C |
| N86C, L5C | SIINFEKLgggaCggggs . . . | SEQ ID NO: 23 | Y84A, N86C |
| OVAp5Y, Y84A | SIINYEKLgggasggggs . . . | SEQ ID NO: 24 | Y84A |
| OVAp5Y, Y84C, L2C (dtSCT) | SIINYEKLgCgasggggs . . . | SEQ ID NO: 25 | Y84C |
| QL9.β$_2$m.Ld construct | | | |
| SCT | QLSPFPFDLgggasggggs . . . | SEQ ID NO: 26 | None |
| Y84A | QLSPFPFDLgggasggggs . . . | SEQ ID NO: 27 | Y84A |
| Y84C, L2C (dtSCT) | QLSPFPFDLgCgasggggs . . . | SEQ ID NO: 28 | Y84C |

Retroviral expression vectors pMSCV-IRES-hygromycin and pMSCV-IRES-neomycin were constructed in our lab (33) and used for concomitant expression of class I SCTs and drug resistance genes. Retrovirus-containing supernatants were generated using the Vpack vector system (Stratagene, La Jolla, Calif.) for transient transfection of 293 T cells to generate ecotropic virus for infection of 3KO and B6/WT3 cells or amphitropic virus for infection of LM1.8 cells.

In some experiments, PCR-generated inserts with appropriate DNA restriction sites flanking mature HLA-A0201 (A2) and -B2705 (B27) heavy chain sequences replaced the mature H2-Kb sequence of the previously constructed murine SCT (10) in the pIRESneo vector (Clontech Laboratories, Palo Alto, Calif.). The mature human β2m sequence was spliced into these constructs in place of the mouse β2m sequence. Thus, HLA SCTS retained the subunit order and linker lengths GGGGSGGGGSGGGGS (SEQ ID NO: 34) and GGGGSGGGGSGGGGSGGGGS (SEQ ID NO: 35) found in the original SCT design (10) (FIG. 1). Synthetic DNA oligonucleotides (Integrated DNA Technologies, Coralville, Iowa) encoding peptide antigens were ligated into the SCT vectors at restriction sites specifically designed for expeditious shuttling of peptide sequences into the SCT construct, which for this study included the melanoma G280-9V peptide (106) and human T-lymphotropic virus TAX peptide (107) for A2 and the influenza A virus NP$_{383-391}$ peptide (108) for B27. As a control, a cDNA was produced for expression of β$_2$m GGGGSGGGGSGGGGSGGGGS (SEQ ID NO: 35)-A2, with no covalently linked peptide at the N-terminus. A single point mutation (R48Q) generated by site-directed mutagenesis (QuikChange II XL, Stratagene) was required to introduce the 64-3-7 epitope (24, 37, 54-56) into A2. Two point mutations were made in the G280-9V.β2 m.A2 SCT to create the disulfide trap: a cysteine in the second position of the first linker and a cysteine at position 84 of the A2 heavy chain. DNA sequencing confirmed the correct sequence of all constructs.

SCT Expression and Purification—The SCT constructs (FIG. 7) were expressed separately in the bacterial strain BL21CodonPlus® (DE3)RIL (Stratagene, La Jolla Calif.) and insoluble inclusion bodies were prepared as previously described (91). The purified, detergent-free, inclusion bodies were solubilized overnight, in 6 M Gdn.HCl, 10 mM Tris pH 8.0, and 10mM □-mercaptoethanol. To form the SCT proteins, the inclusion bodies were refolded under oxidative conditions. Refolding was performed at 4° C. using a rapid dilution method. Briefly, each of the SCT proteins (final concentration 1.5 µM) was injected in five separate batches spaced over an 8-hour period into 500 ml of refolding buffer (100 mM Tris pH 8.0, 400 mM L-Arg, 2.0 mM EDTA, 0.5 mM GSSG, 5.0 mM GSH, and protease inhibitors). The final concentration of Gdn.HCl in the refolding reaction did not exceed 100 mM. After an overnight incubation the refolding reaction was concentrated to 4 ml using an Amicon ultrafiltration device (Millipore, Billerica Mass.).

The formed SCT proteins were purified on a Superdex75 (Pharmacia, Piscataway N.J.) size exclusion column using a running buffer containing 20 mM HEPES pH 7.5, 150 mM NaCl, and 0.01% NaN$_3$. The fractions containing the refolded proteins were pooled, diluted threefold in buffer containing 20 mM Tris pH 8.5, loaded on an anion exchange MonoQ column (Pharmacia, Piscataway N.J.), and eluted with a NaCl gradient (0 mM to 400 mM NaCl over 30 ml). Prior to crystallization the purified SCT proteins were exchanged in buffer containing 20 mM HEPES pH 7.5, and 20 mM NaCl. Typically 800 μg of purified complex were obtained from a 500 ml refolding reaction.

Flow Cytometry—Viable cells, gated by forward and side scatter, were analyzed on a FACSCalibur (BD Biosciences), and data (10,000 events per sample) were analyzed using CELLQUEST software (BD Biosciences). Staining with anti-class I mAbs was visualized using phycoerythrin-conjugated goat anti-mouse IgG (BD Biosciences). Soluble, recombinant m6α T cell receptor (TCR) was used for flow cytometry directly from the supernatant of insect cells (34-36). Secondary reagents used to detect binding of the m6α TCR included biotinylated anti-mouse TCR β chain monoclonal antibody H57 (BD Biosciences) and phycoerythrin-conjugated streptavidin (BD Biosciences). In some experiments, Flow cytometric analyses were performed using a FACSCALIBUR (BD Biosciences, San Jose, Calif.). Dead cells and debris were excluded from analysis on the basis of forward-angle and side-scatter light gating. A minimum of 10,000 gated events was collected for analysis. Data were analyzed using CELLQUEST software (BD Biosciences). For surface staining, $5 \times 10^5$ cells per sample were incubated on ice in microtiter plates with culture supernatant from the appropriate hybridoma. After washing, PE-conjugated goat anti-mouse IgG (BD Pharmingen, San Diego, Calif.) was used to visualize class I staining. In some experiments, flow cytometry followed incubation ($1 \times 10^6$ cells/mL) with exogenous peptides TAX (A2-specific) (107) or MCMV (H2-Ldspecific) (32) at indicated concentrations.

Immunoprecipitation and Western blotting—Immunoprecipitations were performed essentially as described previously (20). Briefly, cells were treated with 1.0% NP-40 (IG-EPAL CA-630, Sigma) lysis buffer including 20 mM iodoacetamide and protease inhibitors. Postnuclear lysates were mixed with EDS sample buffer (Invitrogen), and 2-mercaptoethanol (Sigma) was either added to a final concentration of 1%, or excluded for nonreducing gels. Western blotting was performed after SDS-PAGE separation of precipitated proteins as described previously (37), Rabbit serum for blotting $K^b$ was generated in our lab by peptide immunization using an amino acid sequence from the cytoplasmic tail of Kb. Biotin-conjugated donkey anti-rabbit IgG (Jackson Immunoresearch) was used as a secondary staining reagent followed by streptavidin-horseradish peroxidase (Zymed Laboratories). Specific proteins were visualized by chemiluminescence with the ECL System (Amersham Biosciences). In some experiments. Cells were lysed in PBS+ 1.0% NP-40 (Sigma, St. Louis, Mo.), 20 mM iodoacetamide, protease inhibitors, and a saturating concentration of precipitating mAb. After lysis for 30 min on ice, post nuclear lysates were incubated with protein A-Sepharose (Amersham Pharmacia Biotech, Uppsala, Sweden) for 1 h. Beads were washed four times in PBS+0.1% detergent, and bound proteins were eluted by boiling in 1×SDS-PAGE sample buffer. For nonreducing gels, 2-ME was excluded. For some samples, endoglycosidase H treatment followed immunoprecipitation. Bound proteins were eluted from protein A-Sepharose by boiling in 10 mM TrisCl, pH 6.8+0.5% SDS+1% 2-ME. Eluates were mixed with an equal volume of 100 mM sodium acetate, pH 5.4, and either digested (or mock-digested) at 37° C. for >1 h with 1 mU endoglycosidase H (ICN Pharmaceuticals. Costa Mesa, Calif.) that was reconstituted in 50 mM sodium acetate, pH 5.4. In some experiments, Immunoblotting was performed following SDS-PAGE separation of precipitated proteins and transfer to Immobilon P membranes (Millipore, Bedford, Mass.). Membranes were blocked (1 h to overnight) with PBS+10% dried milk+0.05% Tween 20. Primary Abs were added and incubated for 1 h, followed by washing in PBS+0.05% Tween 20. As a second step, membranes were incubated for 1 h with biotin-conjugated anti-mouse Ig (Caltag Laboratories, San Francisco, Calif.). In some cases, biotin-conjugated mAb 64-3-7 was used, which obviated the second step. After washing, HRP-conjugated streptavidin (Zymed Laboratories) was added for 1 h, followed by three washes. Specific proteins were visualized by chemiluminescence using the ECL system (Amersham, Boston, Mass.).

CTL assays—LM1.8 target cells transduced with the indicated class I constructs were incubated with or without 10 μM exogenous peptide and then labeled with $Na^{51}CrO_4$ for 1 hour. OT-1 or 2C T cells were plated at various concentrations onto 96-well microtiter plates and incubated with target cells for 4 h at 37° C. in 5% $CO_2$. Radioactivity in supernatants was measured in an Isomedic γ-counter (ICN Biomedicals). The mean of triplicate samples was calculated, and percentage $^{51}Cr$ release was determined as follows: % $^{51}Cr$ release=100× ((experimental $^{51}Cr$ release−control $^{51}Cr$ release)/(maximum $^{51}Cr$ release−control $^{51}Cr$ release)), where experimental $^{51}Cr$ release represents counts from target cells mixed with effector cells, control $^{51}Cr$ release represents counts from target cells in medium alone, and maximum $^{51}Cr$ release represents counts from target cells lysed with 5% (v/v) Triton X-100 (Sigma).

In some experiments, HeLa cell targets expressing A2 and B27 SCTs were tested against specific CTL lines. Protocols for the generation of CTLs and chromium-release assays to measure specific lysis have been described (112). The RR10 CTL was generated from a patient immunized with G280-9V pulsed DC as described (113). A CMV pp65-specific CTL line was generated from a CMV seropositive healthy donor using purified CD8+ T cells, peptide-pulsed irradiated autologous DC, and 10 U/mL IL-2 added on day 2. Primed CD8+ T cells were repeatedly stimulated with antigen to generate CTL lines. Peptide competition assays were performed by incubating targets with competitor peptide at the indicated concentrations. On the following day, targets were trypsinized, washed twice, and used in a standard chromium release assay.

N15 hybridoma assays—The TCR⁻ murine T cell hybridoma 58α⁻β⁻ (38) transfected with the α and β chains for the N15 TCR was obtained from Dr. Hsiu-Ching Chang (Dana-Farber Cancer Institute, Harvard Medical School). This cell line is also transfected with CD3ζ and CD8αβ cDNAs to optimize TCR expression and recognition of class I (39). Biological activity of IL-2 secreted by the M15 hybridoma was used to detect Kb/VSV8 complexes.

In some experiments, B6/WT3 cells or 3KO cells ($5 \times 10^4$/ 200 μl/well) expressing endogenous Kb or Kb SCT constructs were incubated for 1 hour at 37° C. with the indicated concentrations of VSV8 peptide in a flat-bottom 96-well plate. The cells were washed, fixed in 1% paraformaldehyde for 15 minutes at room temperature, then washed again. The N15 hybridoma cells ($10^5$/200 μl/well) in fresh media were then added to the plate and cultured for 24 hours. Supernatants were harvested and frozen at −80° C. for at least 1 hour to lyse trace cells that may have carried over. CTLL-2 cells were washed and added to supernatants at a final cell density of $10^4$/200 μl/well in a 96-well plate. After 18-24 h of incubation, Alamar blue (BioSource International) was added at 20 μl/well, and relative amounts of IL-2 in each supernatant were determined by fluorescence on a multi-detection microplate reader (Bio-Tek Instruments).

In some experiments, LM1.8 cells ($2\times10^4$/200 μL/well) expressing native $K^b$ or the SCT constructs were incubated for 24 hours in a 96-well plate with N15 hybridoma cells ($2\times10^5$/200 μL/well) in the continuous presence of the indicated concentrations of VSV8 (RGYVYQGL) (SEQ ID NO: 31) peptide. Supernatants were harvested and frozen at −80° C. for at least 1 hour to lyse trace cells that may have carried over. CTLL-2 cells were washed and added to supernatants at a final cell density of $5\times10^3$/200 μL/well in a 96-well plate. Triplicate wells were run for each sample. After 18-24 hours of incubation, Almar blue (BioSource International, Camarillo Calif.) was added at 20 μL/well, and relative amounts of 1L-2 in each supernatant were determined by fluorescence in a multi-detection microplate reader (Bio-Tek Instruments, Winooski Vt.).

Thermal Denaturation Studies Purified SCT proteins were dialyzed against 10 mM $K_2HPO_4$/$KHPO_4$ buffer pH=7.5, and 150 mM. NaCl. Protein concentration was determined by absorption at 280 nm of denatured protein in buffer containing 8M Urea, 25 mM $K_2HPO_4$/$KHPO_4$, pH=7.5. SCT proteins were diluted to 475 nM in 20 mM $K_2HPO_4$/$KHPO_4$ buffer pH=7.5, and 150 mM NaCl. CD spectra at 10° C. were collected between 260 and 200 nm at 0.5 nm increments on Jasco-810 instrument equipped with Peltier temperature controller using 1-cm path-length cuvettes. Four spectra were averaged for the final spectrum of each sample. The thermal denaturation profiles for each SCT protein and native H2$K^b$-Ova were monitored by the change in CD signal at 220 nm as a function of temperature. Thermal scan data were collected at a 1.0° C. interval from 10 to 70° C. with a temperature ramp rate at 50° C./hour. All measurements were made at least four times and averaged. Thermal denaturation curves were scaled from 0% to 100% to provide plots of the percent of signal change versus temperature. The $T_{1/2}$ is the temperature at which the CD signal change is half of the total signal change.

Crystallization and Data Collection—Diffraction-quality crystals of each of the SCT proteins were obtained by hanging-drop, vapor-diffusion method. Protein at 6 to 8 mg/ml was equilibrated at 20° C. against 13% (w:v) PEG 10,000 and 100 mM MES pH 6.2 for $SCT^{WT}$; 14% PEG 6,000 and 1.00 mM MES pH 6.4 for $SCT^{Y84A}$; 13% PEG 6,000 and 100 mM MES pH 6.3 for $SCT^{Y84C-PBL2C}$. Small crystals obtained in these drops were used to microseed protein hanging drops equilibrated against similar conditions with marginally lower concentrations of PEG. Larger crystals appeared overnight and grew over three to four weeks. Just prior to data collection, crystals were briefly soaked in crystallization buffer to which Ethylene Glycol was added to a final concentration of 20% (v:v) as cryoprotectant for liquid nitrogen flash cooling. X-ray diffraction data for each SCT crystal were collected on the ID-19 beamline at APS. A total of 360 frames were collected for each SCT crystal each frame representing a 1.0° oscillation range. These data were indexed and integrated using DENZO (HKL Suite, HKL Research, Inc., Charlottesville Va.) in the primitive monoclinic lattice for all SCT proteins with nearly identical cell dimensions (Table 3), and scaled and merged using SCALEPACK (HKL Suite, HKL Research, Inc., Charlottesville Va.). Wilson scaling was applied to the final output structure factor amplitudes [Collaborative Computing Project 4 (CCP4), Daresbury Laboratory, Warrington UK (92)].

Structure Determination and Refinement—Initial phase estimates for each SCT protein were obtained by rigid body refinement of the atomic coordinates of H-2$K^{bm8}$ (PDB 1RJY) against each of the data sets. Extensive model building was performed with the macromolecular modeling program O (O version 6.22, Uppsala Software Factory, Sweden) using $2F_O F_C$, $F_O$-$F_C$, and $2F_O$-$F_C$ composite omit maps [CMS, Yale University, New Haven Conn. (93)]. Atomic refinement was done employing simulated annealing, energy minimization, and restrained B-factor refinement protocols as implemented in CNS and CCP4. Refinement statistics of the final models are listed in Table 3.

Computational Analysis—Graphical structure representations were primarily created using Ribbons (94). Molecular surfaces of the peptide-binding grooves were generated using InsightII (Biosym Technologies, San Diego Calif.). Superpositions and r.m.s.d. calculations between the different MHC proteins were obtained using Lsqkab (CCP4). R.m.s.d. values between the aligned peptide main chain, and side chain atoms were calculated using CNS (93). HBPLUS (95) was used to catalogue contacting atoms and putative hydrogen bonds.

OT-1 CTL assays—LM1.8 target cells transfected with the indicated constructs were incubated with or without 10 μM exogenous peptide and then labeled with $Na^{51}CrO_4$ for an hour. OT-1 cells were plated at various concentrations onto 96-well microliter plates and incubated with target cells for 4 hours at 37° C. In 5% $CO_2$. Radioactivity in supernatants was measured in an Isomedic γ-counter (ICN Biomedicals, Costa Mesa Calif.). The mean of triplicate samples was calculated, and percentage of $^{51}Cr$ release was calculated as follows: % of $^{51}Cr$ release=100×(experimental $^{51}Cr$ release−control $^{51}Cr$ release)÷(maximum $^{51}Cr$ release−control $^{51}Cr$ release). Experimental $^{51}Cr$ release represents counts from target cells mixed with effector cells, control $^{51}Cr$ release represents counts from target cells in medium alone, and maximum $^{51}Cr$ release, represents counts from target cells lysed with 5% (v:v) Triton X-100 (Sigma. St. Louis Mo.)

Tetramer construction—Peptides SIINFEKL (SEQ ID NO: 29) and SIINFEKLGC (SEQ ID NO: 37) were used for H-2$K^b$ and H-2$K^{bY84C}$ heavy chains respectively. Irrelevant $K^b$ peptide SIYRYYGL (SEQ ID NO: 30) (27) was used for construction of negative control H-2Kb tetramers. Peptides were obtained commercially (EZBiolab Inc, Westfield Ind.) or synthesized on an Applied Biosystems Model 432A peptide synthesizer. The BirA biotinylation sequence was included at the C-terminus of the H-2$K^b$ ectodomain. In addition, H-2$K^b$ and H-2$K^{bY84C}$ tetramer constructs included the mutation C121S, which removes the unpaired cysteine of $K^b$ and thus simplifies its refolding and purification with disulfide-trapped peptide. Refolding and purification were performed as described above. At this point, samples were submitted for mass spectrometric analysis to confirm integrity and identity of the recombinant MHC molecules. Biotinylation with BirA ligase was carried out overnight at ambient temperature according to the manufacturer's instructions (Avidity, Boulder Colo.). To remove free biotin, MHC molecules were again purified by SEC, then tetramerized by addition of fluorochrome-conjugated streptavidin at a molar ratio of 4 molecules of MHC to 1 molecule of either phycoerythrin-(PE-)streptavidin or allophycocyanin-(APC-)streptavidin (both from BD Biosciences, San Jose Calif.). The MHC concentration of all stock tetramer preparations was 4.3±0.2 and tetramers were used at identical dilutions for staining experiments. The specificity of each of the tetramers was confirmed using positive-control transgenic T cells.

Infection of mice with *Listeria* and tetramer staining—B6 mice were infected by tail vein injection of $5\times10^3$ cfu of *Listeria monocytogenes* expressing ovalbumin (L.m.-Ova, a kind gift of Hao Shen, University of Pennsylvania) in a volume of 200 μL pyrogen-free saline. After 7 days, splenocytes were harvested and red blood cells lysed. Splenocytes were stained with the indicated tetramers for 30 minutes on ice, then with FITC-conjugated anti-CD8 (BD Biosciences) for 20 minutes. Propidium iodide staining was used to exclude dead cells. Splenocytes were also prepared from (uninfected) OT-1 transgenic mice and stained in the same manner. Cells were analyzed on a FACSCALIBUR (BD Biosciences), and data were analyzed using CELLQUEST software (BD Biosciences). More than 15,000 CD8+ events were collected per staining in order to reliably determine the frequency of tetramer-positive CD8 cells.

Example 1

This example illustrates disulfide bond engineering strategy.

As in our previous characterization of SCT molecules (10, 11), we again chose the Kb/OVA system, for which there are excellent reagents to monitor both MHC conformation and peptide occupancy (24, 40). Our approach was to introduce cysteine residues by site-directed mutagenesis, one in the heavy chain of Kb and one in the first linker (FIG. 1A), which extends from the C-terminus of the SIINFEKL (SEQ ID NO: 29) peptide to the N-terminus of mature β2-microglobulin ($\beta_2$m). Placing the second cysteine in the linker, rather than within the peptide itself, we hypothesized would minimize perturbations to the MHC/peptide conformation and also allow us to more readily translate this disulfide bonding approach to SCT constructs based on other MHC/peptide complexes.

To select the exact positions for cysteine mutations, we superimposed the crystal structures of Kb/OVA (41) and the MHC class II molecule 1-Ek bound to a hemoglobin peptide ($Hb_{64-76}$) (42). This latter structure features the $Hb_{64-76}$ peptide covalently attached with a Gly-Ser linker to the β chain of class II (43, 44). The linker extends from the open class II groove from the C-terminal residue of the $Hb_{64-76}$ peptide. Thus, overlaying these structures provided a framework for determining distances between Kb heavy chain residues and specific positions along the first SCT linker (FIG. 1B). Three residues on the Kb heavy chain were selected for substitution of a cysteine residue: Thr80, Tyr84, and Asn86. Importantly, the Y84A heavy chain mutation was also incorporated into the SCTs with the T80C and A86C mutations, since we previously found that the Y84A mutation allowed for better linker accommodation (11). Based on the superimposition shown in FIG. 1B, the locations for various Sinker cysteine residues were selected. Thus several constructs were made and tested for potential disulfide bond formation to trap the peptide into the class I binding groove (Table 2). To control for the consequences of having an unpaired cysteine, SCT mutants with single cysteine mutations at the three above mentioned heavy chain positions were also constructed.

Example 2

This example illustrates characterization of SCT cysteine variants

Figure 2A:
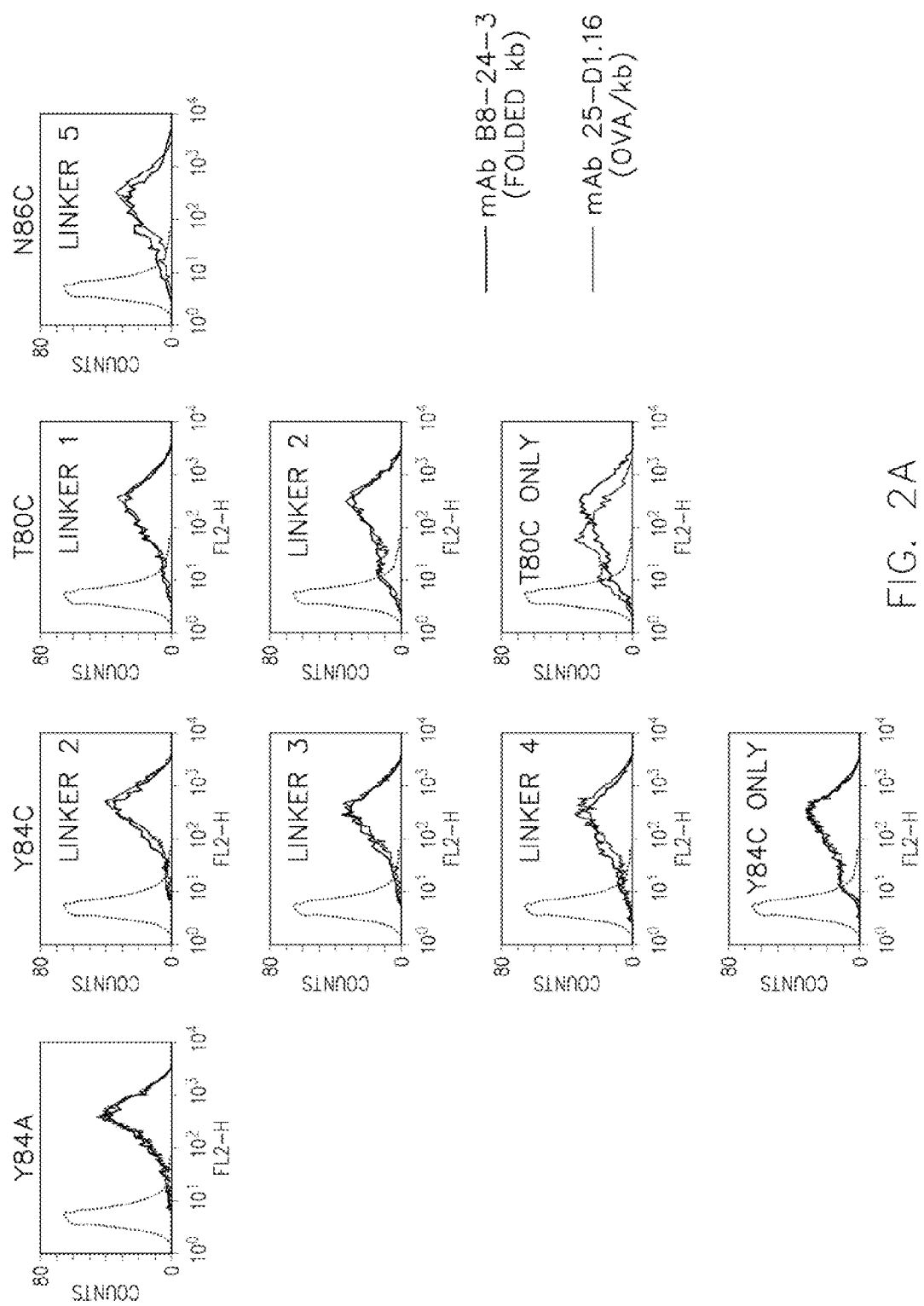
FIG. 2. A, Cell surface expression of single chain trimer (SCT) OVA.β$_2$m.Kb constructs with and without cysteine mutations. Fibroblasts derived from mice deficient in β$_2$m, Kb, and Db (3KO cells) were transduced with constructs mutated at specific positions along the class I heavy chain (columns) and/or along the first Gly-Ser linker of the SCT (rows). See Table 2. The cells were stained with antibodies to Kb (mAb B8-24-3, thin black line), the Kb/OVA complex (mAb 25-D1.16, thick gray line), or secondary antibody alone (dotted line) and analyzed by flow cytometry. B, Migration of OVA.β$_2$m.Kb constructs with and without cysteine mutations in during non-reducing SDS-PAGE. 3KO cells expressing the indicated OVA.β$_2$m.Kb SCT cysteine mutants were lysed and immunoprecipitated with an antibody to Kb (mAb B8-24-3). These samples were reduced or not reduced and subjected to SDS-PAGE, Western blotting with rabbit serum specific for Kb revealed the migration pattern of the SCTs, Faster migration in the non-reducing gel indicated the formation of an additional disulfide bond.

Retroviral transduction was used to introduce each of the SCT variants into $Kb^{-/-}$ $Db^{-/-}$ $\beta_2m^{-/-}$ (3KO) fibroblasts (20). This permitted the unambiguous analysis of the transduced class I constructs. Cell surface expression of SCTs with disulfide traps was also confirmed in wildtype cells (see FIG. 5). All of the SCT cysteine variants were detected at the cell surface by flow cytometry (FIG. 2A) both with mAb B8-24-3, which detects folded, peptide-occupied Kb, and with mAb 25-D1.16, which binds specifically to the Kb/OVA complex (24). $K^b$-reactive mAb Y3 also recognized the SCT variants. The engineered molecules were expressed at high levels similar to the control SCT Y84A, suggesting that they had folded properly in the ER, passed BR quality control mechanisms, and efficiently transited to the cell surface. The level of staining with the Kb/OVA-specific antibody was constant relative to the amount of folded Kb with the exception of the control SCT variant T80C. The mAb 25-D1.16 is known to bind near the C-terminus of the peptide (45), and thus the unpaired cysteine or the loss of threonine at position 80 could impair mAb 25-D1.16 detection of this variant SCT. However, when the T80C heavy chain mutation was combined with a cysteine mutation in the linker, efficient recognition by mAb 25-D1.16 was restored. The comparable detection of the other variant SCTs with mAbs 25-D1.16 and B8-24-3 suggests that the introduction of cysteines at these various locations in the SCT spacer and/or heavy chain had no significant impact on the conformation of the MHC/peptide complex detected by mAb 25-D1.16.

Our next objective was to determine biochemically which constructs actually had the additional disulfide bond, for it was unknown a priori how engineered cysteine residues would interact with ER thioreductases (46-48). In non-reducing SDS-PAGE, the presence of disulfide bonds can reduce the radius of gyration of denatured proteins, causing them to migrate faster through the gel matrix. Thus the variant OVA.$\beta_2$m.Kb SCT constructs were compared in reduced vs. non-reduced SDS-PAGE gels (FIG. 2B). As expected, all of the constructs migrated the same distance when the samples were reduced with β-mercaptoethanol. (One exception is the N86C, L5C mutant in lane 9, which migrates faster than the other mutants because it no longer has its N-linked glycan.) However, in the non-reducing gel, each of the constructs with engineered paired cysteines (lanes 2, 3, 4, 6, 7, and 9) migrated faster than their counterparts with either zero or one additional cysteine. These observations provide biochemical evidence that the cells had formed a disulfide bond between the introduced cysteines in each of these six constructs. The oxidation appeared to be complete, as reduced forms were not observed. Post-lysis formation of disulfide bonds is not likely to account for these results, since the sulfhydryl-reactive compound iodoacetamide was included in the sample preparation. The observation that cysteines at different linker locations formed disulfide bonds with the same heavy chain residues (Y84C and T80C) was probably a reflection of the flexibility of the Gly-Ser linker.

For a number of reasons, we focused our subsequent analyses on the Y84C, L2C disulfide bond position. First of all, we had previously engineered position 84 in the SCT heavy chain, and T cells recognized the Y84A mutant of the SCT, perhaps even more efficiently (11). Secondly, position 84 is highly conserved, increasing the likelihood that engineering at that position would easily transfer to other class I molecules (see FIGS. 5 and 6). Furthermore, it was anticipated that placement of a disulfide bond at position 84 would substitute for hydrogen bonding between the C-terminus of the peptide and Y84 in the F pocket of native class I molecules. We chose the second linker position (L2C) downstream of the SCT peptide to match with Y84C, reasoning that a disulfide bond closer to the SCT peptide would provide the best anchor. Thus the Y84C, L2C construct was chosen for further study and designated the disulfide-trap single-chain trimer, or dtSCT.

Example 3

This example illustrates design of some HLA SCT molecules.

In some experiments, three different SCTs were used, each with disease relevance. The first SCT was constructed with the peptide, G280-9V (YLEPGPVTV) (SEQ ID NO: 5), bound to A2. This peptide is derived from the melanocyte-specific gp100 protein, which is expressed in most melanomas (106, 114). Adoptive transfer of cultured tumor-infiltrating lymphocytes specific for gp100 has been shown to cause tumor regression (90). The second SCT was constructed with the peptide, TAX (LLFGYPVYV) (SEQ ID NO: 6) also bound to A2. This peptide is derived from p40tax protein, the major antigenic protein of the human T-cell leukemia virus (HTLV), which causes adult T-cell leukemia (107, 115). The third SCT was constructed with the peptide, NP383-391, (SRYWAIRTR) (SEQ ID NO: 12) bound to B27, and is a fragment of the influenza A nucleoprotein (108). These antigens were chosen for their predominant roles in CTL responses to melanoma, HTLV, or influenza, respectively. However, the HLA-B27 allele is also of interest due to its association with arthritic disease (116). SCTs were constructed for each of these peptide/MHC complexes to test efficiency of cell surface expression, folding of the molecules (by monitoring conformational changes serologically), and T cell recognition.

Example 4

Figure 13A:
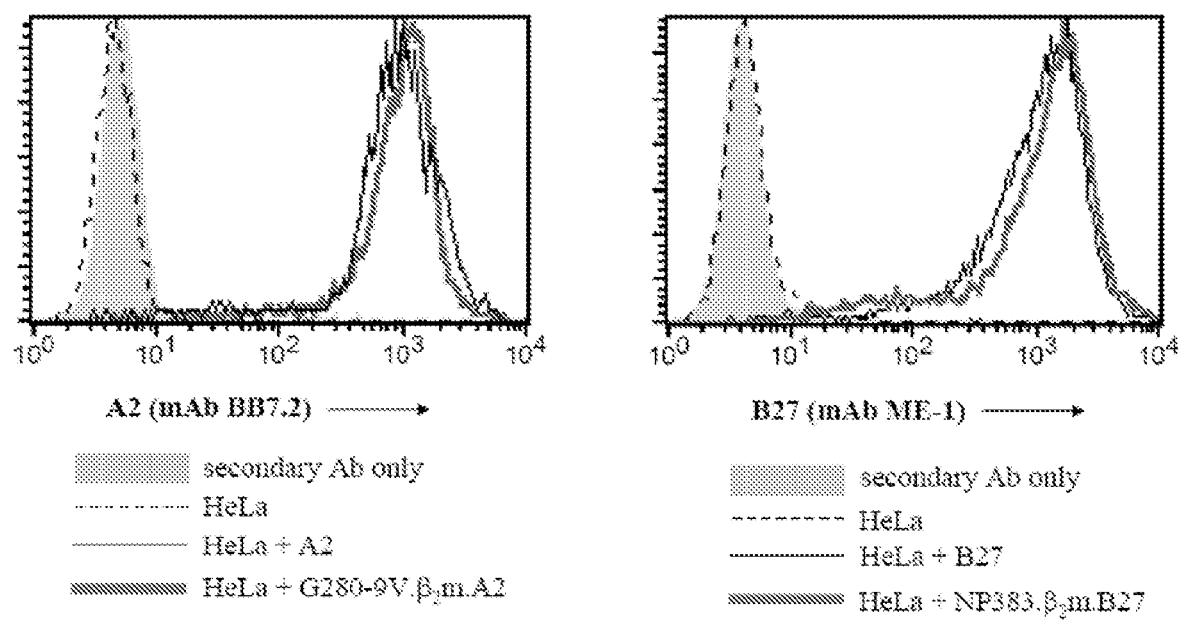
FIG. 13. Efficient cell surface expression, biochemical stability, and T cell recognition of HLA-A2 and HLA-B27 SCTs. (a) Flow cytometry of stable HeLa transfectants stained with mAbs specific for either HLA-A2 (mAb BB7.2) or HLA-B27 (mAb ME-1). Surface staining is shown for SCTs (thick gray lines), native class I molecules (thin black lines), untransfected HeLa cells (dotted lines), and for secondary reagent staining only (gray-filled histograms), (b) HLA-B27 and the NP383-391.β2m.B27 SCT, both 64-3-7 epitope-tagged, were immunoprecipitated from HeLa cell lysates using either mAb ME-1, specific for folded B27, or mAb 64-3-7, specific for open MHC conformers. The immunoprecipitates were digested or mock-digested with endoglycosidase H, as were post-nuclear cell lysates. Immunoblots detected the molecular weights, folding, and the EndoH sensitivity of the transfected molecules, (c) HeLa cells transfected with the indicated A2 constructs were lysed and immunoprecipitated using mAb BB7.2, specific for folded HLA-A2. Samples were digested or mock-digested with endoglycosidase H. Immunoblots using mAb HCA2 revealed the biochemical integrity and EndoH resistance of the A2 SCTs (left panel). Densitometry using NIH Image revealed that 99% of the A2 SCTs remain intact, while 1% of the signal was found in a fragment at ~40 kD. The gel migration of the A2 SCT was also directly compared with that of a $\beta_2$m.A2 covalently linked dimer (right panel) to demonstrate that the antigenic peptide and first SCT linker are not cleaved by cellular proteases, (d) CTL recognition of the NP383-391.$\beta_2$m.B27SCT. Target cells transfected with either native B27 or the B27 SCT were incubated with NP383-391./B27-specific CTL effectors. The SCT was strongly recognized without the addition of exogenous peptide, (e) CTL recognition of the TAX.$\beta_2$m.A2SCT and its susceptibility to peptide competition. Two distinct TAX/A2-specific CTL lines recognized the TAX.$\beta_2$m.A2SCT, but it was not recognized by the pp65/A2-restricted T cell line. However, when increasing concentrations of competitor peptide pp65 were added to the SCT-expressing target cells, significant lysis was detected.
Figure 15:
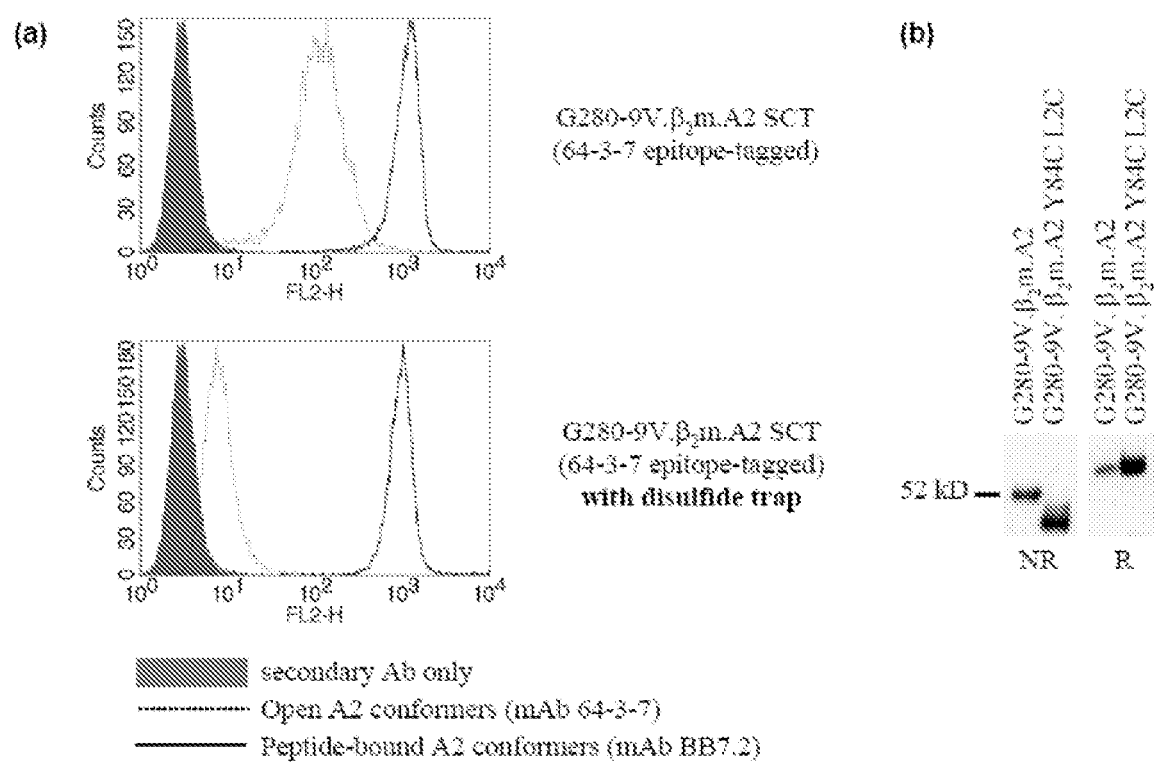
FIG. 15. Introduction of a disulfide trap into the HLA-A2 SCT. (a) Cells expressing the G280-9V.$\beta_2$m.A2 SCT (upper panel) or the same construct engineered with the disulfide trap (lower panel) were stained with antibodies specific for folded A2 (BB7.2, thin black line) or open A2 conformers (64-3-7, thin dotted line, see FIG. 3). Negative control staining is also shown (gray histogram). Addition of the disulfide trap resulted in a dramatic decrease in open conformers (~10-fold) detected at the cell surface, (b) Biochemical confirmation of cysteine residue oxidation. The same cell lines were lysed and A2 SCTs were immunoprecipitated and subjected to SDS-PAGE under non-reducing (NR) or reducing (R) conditions. The additional disulfide bond contracts the radius of gyration of the denatured molecule, allowing it to migrate faster through the gel matrix.

This example illustrates efficient folding, cell surface expression, and T cell recognition of HLA SCTs In these experiments, HeLa cells were transfected with native HLA heavy chains or SCTs of the complexes A2/G280-9V, A2/TAX or B27/$NP_{383-391}$. The SCT constructs exhibited high-level surface expression, comparable to the native HLA molecules, as detected in flow cytometry experiments using mABs specific for the respective folded HLA molecules (FIG. 13a, see also FIG. 15). Thus, these HLA SCTs passed ER qualify control, and linkers were accommodated such that the proper HLA folding was detected by mABs specific for the native, fully assembled HLA molecules. It is noteworthy that a construct similar to our G280-9V.$\beta_2$m.A2 SCT was expressed as a recombinant protein (103); however, for certain applications, such as DNA vaccination (117, 118) it was critical to verify cell surface expression in mammalian cells where the SCT faces competition with endogenous β2m, peptides, and molecular chaperones.

Example 5

This example illustrates the level of steady-state fldig of the HLA SCTs.

Figure 13B:
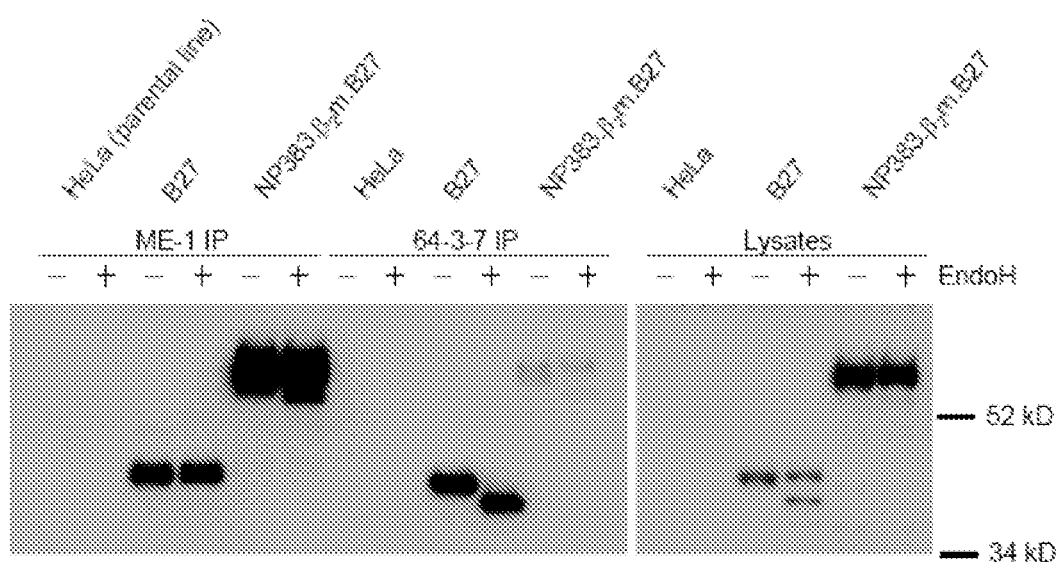
Figure 13C:
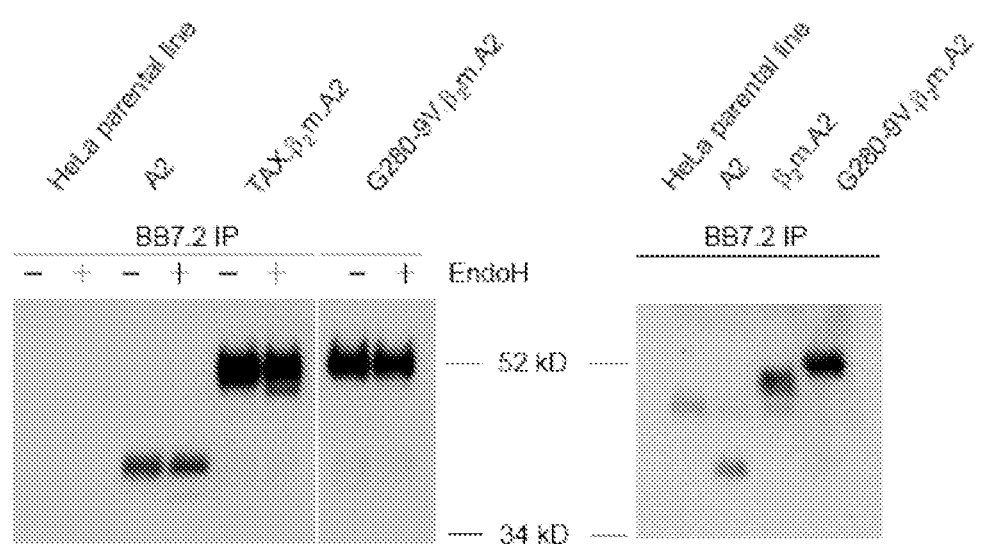

In these experiments, to quantify the amount of open MHC conformers, the 64-3-7 epitope tag was introduced into both native B27 and the NP383-391.β2m.B27 SCT (25, 37, 54-56). HeLa cells expressing these constructs were lysed and analyzed by immunoprecipitation and blotting (FIG. 13b, left panel). Almost all of the B27 SCT was folded (ME-1+) and mature (EndoH-resistant) at steady-state. Very few peptide-empty (64-3-7+) forms of the HLA-B27SCT were detected, indicating that these SCTs fold rapidly. In contrast, native B27 molecules had approximately equal amounts of folded and open conformers, and all of the open conformers were immature (Endo H-sensitive). Furthermore, these immunoblots confirmed that the covalent [$G_4S$]$_3$ and [$G_4S$]$_4$ linkers remained intact when the NP383-391.$\beta_2$m.B27 SCT was expressed in cells, as indicated by the absence of proteolytic fragments in both immunoprecipitates (FIG. 13b, left panel) and lysates (FIG. 13b, right panel). Similarly, efficient maturation and intact covalent structure was also apparent in HeLa cells expressing either the TAX.$\beta_2$m.A2 or G280-9V.$\beta_2$m.A2 SCT (FIG. 13c, left panel). The vast majority of each SCT was EndoH-resistant, indicating rapid maturation, and each SCT was full-length, indicating lack of proteolytic digestion.

Example 6

This example illustrates that the SCT peptide moieties are not proteolytically cleaved and "re-presented" in the context of the HLA SCT binding groove.

In these experiments, we found that the G280-9V.$\beta_2$m.A2 SCT migrated more slowly than the $\beta_2$m.A2 covalently linked dimer when analyzed by immunoprecipitation and blotting, (FIG. 13c, right panel). The antigenic peptide and first linker conferred upon the SCT a higher molecular weight. These observations provide direct biochemical evidence of the intact nature of the A2 SCT.

Example 7

This example illustrates that HLA SCTS are recognized by cytotoxic T cells specific for these clinically relevant HLA complexes.

Figure 13D:
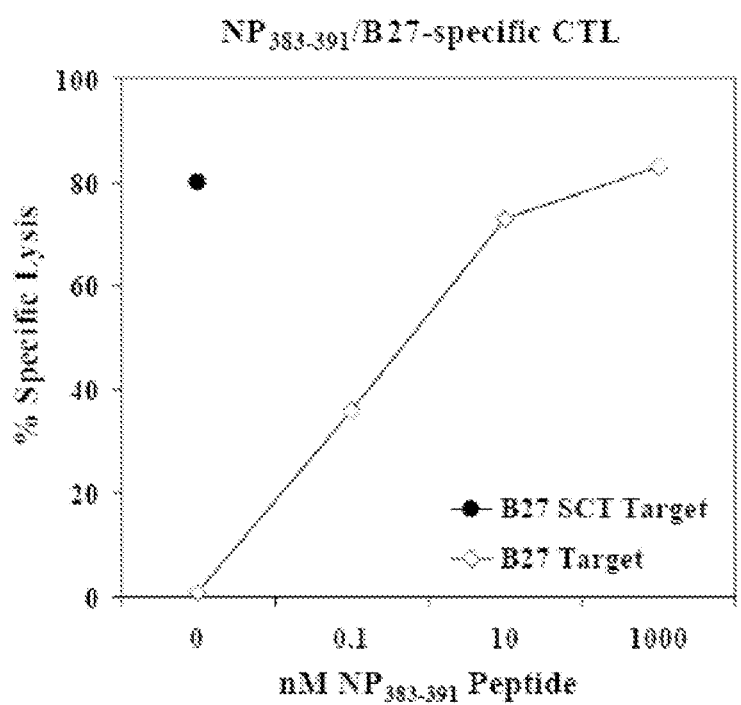
Figure 13E:
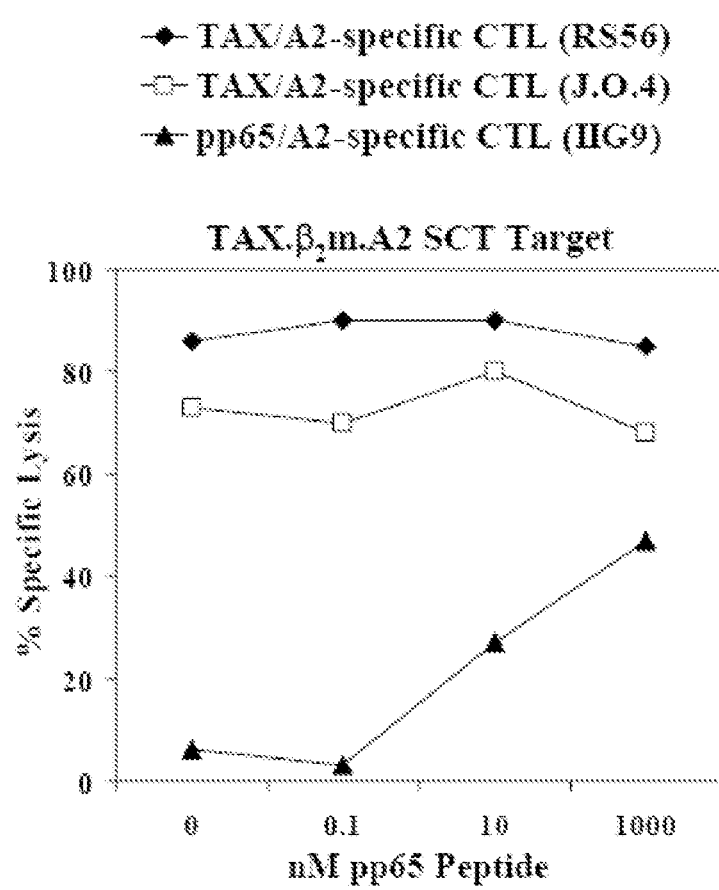

In these experiments, targets expressing the $NP_{383-391}$.β2m.B27 SCT (FIG. 13d), TAX.$\beta_2$m.A2SCT (FIG. 13e), and G280-9V.$\beta_2$m.A2 SCT (FIG. 16a) were lysed specifically by T cells originally stimulated by APC expressing the native HLA complexes. As expected, the SCTs were not recognized by T cells specific for other peptide antigens that bind to A2 or B27 (FIGS. 13e and 16b). In summary, these clinically relevant A2 and B27 SCTs were highly expressed, intact, and recognized by T cells. In fact, each human MHC/peptide combination covalently linked in the SCT configuration (see Table 4) has engaged T cells specific for the corresponding native MHC complexes. This strongly argues that the SCT linkers are essentially transparent to T cells. Our previous work in the mouse system has further demonstrated that SCT linkers also allow for binding of the CD8 co-receptor (119) and NK receptor Ly49C (0.17). These cumulative findings validate the use of SCTs in basic immunological research as well as clinical studies of vaccines and immunotherapy.

Example 8

This example illustrates that HLA SCTs are susceptible to peptide exchange.

In these experiments, we first measured the ability of the TAX.$\beta_2$m. A2SCT to exclude a competitor peptide with comparable affinity for A2. Increasing concentrations of the CMV pp65 peptide were incubated with TAX.$\beta_2$m.A2SCT-expressing targets, which were then subjected to a cytotoxicity assay using TAX- or pp65-specific CTLs (FIG. 13e). The addition of competitor peptide did not significantly decrease the ability of TAX-specific T cells to recognize the SCT; however, pp65-specific T cells did recognize the SCT to a certain extent after incubation with pp65 peptide. Since the target cells themselves did not express A2 endogenously, it was clear that the pp65 peptide was accessing the peptide-binding groove of the A2 SCT.

Example 9

This example illustrates serological and biochemical analyses of disulfide-trap HLA SCT.

In these experiments, mAb 64-3-7 was used to monitor the peptide binding state of MHC class I molecules serologically. This mAb defects a peptide-empty or "open" conformation of class I heavy chains that bear the appropriate epitope for this reagent (25, 37, 54-56). The conserved sequence recognized by 64-3-7 is naturally found in H2-L$^d$, but a single point mutation (R48Q) was all that was required to recreate the 64-3-7 epitope in HLA-A2. We tested the functionality of the 64-3-7 epitope in HeLa cells expressing the β2m.A2 dimer with the intent to use this approach later to measure the open conformers of A2 SCTs with and without the disulfide trap.

Figure 14:
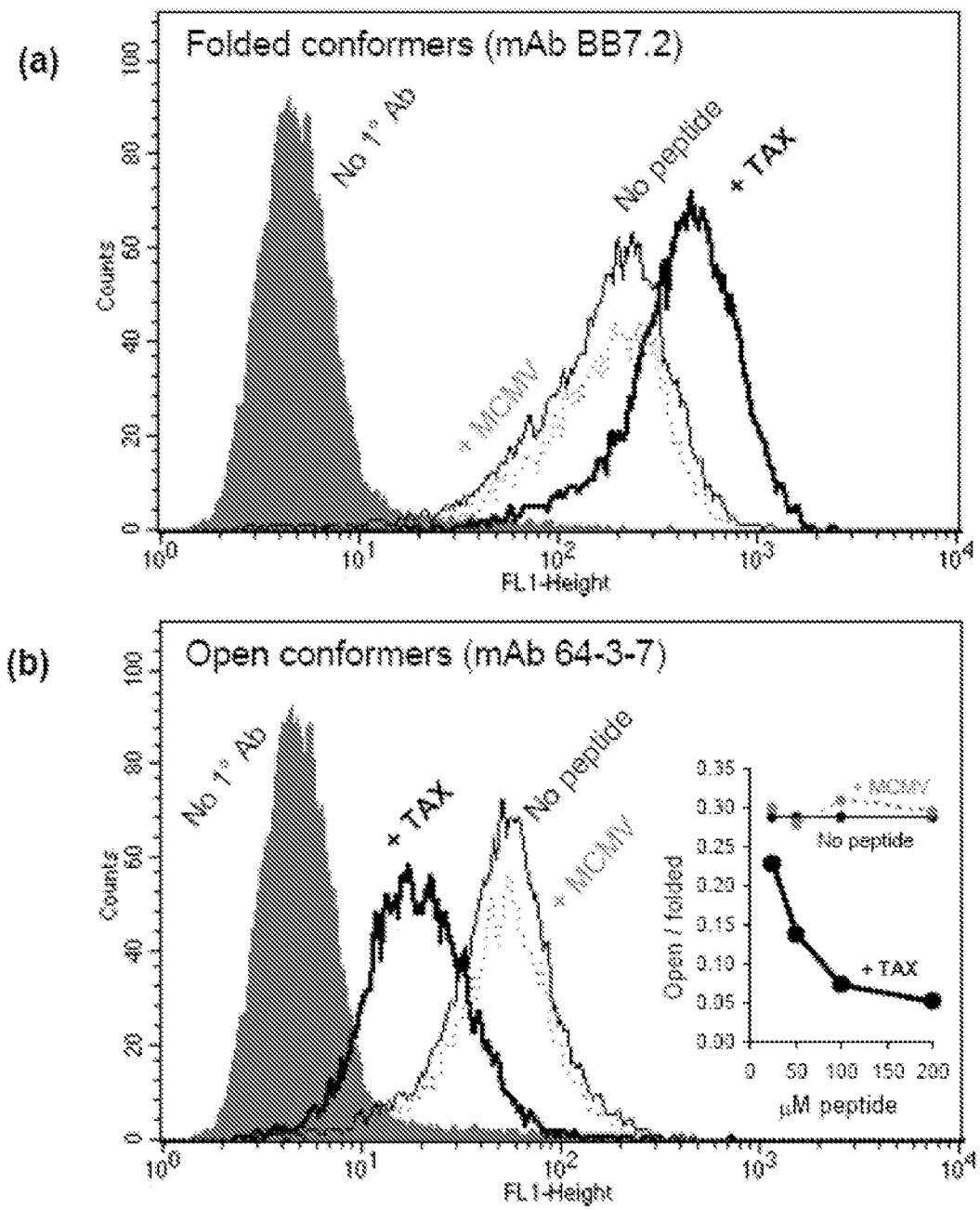
FIG. 14. Detection of peptide-empty A2 conformers by means of the 64-3-7 epitope tag. HeLa cells expressing 64-3-7 epitope-tagged A2 molecules were stained with either (a) mAb BB7.2, which is specific for folded A2 conformers, or (b) mAb 64-3-7, which has been shown for several other MHC alleles to be specific for peptide-empty, or "open" MHC conformers. Addition of specific peptide TAX (thick black line) increased levels of BB7.2 and decreased reactivity with 64-3-7. Nonspecific peptide MCMV (gray dotted line) had no effect. No peptide (thin black line) and secondary-only controls (filled histogram) are also shown. The inset in panel (b) shows peptide dose-dependent changes in the ratio of open to folded MHC conformers for cells fed TAX peptide (thick black line), MCMV negative control peptide (dotted gray line), or no peptide (thin black line).

Hence, in some experiments, HeLa cells expressing 64-3-7 epitope-tagged β$_2$m.A2 were incubated overnight with the A2-binding TAX peptide, control peptide, or no peptide. Specific peptide induced expression of folded A2 conformers was defected by BB7.2 (FIG. 14a), and reduced expression of open A2 conformers was detected by 64-3-7 (FIG. 14b). With increasing amounts of specific peptide, the ratio of open to folded conformers was markedly reduced (FIG. 14c). Thus 64-3-7 reliably detected the loss of open A2 conformers after addition of specific peptide. These observations validated the use of the 64-3-7 epitope in A2SCTs to measure serologically the effects of a disulfide trap.

Example 10

This example illustrates cell surface levels of open and closed conformers of epitope-tagged G280-9V.β$_2$m.A2 SCT with or without the disulfide trap.

Using flow cytometry, we compared cell surface levels of open and closed conformers of 64-3-7 epitope-tagged G280-9V,β$_2$m.A2 SCT either with or without the disulfide trap (FIG. 15a). Like the parent molecule, the dtSCT was fully capable of high levels of surface expression. However, introducing the disulfide trap resulted in a >10-fold decrease in the number of cell surface open conformers. This finding indicates that the disulfide trap prevented dissociation of the linker attached peptide and thus lowered steady state detection of SCT molecules with an open peptide binding groove.

Example 11

This example illustrates formation of a disulfide trap.

To directly test whether the disulfide trap was formed, a biochemical approach was taken. Considering the placement of the engineered disulfide bond, the radius of gyration of the denatured SCT molecule is expected to be significantly shortened under nonreducing SDS-PAGE conditions, which would result in faster migration through polyacrylamide. This was indeed the case (FIG. 15b). All of the disulfide-trap SCT material migrated more quickly through the gel matrix than non-trapped parental G280-9V.β2m.A2 SCT, while both migrated equivalently under reducing conditions. Thus, the disulfide trap is in place with cysteines properly oxidized, and the approach is compatible with thioreductase activities present in the endoplasmic reticulum.

Example 12

This example illustrates T cell recognition of the dtSCT

Figure 3A:
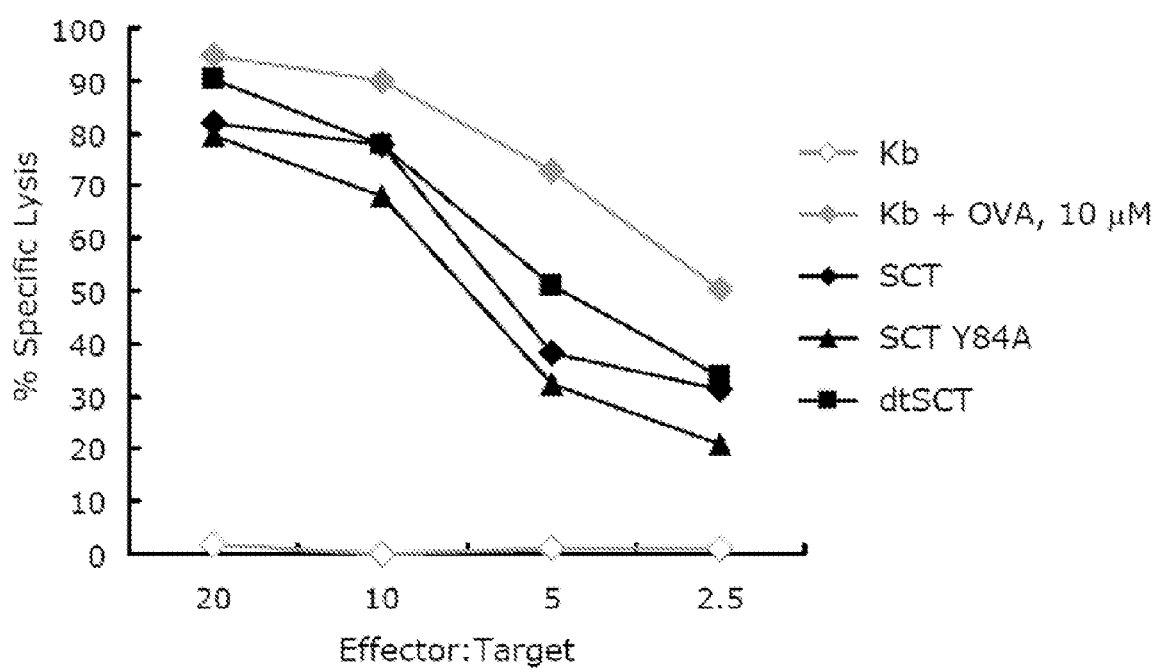
FIG. 3. T cell recognition of SCT and dtSCT constructs. A, All versions of Kb/OVA SCT are recognized by OT-1 T cells, LM1.8 cells expressing the indicated constructs were tested as targets for cytolytic OT-1 T cells in a 4-hour $^{51}$Cr-release assay. B, 2C T cells recognize the QL9.β$_2$m.Ld dtSCT as efficiently as native Ld/QL9. 2C T cells likely recognize Ld bound to endogenous ligand in control cells not fed exogenous QL9 peptide (Δ).

Given that T cells are highly sensitive to perturbations in the MHC/peptide structure and/or conformation, it was imperative to determine whether the mutations in the dtSCT constructs affected T cell recognition. The dtSCT and each of the previous versions of the OVA.β$_2$m.Kb SCT were transduced into LM1.8 cells (H2k fibroblast expressing ICAM) and tested in chromium-release assays as targets for Kb/OVA-reactive OT-1 T cells (FIG. 3A). Cells expressing dtSCT and SCT constructs were strongly recognized by OT-1 in cytolytic assays, while LM1.8-Kb cells were not. Additionally, the B3Z T cell hybridoma (49), which is also specific for the Kb/OVA complex, responds robustly to 3KO fibroblasts expressing the dtSCT construct (Y84C, L2C) or any of the other cysteine variants. Thus, disulfide bond engineering of the single-chain class I molecule preserves the ability to present the OVA epitope to 2 of 2 distinct T cell clones.

As further evidence of the integrity of the interaction between TCR and SCT molecules, we have found that SCT tetramers and conventional tetramers detect the same polyclonal antigen-specific T cells after pathogen infection. The same holds true for tetramers built with the engineered disulfide-trap—they retain the ability to bind the same T cells as conventional tetramers.

Example 13

Figure 16A:
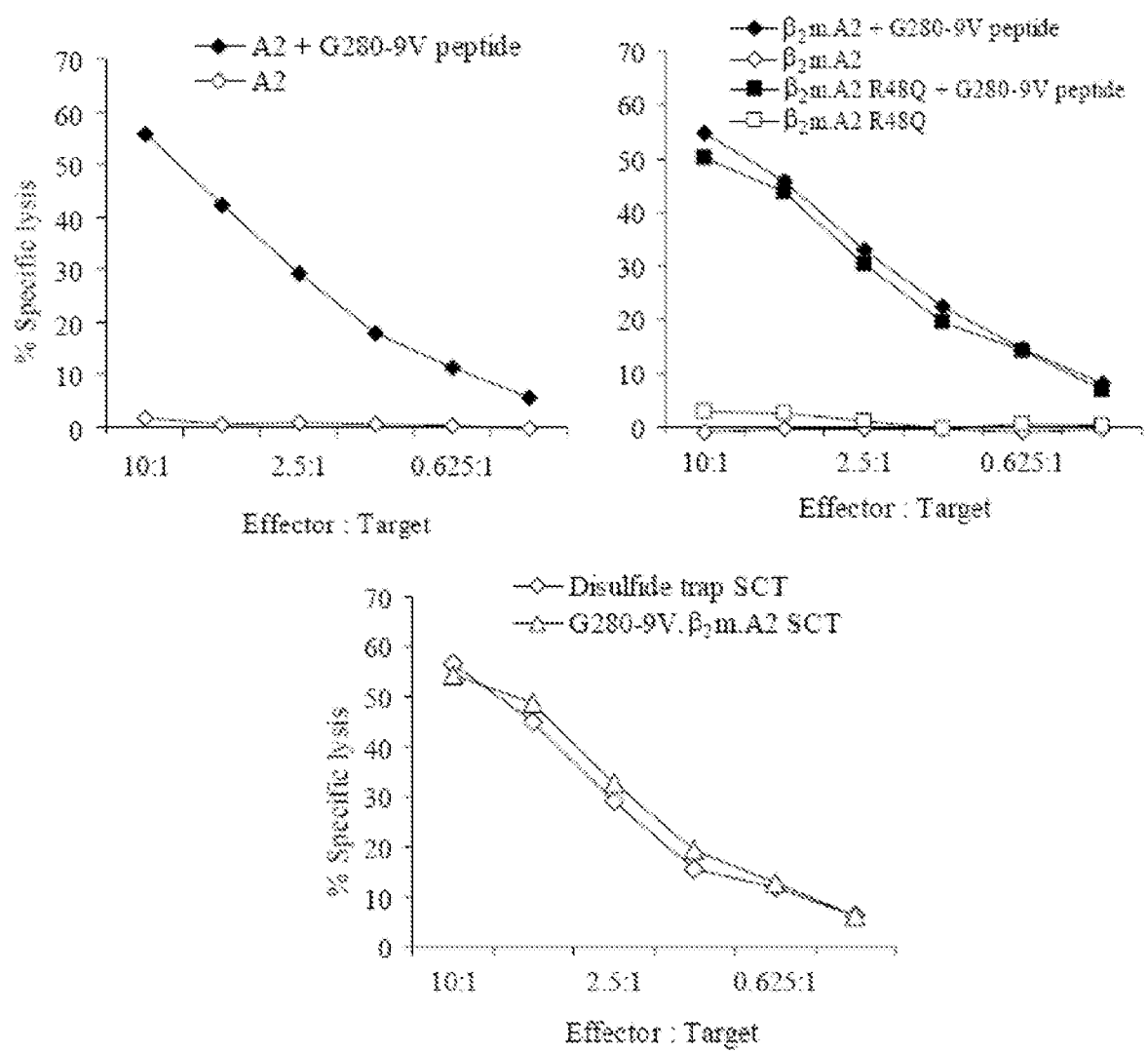
FIG. 16. Disulfide-trap HLA SCT is refractory to binding of competitor peptide, (a) CTLs specific for the G280-9V/A2 (upper left panel) recognized A2 molecules with or without the 64-3-7 epitope (upper right panel), demonstrating that the point mutation required for introducing this epitope does not affect peptide binding or T cell recognition. The G280-9V.$\beta_2$m.A2 SCT as well as the disulfide-trap engineered SCT were both strongly recognized by G280-9V/A2-specific CTL (lower panel), (b) Increasing concentrations of the A2-binding pp65 competitor peptide were incubated with target cells expressing the A2 SCT with or without the disulfide trap. While the SCT of original design readily accepted the competitor at $10^{-11}$ M, the disulfide trap SCT did not allow any significant access to the A2 binding groove, even with a 10,000-fold higher competitor peptide concentration.
Figure 16B:
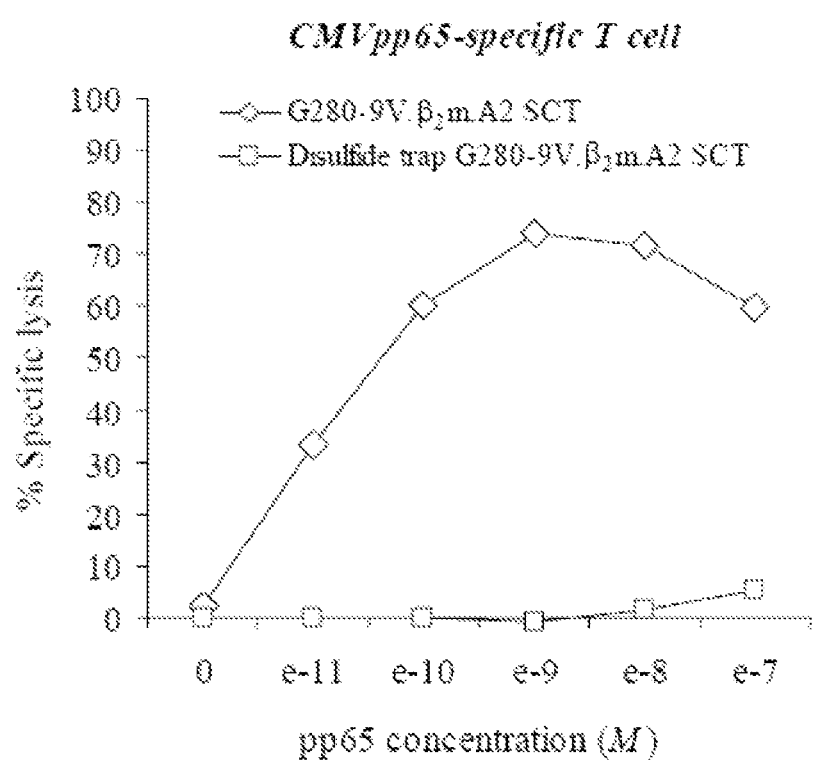

This example illustrates both T cell recognition of the disulfide-trap HLA SCT and exclusion of competitor peptides In these experiments, to determine whether the disulfide-trapped SCT retains its native conformation for antigen presentation, a CTL line specific for the A2/G280-9V complex was used (FIG. 16a). As expected, this T cell line did not recognize untransfected HeLa target cells, even when incubated with the G280-9V peptide. However in the presence of the G280-9V peptide, this T cell line did displayed comparable recognition of native A2 or the β$_2$m.A2 dimer with or without the 64-3-7 tag. This latter finding is important because it establishes that the 64-3-7 tag itself does not interfere with T cell recognition or peptide binding. This finding is consistent with the location of the epitope tag and incorporation of this tag into other human and mouse class I heavy chains. As also shown in FIG. 16a, T cell recognition of the G280-9V.β$_2$m.A2 SCT with or without the disulfide trap were strikingly similar. Therefore, this molecular approach to securing peptide into the SCT is compatible with the antigen presentation function of HLA molecules, and suggests that it does not interfere with the positioning of the peptide in the A2 groove.

Example 14

This example illustrates that a disulfide trap functionally retains an antigenic peptide.

In these experiments, to test whether the disulfide trap functionally retains the antigenic peptide, a T cell assay was used to monitor the intrusion of competitor peptides into the SCT peptide binding groove. For these assays, a CTL line specific for A2/CMVpp65 was used to monitor exogenous peptide binding by the G2809V.β$_2$m.A2SCT (FIG. 16b). As shown, the pp65 competitor readily gained access to the SCT groove lacking a trap, since the HeLa G280-9V.β2m.A2SCT targets were lysed even in the presence of low concentrations of pp65 peptide. It is interesting to note that using the same approach, the G280-9V.β2m.A2SCT was considerably more susceptible to binding exogenous pp65 peptide compared to the TAX.β$_2$m.A2SCT (compare FIG. 16b to 16e). This finding is consistent with the predicted t$_{1/2}$ stabilities of these peptides bound to A2 (G280-9V, 20.4 min.; CMV pp65, 159.9 min.; and TAX, 2496.1 min.) (120). Thus the weaker binding peptide in the SCT is more displaceable.

A remarkable finding is the difference the disulfide trap made to the susceptibility of the G2809V.β$_2$m.A2SCT to binding exogenous pp65 (FIG. 16b). In the experiments, no significant level of CTL recognition of pp65 could be detected even with 10,000 times the concentration of competitor peptide that would induce lysis of cells expressing the original SCT. Thus serological, biochemical, and T cell-based assays demonstrate that a disulfide trap can be incorporated into a human SCT to secure a relatively weak binding peptide, without disrupting T cell recognition. In data not shown, similar findings demonstrating the efficacy of the disulfide trap were observed with a FluM1.β2m.A2 dtSCT.

Example 15

This example illustrates that dtSCT molecules exclude high affinity competitor peptides.

Figure 4A:
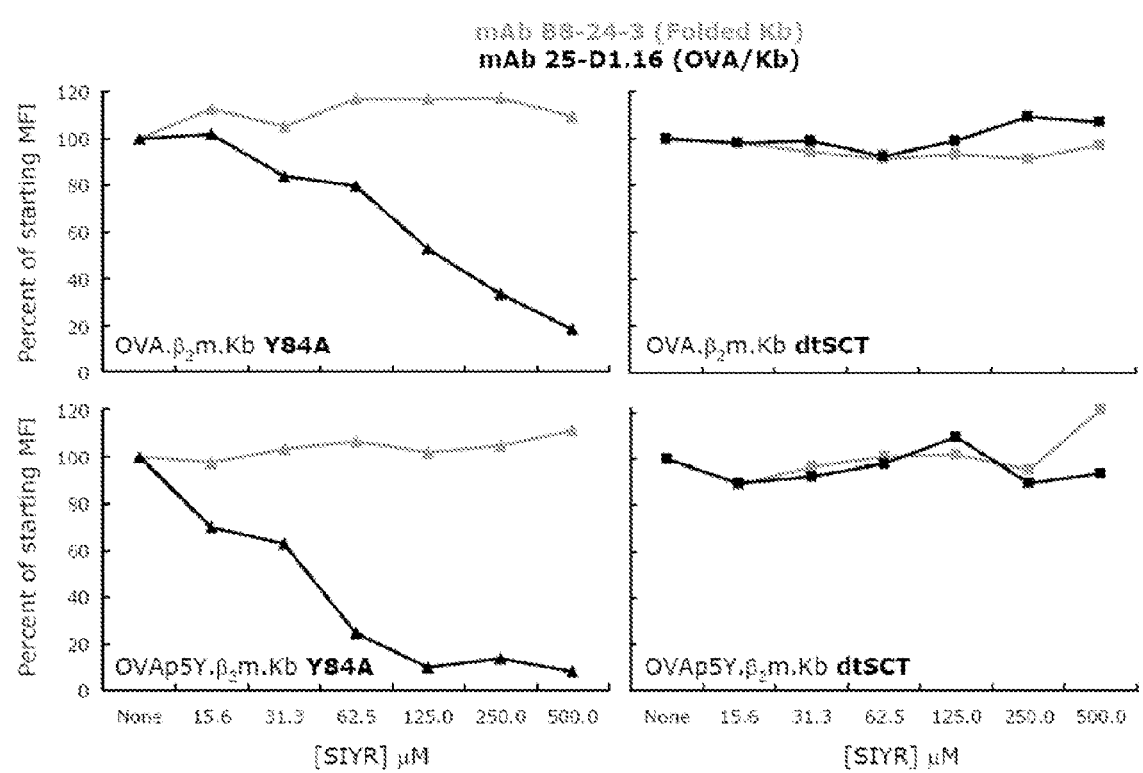
FIG. 4. The disulfide trap in OVA.β$_2$m.Kb SCTs effectively prevents binding of exogenous competitor peptides. A, Loss of mAb 25-D1.16 reactivity to monitor displacement of OVA or OVAp5Y from Kb SCT constructs. 3KO cells expressing the indicated constructs were incubated with increasing concentrations of exogenous SIYR peptide and analyzed by flow cytometry with antibodies specific for K$^b$ (mAb B8-24-3, gray) or Kb/OVA complex (mAb 25-D1.16, black). Mean fluorescence intensity at each dose of competitor is plotted as a percentage of the starting signal (no competitor). B, N15 hybridoma activation to detect VSV8 competitor peptide binding to SCT constructs. 3KO cells expressing the indicated constructs, including OVA.β$_2$m.Kb SCTs or OVAp5Y.β$_2$m.SCTs, were incubated with increasing concentrations of exogenous VSV8 peptide, washed, and cultured with the N15 hybridoma. IL-2 produced upon activation of the hybridoma was detected measuring CTLL-2 proliferation, which was in turn detected by Alamar blue fluorescence at 590 nm. The level of N15 activation that occurs upon VSV8 binding to native Kb (loaded with endogenous peptides in B6/WT3 fibroblasts) is shown for comparison.

A crucial test of the utility of the dtSCT was to measure its capacity to exclude competing peptides. We had previously found that the SCT format without the disulfide trap excluded high-affinity competitor peptides to a great extent (10), about 1000 times more effectively than native Kb loaded with endogenous peptides. This exclusion of competitor peptides was enhanced by the Y84A mutation in the SCT that opens the groove and allows for better linker accommodation (11). To test the dtSCT construct, we incubated cells expressing the dtSCT with increasing amounts of exogenous high-affinity competitor, the Kb-binding SIYR peptide (27). Reactivity of mAb 25-D1.16 was used to specifically monitor the loss of Kb/OVA complexes. In control cells expressing the Y84A SCT, half of the Kb/OVA complexes were displaced by the addition of 1.25 µM competitor (FIG. 4A, upper left). The cells expressing the OVA.β$_2$m.Kb dtSCT displayed no diminution of reactivity with the 25-D1.16 antibody at the highest concentration tested (500 µM) (FIG. 4A, upper right). Thus the preponderance of the dtSCT molecules retained the OVA peptide in the face of high concentrations of competitor, which was clear evidence that the engineered disulfide bond was present and functioning as expected to lock in the SCT peptide.

Figure 4B:
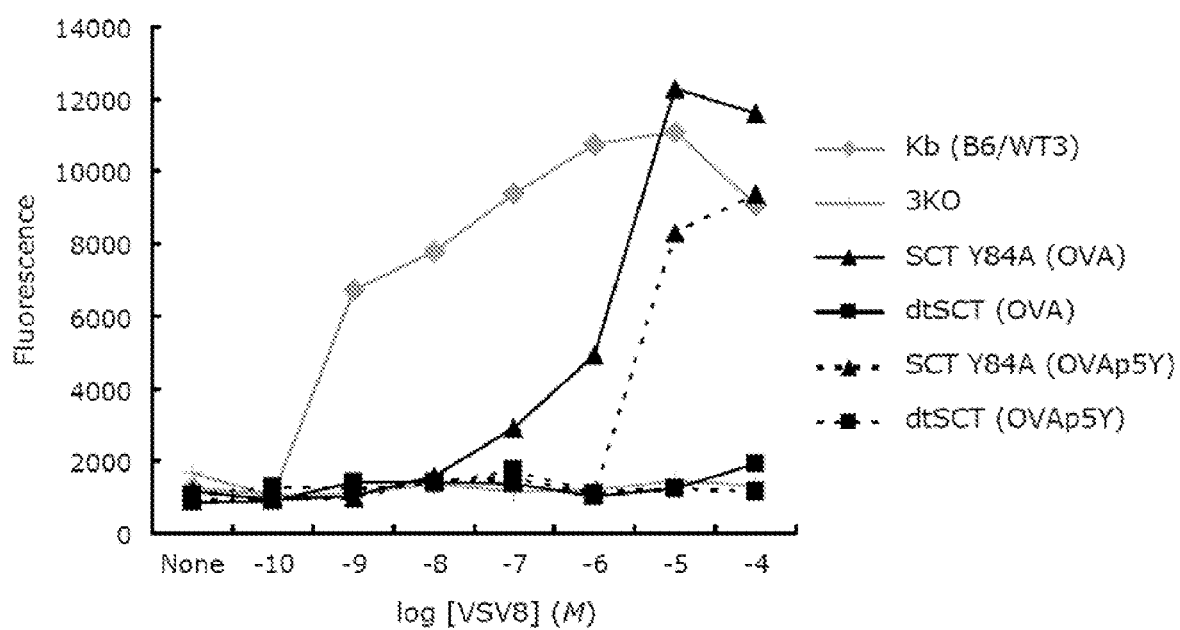

However, this assay does not detect very low levels of competitor binding, which could be sufficient for T cell recognition. Thus, as a complementary approach, we also monitored exogenous peptide binding using a gain of recognition T cell assay. For this assay we used the highly sensitive T cell hybridoma N15. The N15 hybridoma, derived from the TCR murine hybridoma 58α-β- (38), expresses the N15 TCR, which is specific for the VSV8/Kb complex, as well as CD8 α and β chains (39). As shown in FIG. 4B, the N15 hybridoma was readily activated when cells expressing Kb were fed $10^{-9}$ M exogenous VSV8 peptide. On the order of $10^{-6}$ M VSV8 peptide was required to attain the same level of N15 activation in the context of the OVA.β$_2$m.Kb SCT Y84A construct. Yet most striking was disulfide trap, which enabled the OVA.β$_2$m.Kb dtSCT to effectively exclude even $10^{-4}$ M VSV8 competitor peptide. These combined biochemical (FIG. 2B), serological (FIG. 4A) and T cell (FIG. 4B) assays provide compelling evidence that the engineered disulfide bond is in place and functions to exclude the binding of exogenous peptides. The disulfide trap extends the remarkable ability of SCT to prevent the binding of other peptides in comparison with Kb loaded with endogenous peptides. It should be noted, however, that while the SCT appears to prevent exogenous peptide binding by rapidly rebinding the SCT peptide (11), the dtSCT format clearly secures the SCT peptide permanently in the groove, such that no other peptide can gain access.

Example 16

The example illustrates that a poor-binding OVA analog can be tethered to the MHC groove using the dtSCT approach.

The above results demonstrate that a dtSCT can exhibit stronger binding of the covalently attached peptide compared to an SCT without the disulfide trap. Accordingly, a dtSCT can be used to enhance presentation of relatively poor-binding peptides. As a demonstration, we investigated the previously described OVA analog SIINYEKL (SEQ ID NO: 36), or OVAp5Y which binds poorly to Kb (50-52). Howarth et al. showed that the OVAp5Y analog was still recognized in the context of Kb by the 25-D1.16 mAb (50). Furthermore, they demonstrated that the surface half-life of Kb/OVAp5Y complexes was reduced 3-fold and efficiency of expression more than 75-fold compared to native Kb/OVA complexes. Therefore, using this OVA analog as a model of a poor-binding peptide for Kb, we constructed an OVAp5Y.β$_2$m.Kb SCT and an OVAp5Y.β$_2$m.Kb dtSCT (i.e., with and without a disulfide trap, respectively (Table 2)). Although the steady-state cell surface expression level of the OVAp5Y SCT was approximately 10-fold lower than the OVA-based SCT, the surface expression of OVAp5Y SCT was improved three-fold by the addition of the disulfide trap, demonstrating that the disulfide trap facilitates de novo folding and/or increases cell surface stability of SCTs constructed with weak-binding peptides. In peptide competition experiments, the OVAp5Y.β$_2$m.Kb Y84A SCT was readily displaced with the SIYR peptide (FIG. 4A, lower left). Staining with the Kb/OVA-specific mAb was half-maximal at approximately 40 µM SIYR compared to 125 µM for the SCT constructed with OVA (FIG. 4A, upper left), consistent with its poorer affinity for Kb. However, when the disulfide-trapped OVAp5Y SCT was subjected to the same concentrations of competitor peptide, no loss of reactivity with 25-D1.16 was detected (FIG. 4A, lower right).

The Kb SCT and dtSCT constructed with the weak-binding OVA analog were also tested in N15 hybridoma assays (FIG. 4B). Interestingly, when fed the VSV8 peptide, the OVAp5Y SCT Y84A activated the hybridoma somewhat less efficiently, most likely due to its lower Kb surface expression. However, the VSV8 peptide was still effectively excluded from the OVAp5Y.β$_2$m.Kb dtSCT—the N15 hybridoma was not activated even though this construct has 3-fold higher cell surface expression compared to OVAp5Y SCT Y84A. This was a clear demonstration that the engineered disulfide bond is able to lock in even a peptide that binds weakly to the native MHC and thus exclude high-affinity exogenous competitor peptides. The combined findings with OVA and OVAp5Y-based dtSCTs argue strongly that the engineered disulfide bond is properly formed in the great majority of the cell surface dtSCT molecules.

Example 17

This example illustrates that a second, low-affinity H-2 complex can be secured when expressed as a dtSCT.

To test the applicability of the dtSCT technology on an additional class 1/peptide complex, and to further test its ability to enhance presentation of a lower affinity complex, we employed the Ld/QL9 complex. The QL9 peptide (QL-SPFPFDL) (SEQ ID NO: 32) is derived from an endogenous dehydrogenase and binds to the H-2Ld (29-31), a class I allele which is unique due to its relatively weak association with peptide and β$_2$m (15, 53). Importantly for this study, the Ld/QL9 complex is relatively unstable based on its limited cell surface half-life (about ½ hr) and the difficulty of constructing Ld/QL9 tetramers. Thus, the Ld/QL9 complex was ideal for testing the stabilizing effects on class I molecules conferred by the single-chain format itself and by the introduction of a disulfide bond. A second advantage of studying the Ld molecule is the ability to measure directly relative amounts of peptide-occupied versus peptide-empty class I conformers at the cell surface with mAb 64-3-7, which specifically detects open (peptide-empty) class I molecules (25, 31, 54-56), A third reason to construct SCTs of the Ld/QL9 complex was its well-defined reactivity to the 2C TCR (31, 57, 58) and the availability of a recombinant high-affinity 2C-derived mutant TCR designated m6a (34-36), which is an excellent peptide-specific Ld/QL9 staining reagent for flow cytometry.

In these experiments native Ld and QL9.β$_2$m.Ld SCTs with or without the disulfide trap were subcloned individually into a retroviral vector for expression in B6-derived fibroblasts. As a control, a QL9.β$_2$m.Ld SCT with the Y84A mutation was also included. This mutation opens the groove and reduces binding of exogenous peptides (11). As shown in FIG. 5, Ld and the three different Ld/QL9 SCTs were detected at high levels on the cell surface by the mAb 30-5-7, which is specific for folded (peptide-associated) Ld molecules (55). This, combined with the staining pattern of mAb 64-3-7 on each of these transduced cell lines was especially informative, because it provided a relative measure of peptide-induced folding. Native Ld had the highest ratio of open conformers to folded conformers detected by mAb 30-5-7 (open:folded=1.01), which was an indication of its characteristically weak association with endogenous peptides. Expressing Ld in single-chain format with the QL9 peptide resulted in a lower level of staining with mAb 64-3-7 (open: folded=0.504), and introducing the Y84A mutation lowered the ratio even further (open:folded=0.250). By comparison, when the disulfide trap was present in the QL9.β$_2$m.Ld SCT, peptide-empty (mAb 64-3-7') conformers were barely detectable (open:folded=0.012). We concluded from this experiment that the disulfide-trap was functional, and significantly increased peptide occupancy of this relatively weak class I/peptide complex.

Figure 6A:
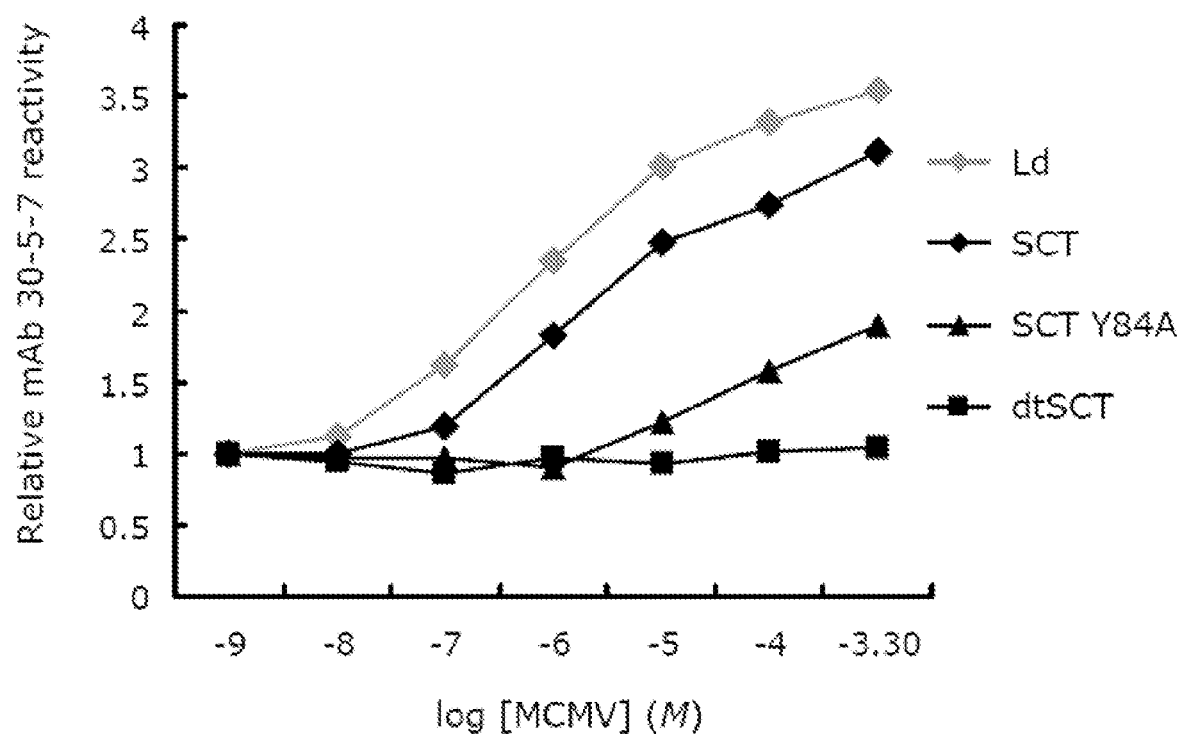
FIG. 6. A, Induction of Ld and Ld SCT cell surface expression by addition of exogenous peptide. As a measure of peptide-receptiveness, surface induction was measured for each of the four indicated constructs expressed in B6/WT3 cells. In contrast to previous assays (see FIG. 4) which measured peptide exchange at the cell surface, brefeldin A was excluded from this assay to allow arrival of newly synthesized molecules at the cell surface. Cells were incubated for 4 hours with increasing concentrations of MCMV peptide and stained with antibody to Ld (mAb 30-5-7). Mean fluorescence intensity is plotted relative to the lowest MCMV concentration for each cell line. B, Displacement of the QL9 peptide moiety of QL9.β$_2$m.Ld SCT or dtSCT with high-affinity exogenous competitor peptide. B6/WT3 cells expressing the indicated constructs were incubated with increasing concentrations of exogenous MCMV peptide and analyzed by flow cytometry with the high-affinity, recombinant m6α TCR (specific for the Ld/QL9 complexes). Mean fluorescence intensity at each dose of competitor is plotted as a percentage of the starting signal (no competitor).

Peptide occupancy determines the half-life of class I molecules at the cell surface (59). Ld, being a relatively poor peptide binder, is thus highly inducible at the cell surface by incubation with exogenous ligands (15). Given this we reasoned that susceptibility to peptide induction would be informative for comparing the relative peptide occupancy of the Ld/QL9 SCT complexes. As shown in FIG. 6A, culture of cells with exogenous Ld-binding peptide from murine cytomegalovirus (MCMV) (32) increased surface expression of native Ld>3-fold. Furthermore, exogenous MCMV peptide increased the expression of the QL9.β$_2$m.Ld SCT (about 3-fold) and to a lesser extent the QL9.β$_2$m.Ld Y84A SCT (about 1.5-fold). The most striking result of this experiment was the constant expression level of the disulfide trap SCT at all exogenous peptide concentrations tested. Thus, as monitored by surface stabilization, for relatively unstable MHC/peptide complexes such as Ld/QL9, the disulfide trap renders the SCT more refractory to exogenous peptide binding.

Figure 3B:
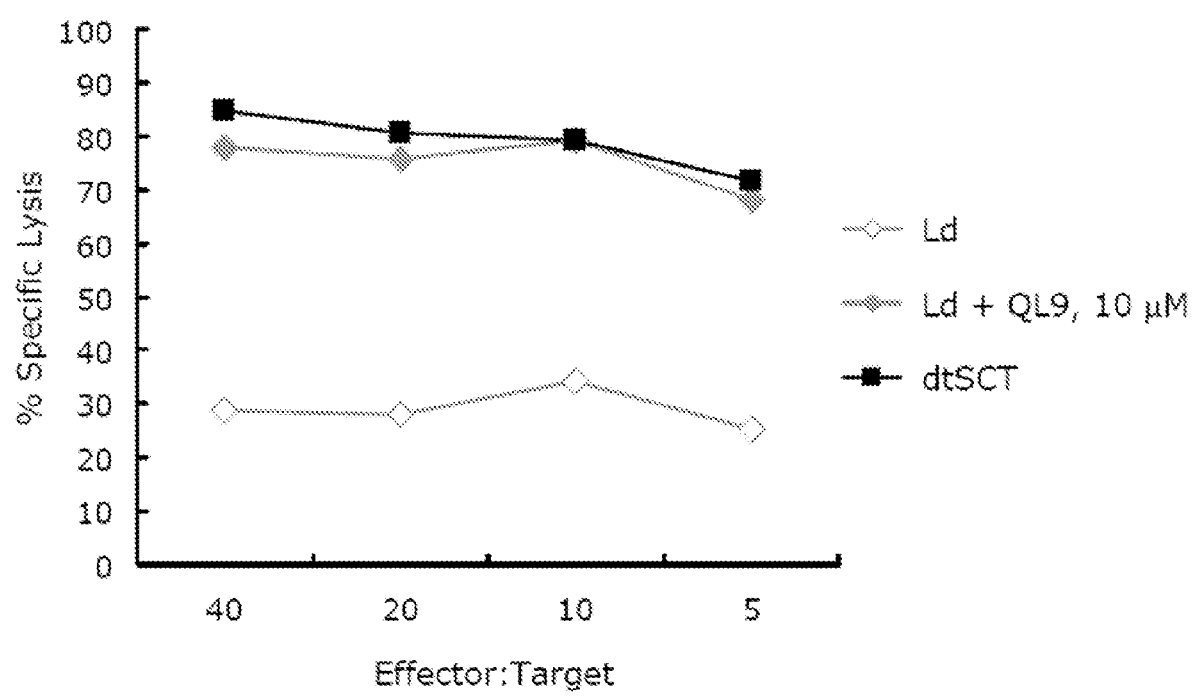

We next wanted to extend these findings with Ld/QL9 SCTs with more physiologically relevant TCR based assays. It should first be noted that 2C T cells detected target cells expressing QL9.β$_2$m.Ld dtSCT or QL9 peptide-fed targets comparably (FIG. 3B). To detect Ld/QL9 complexes on the cell surface by flow cytometry, we stained these cells with the recombinant TCR m6α (FIG. 5). This high-affinity TCR variant was selected in vitro by yeast display of a library of 2C TCR mutants; its affinity for Ld/QL9 ($K_D \approx 9$ nM) (35) is over 100-fold greater than that of wildtype 2C ($K_D \approx 1.5$ μM) and thus approaches the affinity of antibody/antigen complexes. Interestingly, m6α bound relatively poorly to the QL9.β$_2$m.Ld SCT (FIG. 5), likely reflecting the fact that residue Y84 in this construct forces the linker extending from the C terminus of the peptide to bulge, hindering m6α binding. Consistent with this conclusion, the SCTs with the Y84A mutation or the disulfide trap have a more relaxed linker and better detection by recombinant TCR m6α (FIG. 5). In any case, the disulfide-trapped form of the QL9.β$_2$m.Ld SCT displayed strong engagement with both the 2C TCR and its derivative, high affinity, recombinant TCR m6α.

Figure 6B:
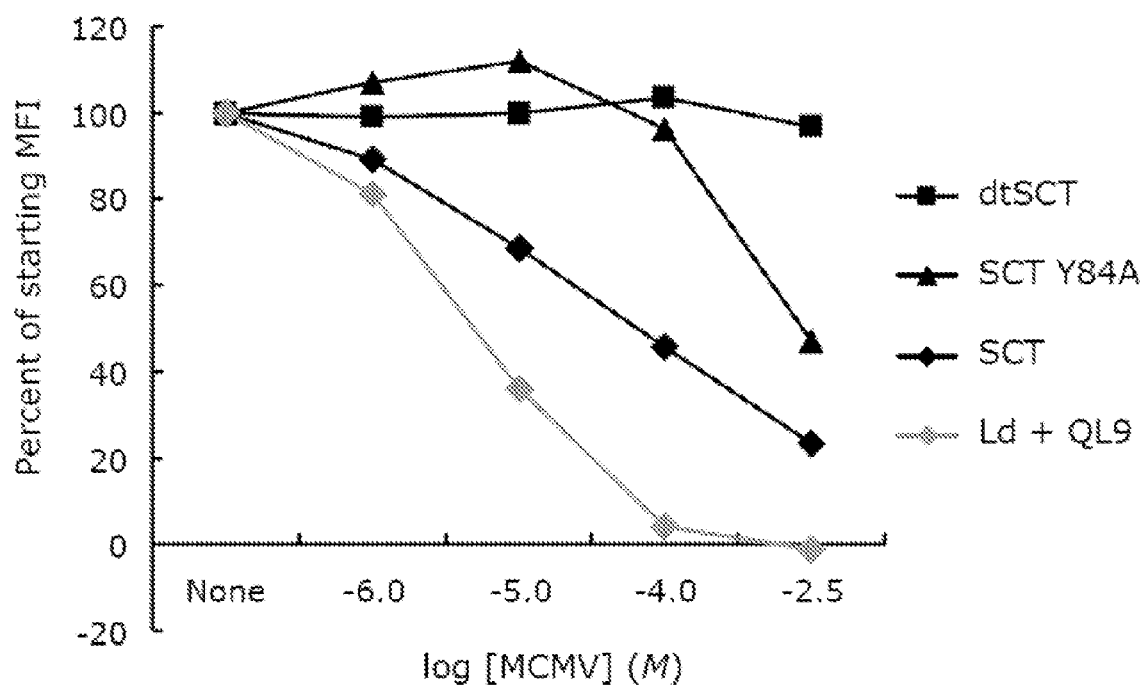

The strong reactivity of m6α TCR for the dtSCT allowed us to determine the extent to which disulfide trapping of the QL9 peptide to Ld excluded competitor peptides relative to native Ld/QL9 complexes. Cells expressing native Ld were fed exogenous QL9 peptide overnight. The next morning these cells, along with cells expressing each generation of QL9.β$_2$m.Ld SCT, were incubated with increasing concentrations of competitor peptide YPHFMPTNL (SEQ ID NO: 33) from murine cytomegalovirus (MCMV) pp89 (32), which binds to Ld with similar affinity to QL9 (60). The cells were then stained with recombinant m6α TCR and analyzed by flow cytometry to specifically detect loss of the Ld/QL9 epitope (FIG. 6B). Interestingly, susceptibility to peptide exchange correlated precisely with the levels of cell-surface open conformers (staining with mAb 64-3-7, see FIG. 5). Native Ld loaded with the QL9 peptide readily bound the MCMV peptide, while each generation of Ld SCT was increasingly more resistant to exogenous peptide binding. Even the highest doses of competitor peptide had no effect on the Ld dtSCT. Thus disulfide bond engineering reformed a normally poor peptide binder into an exceptionally stable MHC molecule.

Example 18

This example illustrates SCT design rationale

Figure 7F:
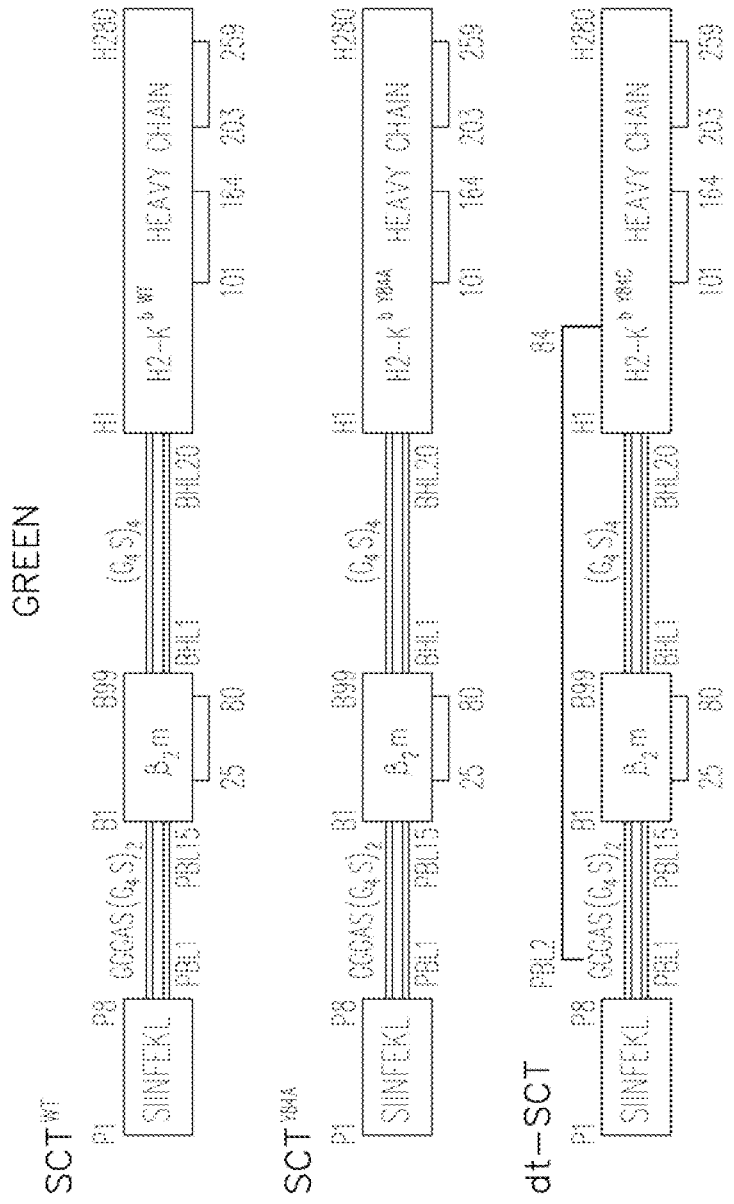
FIG. 7. Single Chain Trimer designs and structural features. A Schematic representation of each of the SCT protein designs is shown from the N to the C terminus. Ova, $\beta_2$m, and heavy chain, are represented as yellow, magenta, and cyan boxes, respectively. The linkers are represented as thin orange boxes. The linker between the Ova peptide and $\beta_2$m is designated PBL; the linker between $\beta_2$m and the heavy chain is designated BBL. Linker sequences and residue numbering for Ova, $\beta_2$m, and heavy chain are shown above their respective representations. The sequence of Ova is shown inside its box representation. Disulfide bonds bridging the indicated cysteine residues in $\beta_2$m, $K^b$ heavy chain, and the disulfide-trap in the $SCT^{Y84C-PBL2C}$ construct are represented as green brackets. Adapted from original color figure; panels highlight original colors against a dimmed background.

In these experiments, the initial SCT, designated here SCT$^{WT}$, was designed by linking the C terminus of Ova peptide (SIINFEKL (SEQ ID NO: 29), Ovalbumin, residues 257-264) using a GGGGSGGGGSGGGGS (SEQ ID NO: 34) linker to the N terminus of β$_2$m and linking the C terminus of β$_2$m to the N terminus of the Kb heavy chain using a GGGSGGGSGGGSGGGSGGGS (SEQ ID NO: 38) linker (FIG. 7). When expressed at the cell surface this SCT construct was more refractory to loading with exogenous peptide as compared to Kb bound with endogenous peptides. However, high concentrations of competitor peptide displaced the Ova peptide of the SCT more readily than Ova bound to native Kb (10). We hypothesized that this was due to poor linker accommodation and loss of C-terminal, peptide anchoring in the F pocket of the SCT. To improve peptide occupancy and to stabilize peptide-MHC association, we reengineered the peptide-binding groove of the first SCT construct to create two more generations of SCT design.

As a structural framework for the design of the next SCT generations we overlapped the peptide-binding platform of the class II MHC I-E$^k$ protein bound to a hemoglobin-derived peptide onto the α1α2 domain of K$^b$-Ova (42, 96). The I-E$^k$ peptide is attached to the class II β chain via a flexible linker analogous to the one used in our SCT design. Based on the superposition of the peptide-binding platforms the Hb peptide and its linker were docked onto the peptide-binding groove of K$^b$. This modeling exercise allowed us to determine which residues in K$^b$ impede optimal linker accommodation. We selected Tyr$^{84}$ and mutated it to Ala (FIG. 7). We hypothesized that this mutation would open the MHC groove and allow the free extrusion of the peptide-β$_2$m linker out of the MHC groove. Consistent with our expectations, the SCT$^{Y84A}$ proteins exhibited enhanced serological and TCR engagement over the previous SCT generation (11). In addition, its ability to exclude competitor peptide was increased 4-fold likely reflecting impaired binding of the exogenous peptide due to the disrupting of anchoring hydrogen bonds by the Y84A substitution (11).

Next, we sought to introduce a stabilizing disulfide bridge between the peptide and the MHC to replace the loss of C-terminal anchoring. Our overlap model allowed us to determine potential distances between the linker and the MHC for disulfide bond engineering. Several disulfide bridges were introduced involving the conserved MHC residues $Thr^{80}$, $Tyr^{84}$, and $Asn^{86}$ and the first four linker residues. Each of these constructs were introduced in $K^{b-/-}$, $D^{b-/-}$, and $\beta_2m^{-/-}$ (3KO) fibroblasts (20) and their cell-surface expression was detected by flow cytometry. In addition, in vivo disulfide bond formation for each construct was also confirmed. For our structural and functional characterizations, we selected a SCT construct with a disulfide between a cysteine introduced in place of $Tyr^{84}$ and a cysteine introduced at the second position in the peptide-$\beta_2$m linker (FIG. 7). We hypothesized that a Cys at position 84 would maintain an opening in the MHC groove akin to the opening created by the Y84A mutation and that a disulfide bond at this position would substitute for loss of F-pocket, hydrogen-bonding interactions between the peptide and the MHC. This SCT construct was designated $SCT^{Y84C-PBL2C}$. Furthermore, since $Tyr^{84}$ is involved in a highly conserved, hydrogen-bonding network that anchors the peptide C terminus, using a Y84C substitution to incorporate a disulfide trap seemed likely to be translatable to other mouse and human class I peptide-MHC complexes.

Example 19

This example illustrates structure determination.

In these experiments, each of the SCT constructs (FIG. 7) was expressed in *E. coli* as insoluble inclusion bodies. The SCT molecules were formed in vitro under oxidative refolding conditions and were purified using size exclusion and anion exchange chromatographies. Electrospray mass spectral analysis of each SCT confirmed the presence of abundant peaks at 47003 Da, 46909 Da, and 46985 Da respectively corresponding to the predicted molecular weights of $SCT^{WT}$, $SCT^{Y84A}$, and properly oxidized $SCT^{Y84C-PBL2C}$.

Each of the SCT molecules crystallized in the primitive monoclinic space group, $P2_1$, with two molecules per asymmetric unit and nearly identical cell dimensions (Table 3). Initial phase estimates were obtained by rigid-body refinement of the coordinates of $H-2K^{bm8}$ (PDB 1RJY, peptide and water molecules omitted), which was crystallized in the same space group and unit cell dimensions. After initial refinement easily interpretable electron density was seen for the Ova and the linker residues immediately C-terminal Ova that improved upon further building and refinement cycles. Diffraction data to 2.00 Å ($SCT^{WT}$), 2.00 Å ($SCT^{Y84A}$), and 1.80 Å ($SCT^{Y84C-PBL2C}$) were used for refinement of the final atomic models, which have R factors of 21.5% ($R_{free}$ 25.3%) for $SCT^{WT}$, 21.0% ($R_{free}$ 25.2%) for $SCT^{Y84A}$, and 20.8% ($R_{free}$ 23.9%) for $SCT^{Y84C-PBL2C}$.

The electron density maps for each of the SCT molecules were of good to excellent quality. No ambiguities were seen for the main chain and side chains of the Ova peptide in each of the complexes. Interpretable density was seen for all of the residues in the first linker in the $SCT^{WT}$ molecule, for residues 1 through 7 and 11 through 15 in the first linker of $SCT^{Y84A}$, and residues 1 through 7 and 12 through 15 in the first linker of $SCT^{Y84C-PBL2C}$. In each SCT this linker does not adopt any secondary structural elements and is seen in different conformations in each molecule in the asymmetric unit. Clear evidence for disulfide bond formation was seen in both molecules in the asymmetric unit for $SCT^{Y84C-PBL2C}$. No interpretable electron density was seen for the $\beta_2$m-heavy-chain linker and for residues 278 through 280 at the C terminus of the heavy chain in any of the single-chain structures.

Example 20

This example illustrates structural similarities between SCTs and Native $K^b$-Ova.

Figure 8A:
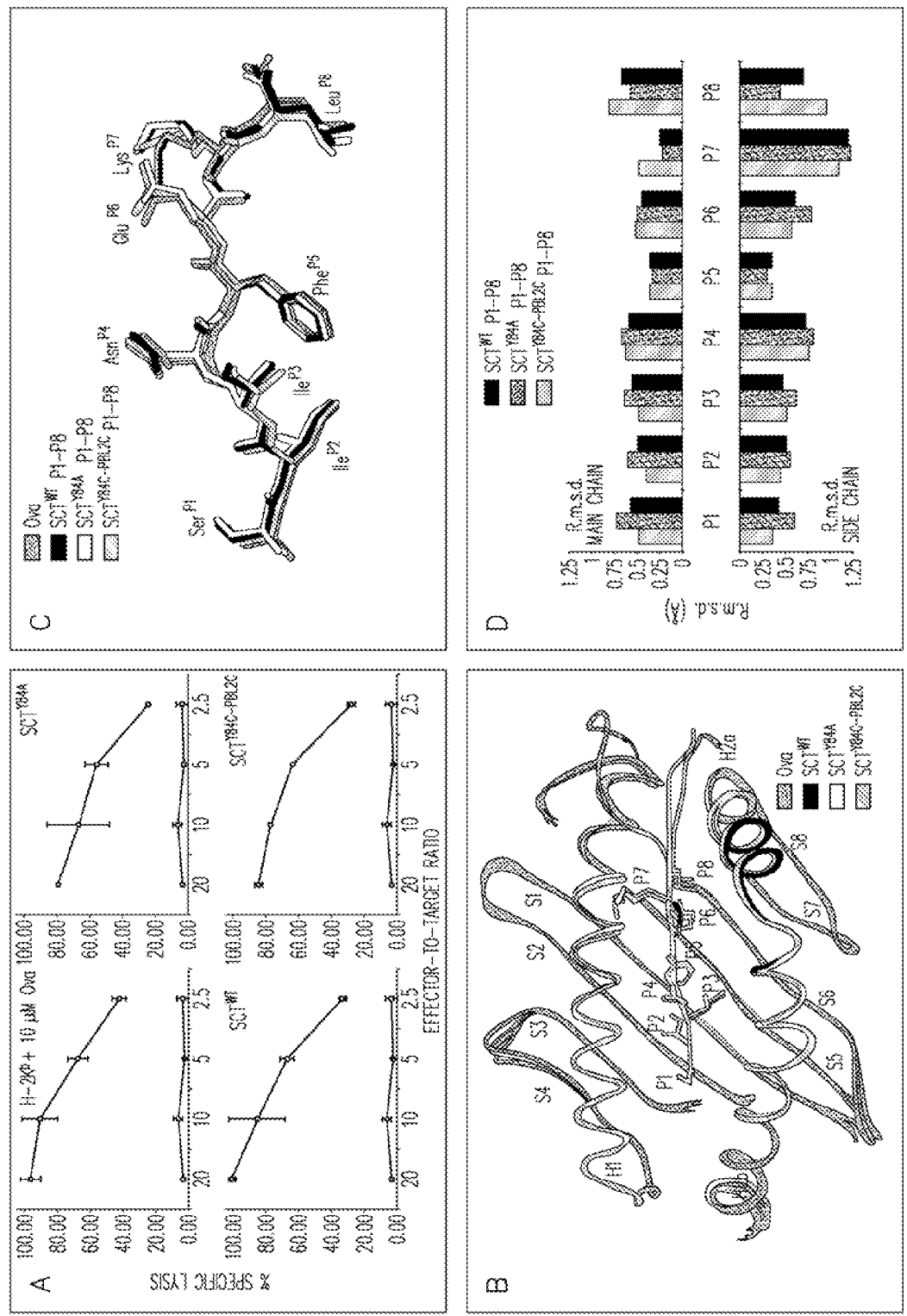
FIG. 8. Functional equivalence and structural similarity between the SCT constructs and native H-2$K^b$-Ova A, Response of OT-1 T cells to LM1.8 cells transfected with H-2$K^b$ and fed 10 µM Ova (panel 1, cyan), $SCT^{WT}$ (panel 2, gray), $SCT^{Y84A}$ (panel 3, yellow), and $SCT^{Y84C-PBL2C}$ (panel 4, magenta) is compared to the OT-1 response to control LM1.8 transfectants (H-2$K^b$, no peptide, shown in red in each panel) in a CTL $^{51}$Cr release assay. The OT-1 TCR recognizes all SCT proteins indicating that native conformations of TCR recognition determinants are preserved within the SCT format, B, The membrane-distal, peptide-binding platforms of $SCT^{WT}$, gray; $SCT^{Y84A}$, yellow; $SCT^{Y84C-PBL2C}$, magenta are superposed onto the platform of $K^b$ in the native complex, cyan. The superposition is based on the overlap of the main chain atoms in the platforms, heavy chain residues 1 through 182. The superposed structures are depicted as small ribbon tubes. Side chains for Ova residues in each SCT and in the native complex are rendered as ball and stick models and colored correspondingly. Structural differences in the platforms are mostly concentrated in solvent exposed loops and their C-terminal regions. Also compared are the conformations of linkers in each SCT; note that the linker in $SCT^{WT}$ passes over the C-terminal, TCR-proximal surface of the α1 helix. C and D, The positions of Ova atoms in each SCT are compared to native Ova. A close-up view of the superposed Ova peptides is shown in a near 90° rotation from the orientation in B. Aligned underneath the peptides (in panel D) are the quantified positional differences, which were graphed to denote per residue main chain (top) and side chain (bottom) differences in reference to Ova. Significant differences were observed only for the side chain of the solvent exposed Lys$^{P7}$. Adapted from original color figure; panels highlight original colors against a dimmed background.
Figure 8B:
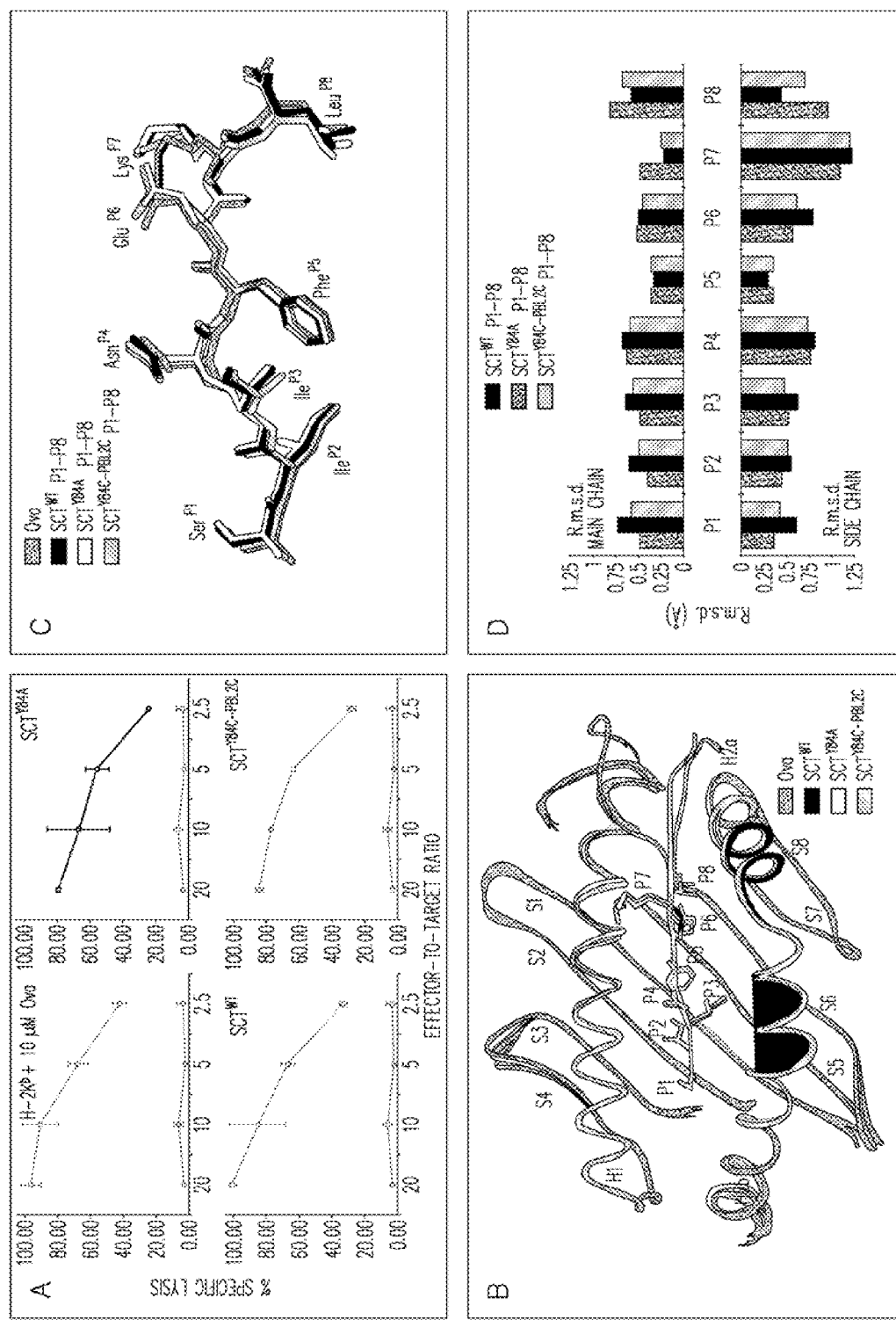
Figure 8C:
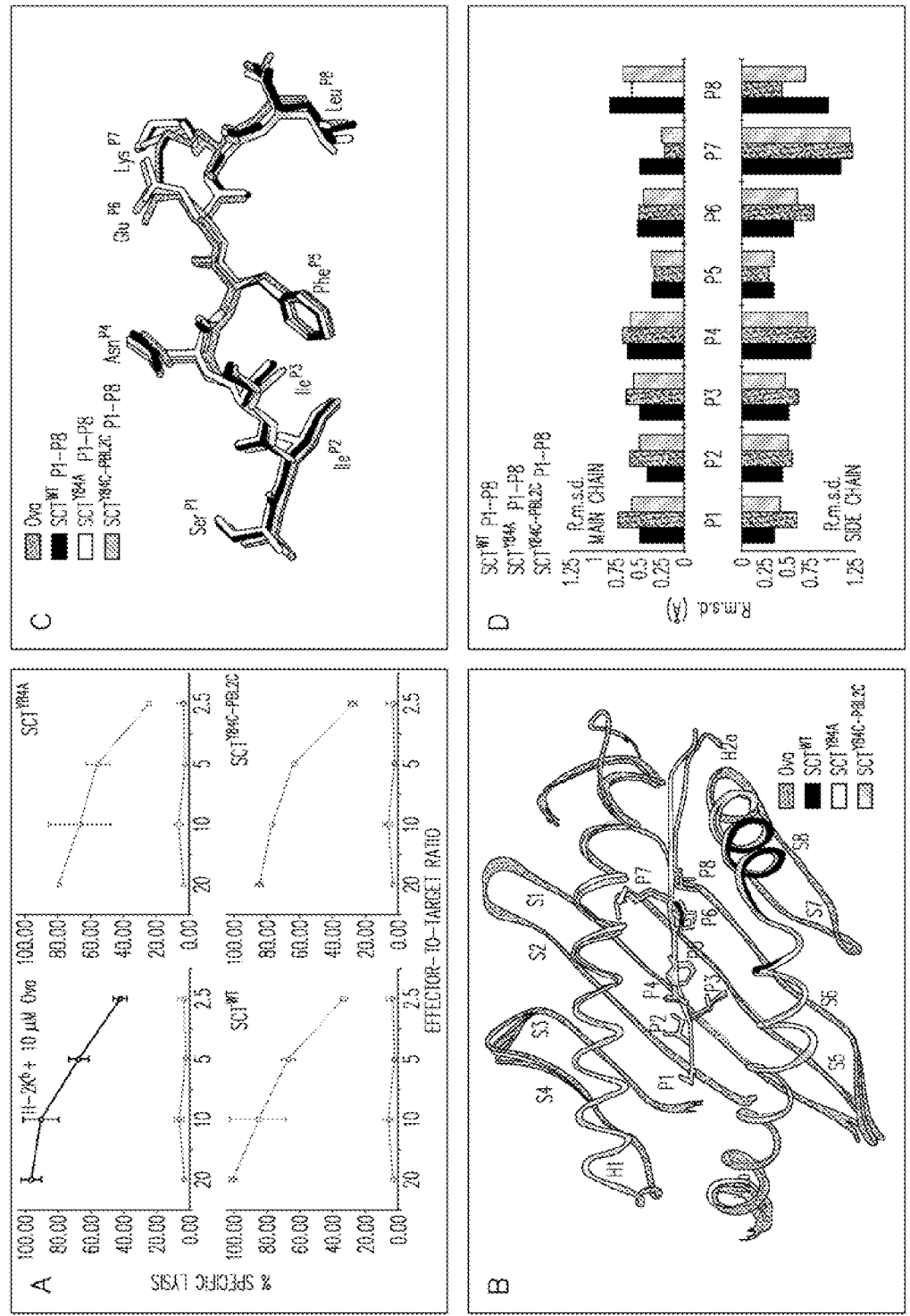

In these experiments, structural alignment of all of the atoms of α1α2 domains of the SCTs to those of native $K^b$ bound to Ova yielded overall pair-wise r.m.s.d. values of 1.14 Å (Cα r.m.s.d.=0.58 Å) for $SCT^{WT}$, 1.32 Å (Cα r.m.s.d.=0.77) for $SCT^{Y84A}$, and 1.32 (Cα r.m.s.d, 0.80) for $SCT^{Y84C-PBL2C}$ indicating that only minimal structural perturbations of the antigen presenting platform are created in each of the SCT proteins. These initial results let us to believe that each of the SCT proteins would retain their native fold in vivo and that the introduced engineering perturbations would minimally affect T cell recognition. To test this hypothesis each of the SCT constructs was introduced into the LM1.8 cell line and tested as targets in chromium-release assay against the $K^b$-Ova reactive OT-1 T cells (FIG. 8A). As we anticipated, the OT-1 T cell clone recognized efficiently each SCT construct, while it did not recognize the control LM1.8 $K^b$-transfected cells. This indicated that SCT proteins are folded properly in the ER, egress efficiently to the cell surface, and retain the native antigen recognition elements involved in TCR activation. Moreover, additional evidence presented later extends this conclusion by demonstrating that SCTs expressed as tetramers bind TCRs of polyclonal T cells in an antigen-specific manner.

To visualize any structural differences between the SCTs and native $K^b$ we aligned the main chain residues of the peptide binding platforms of all four structures and this alignment is shown as a ribbon diagram in B. Most of the main chain differences are found in solvent-exposed, flexible loops and the C-terminal regions of the α1α2 domains. Some minor differences were also seen in the C-terminal and N-terminal portions of the α1 and α2 helix, respectively with $SCT^{Y84C-PBL2C}$ showing the greatest deviation from $K^b$-Ova. In light of our functional data, however, we believe that these differences have little is any affect of TCR binding.

Figure 8D:
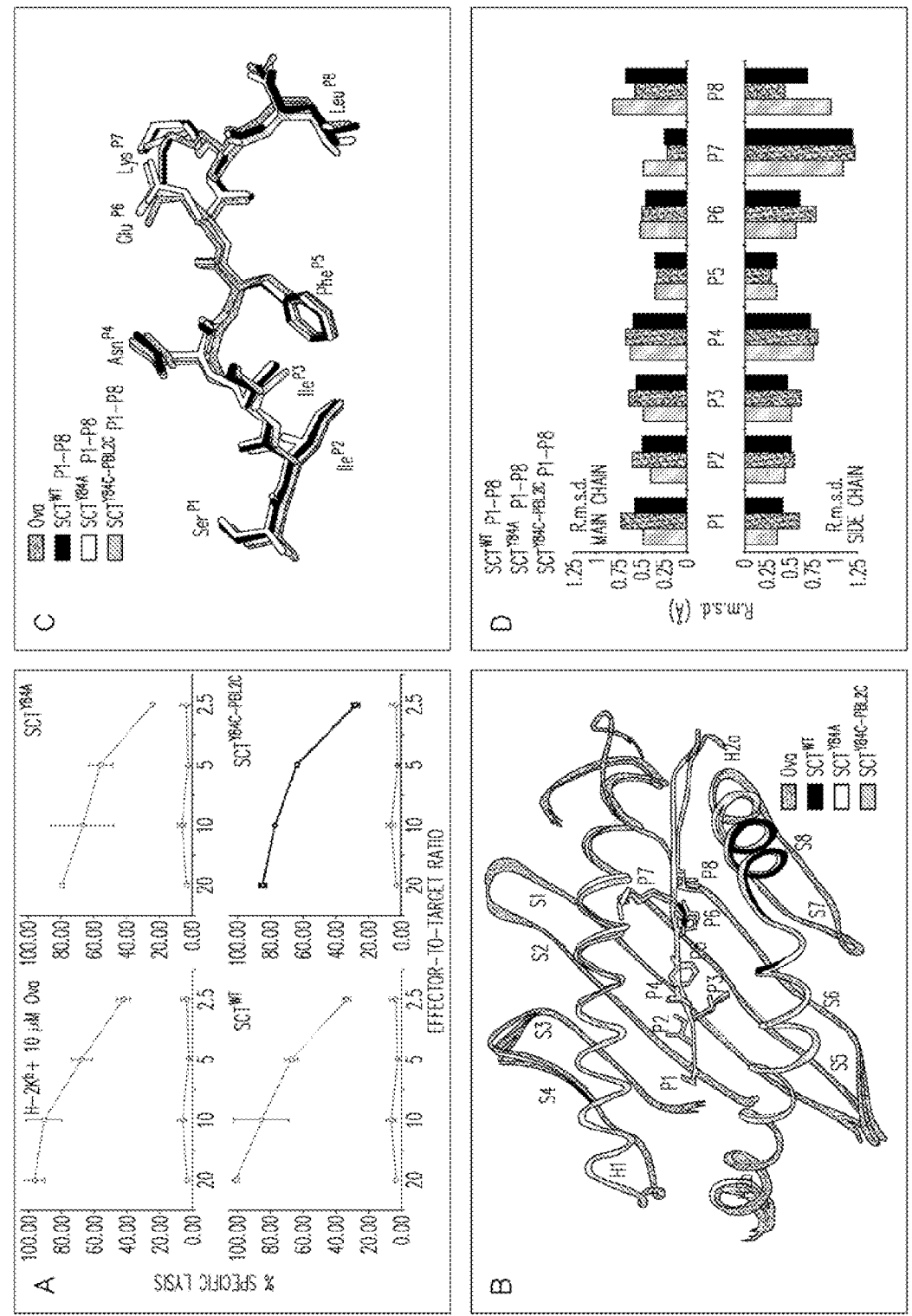
Figure 8E:
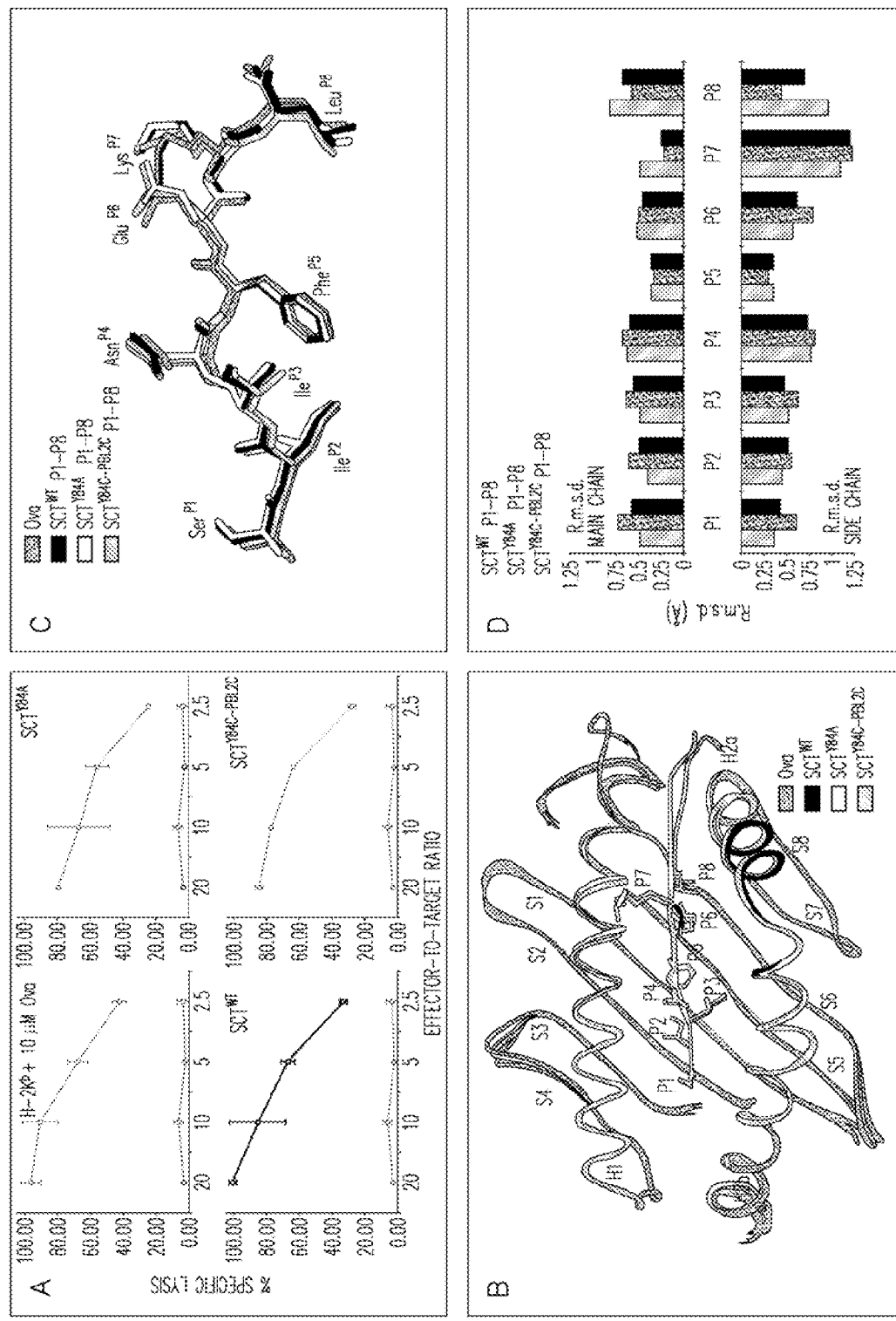
Figure 8F:
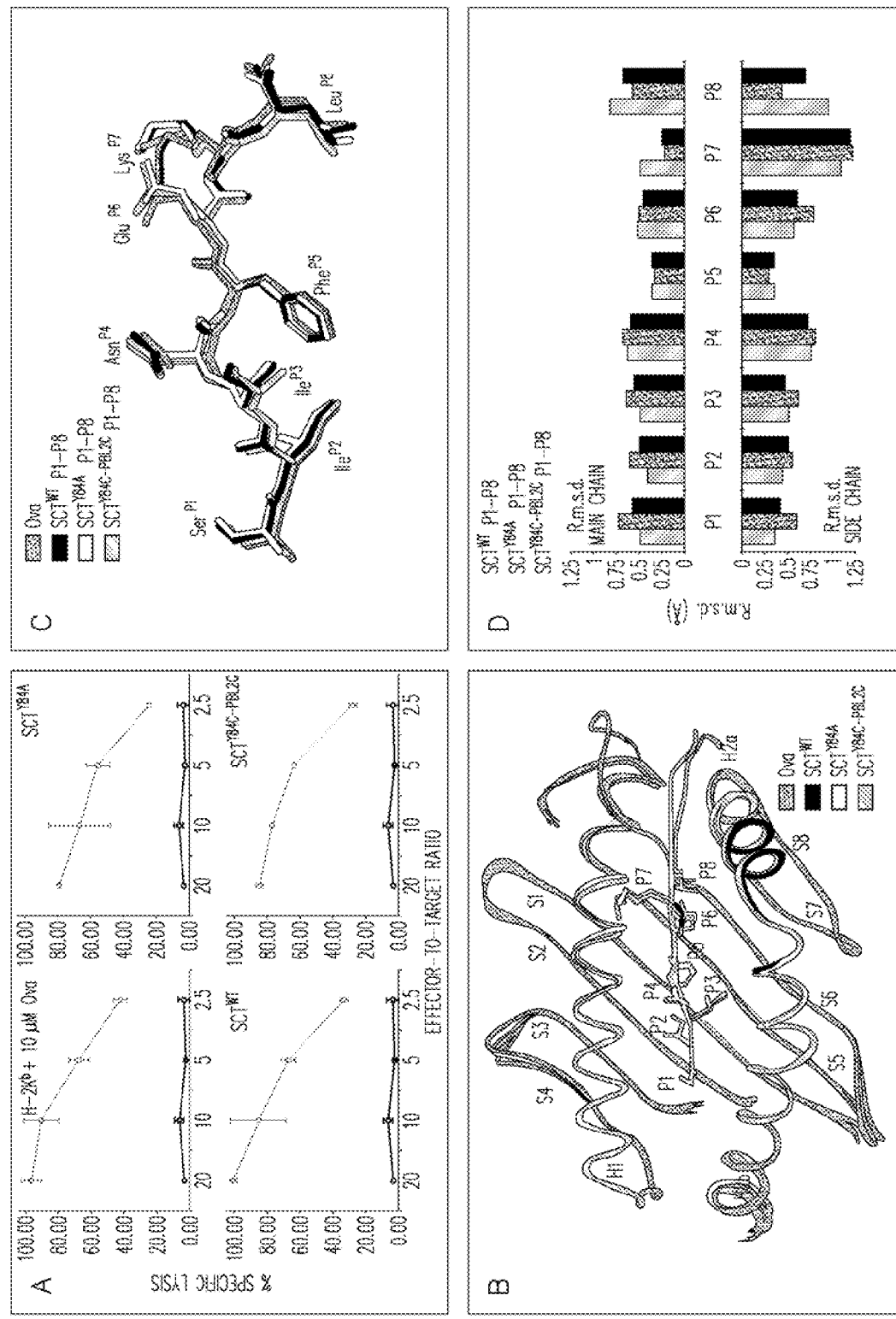
Figure 9A:
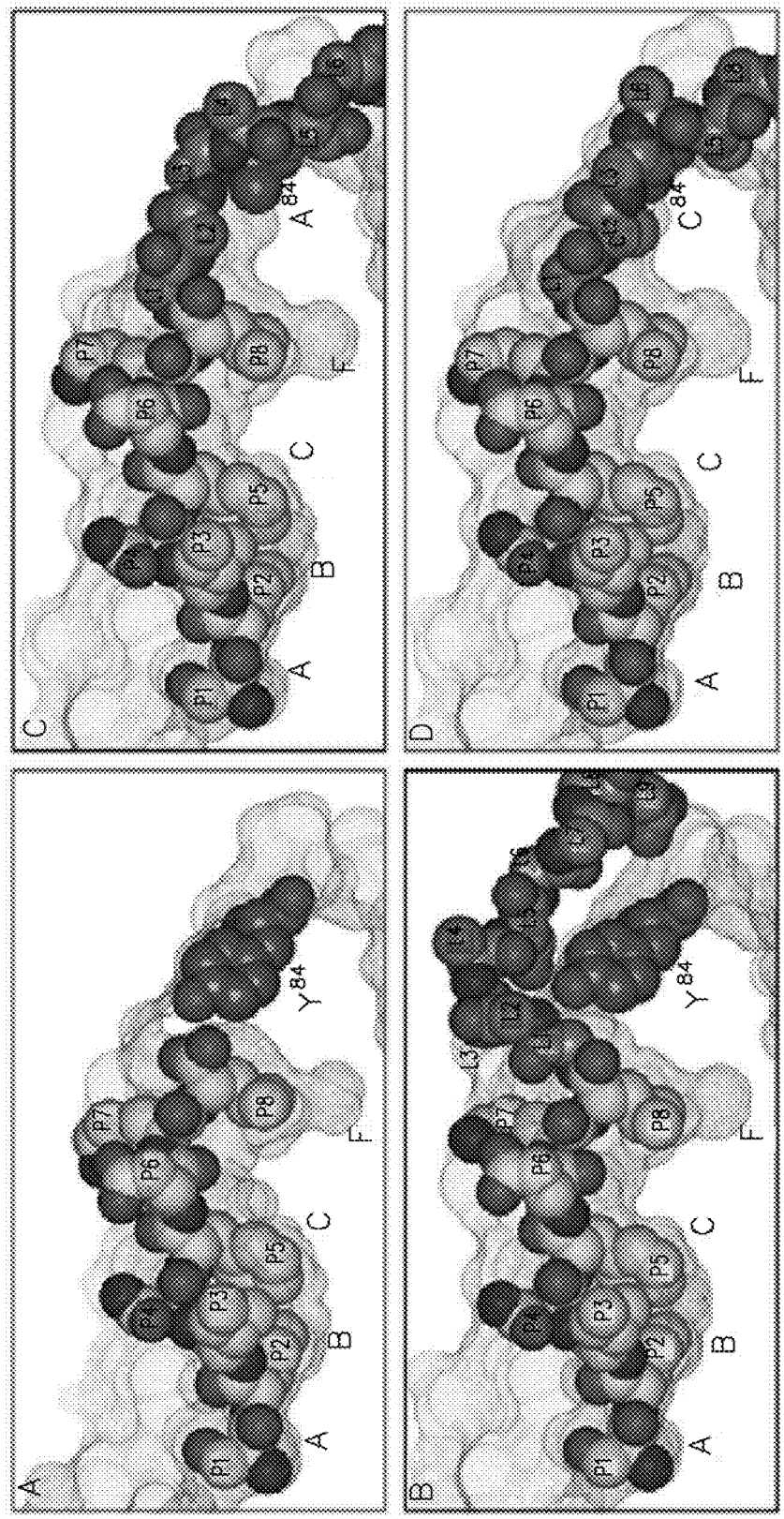
FIG. 9. Linker accommodation in each SCT protein. The solvent-accessible surfaces, of the peptide-binding grooves of $K^b$ (A), $SCT^{WT}$ (B), $SCT^{Y84A}$ (C), and $SCT^{Y84C-PBL2C}$ (D) are displayed as blue dotted surfaces. Tyr$^{84}$ in the native complex and $SCT^{WT}$, as well as Ala$^{84}$ in $SCT^{Y84A}$, and Cys$^{84}$ in $SCT^{Y84C-PBL2C}$ are depicted as CPK models and colored in light-blue. $K^b$ pocket locations are indicated underneath each surface. Note the introduction of a C-terminal channel allowing for the unconstrained exit of the linker from the $K^b$ groove as a result of the Y84A or the Y84C mutation. Adapted from original color figure; panels highlight original colors against a dimmed background.

We also compared the conformations of Ova in each of the SCT constructs to that of Ova bound to native $K^b$. FIG. 9C shows an alignment of all four peptides based on the alignment of their respective antigen-binding platforms and FIG. 8D presents a quantification of the r.m.s. deviations of the conformation of each SCT peptide from that of natively-bound Ova. Only minor differences are seen for the main chain and side chain atomic positions for the anchoring Ova residues in each of the SCT compared to $K^b$-Ova with the largest differences observed for $Val^{P8}$. Likewise, the conformations of solvent exposed. Ova residues show little differences with the largest differences seen for the side chain of $Lys^{P7}$. The pair-wise r.m.s.d. values for the alignment of each peptide to natively-bound Ova are 0.63 Å for $SCT^{WT}$, 0.65 Å for $SCT^{Y84A}$, and 0.61 Å for $SCT^{Y84C-BPL2C}$.

Example 21

This example illustrates accommodation of linker residues—MHC class I proteins typically present antigenic peptides of 8-10 residues in length. This is in part due to the confined nature of their peptide binding grooves. To engineer a class I MHC that would favorably accommodate a C-terminal peptide linker, the conserved $Tyr^{84}$ residue was mutated to an alanine to form SCT$^{Y84A}$ in order to open the K$^b$-groove. In SCT$^{Y84C\text{-}PBL2C}$ we mutated this residue to Cys to maintain the open K$^b$ groove and to establish a disulfide bridge between the MHC and a Cys residue introduced in the second linker position.

Figure 9B:
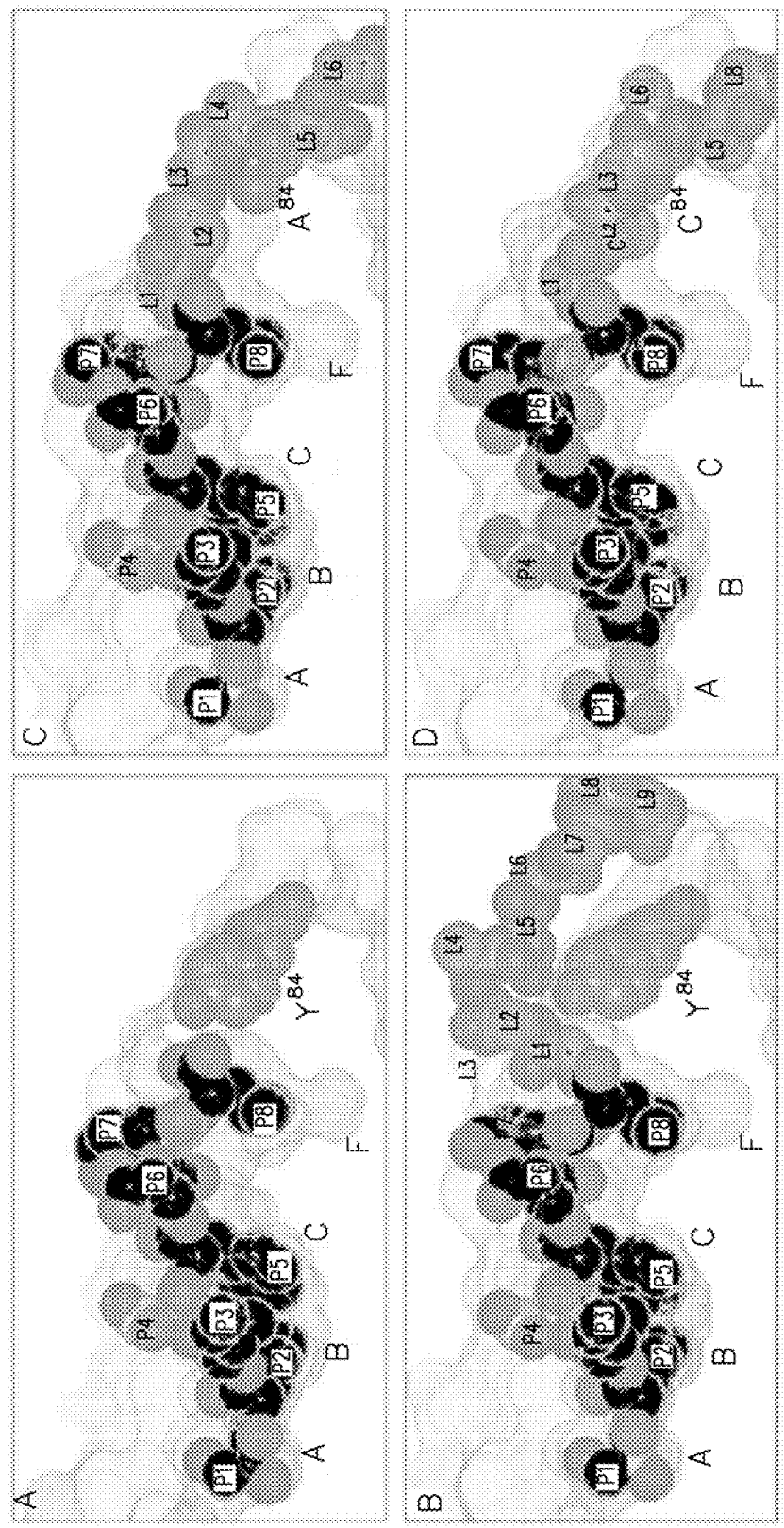
Figure 9D:
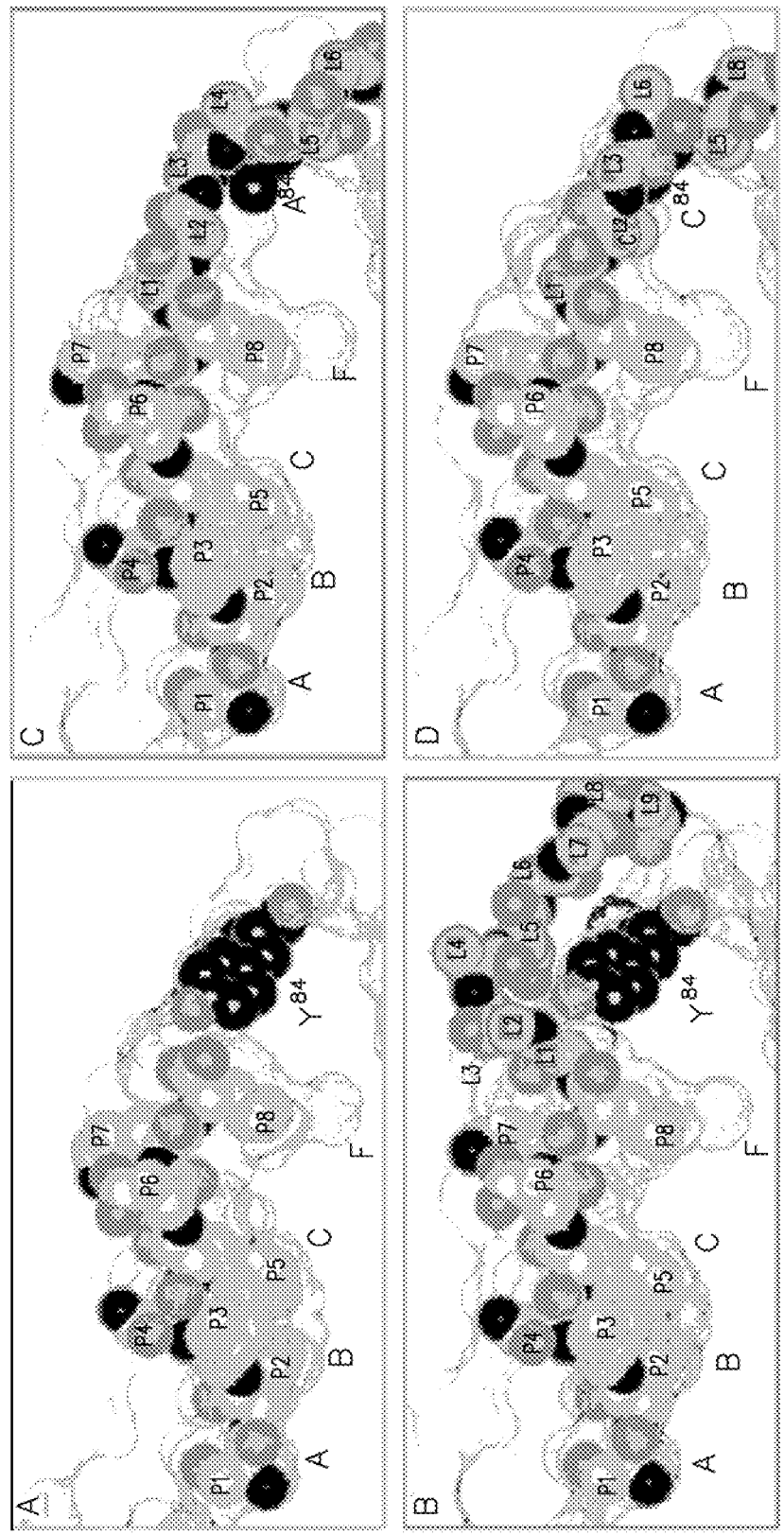
Figure 9E:
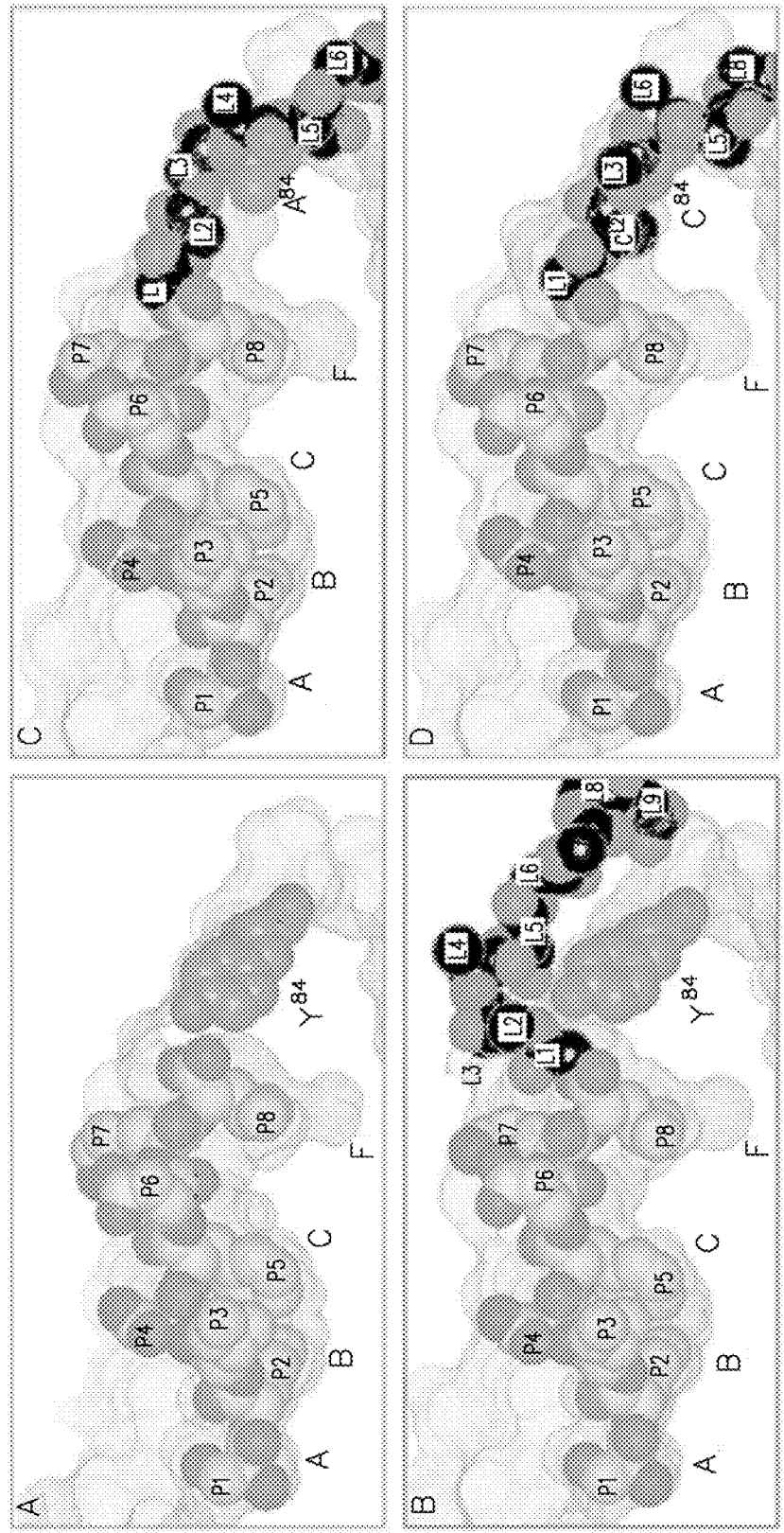
Figure 9F:
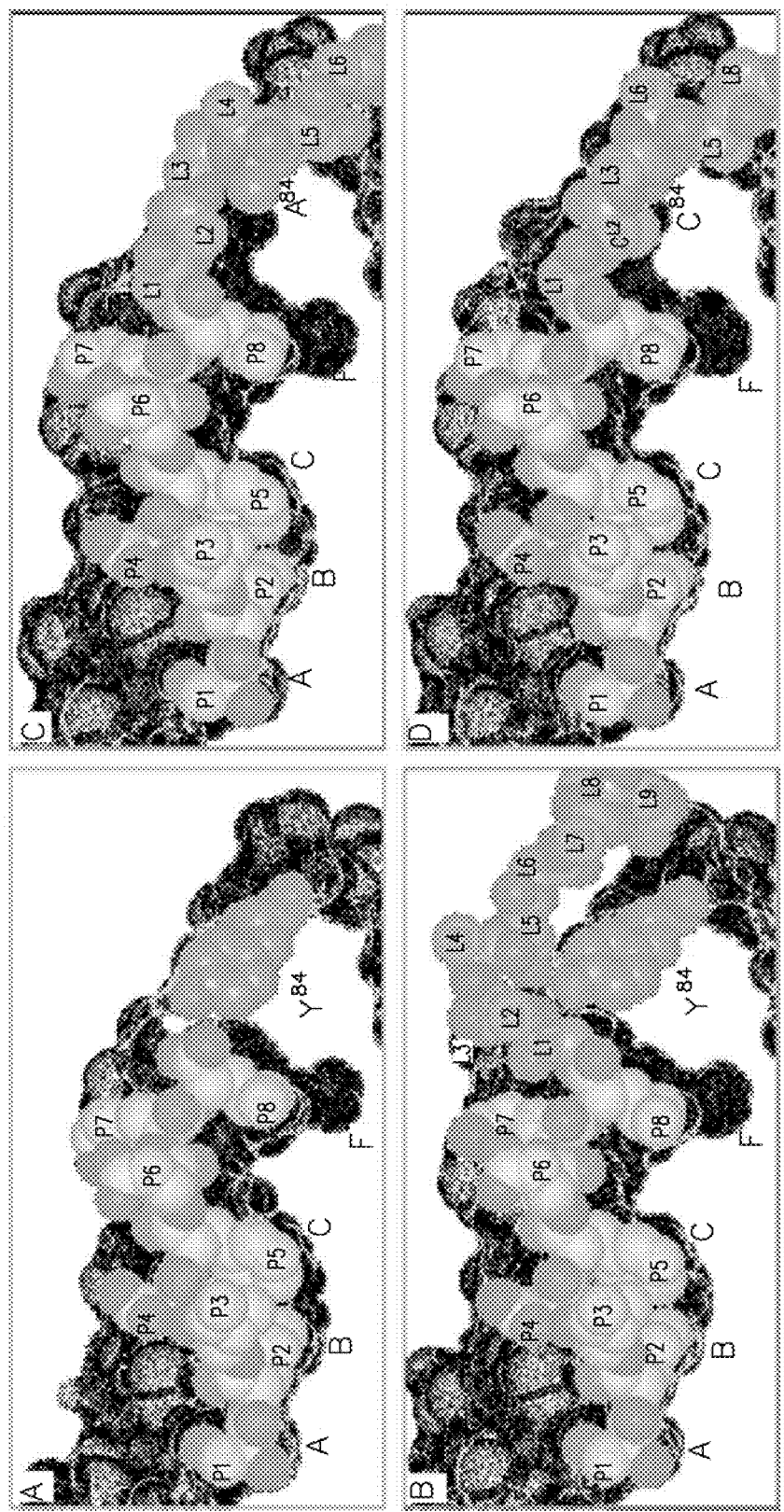
Figure 10A:
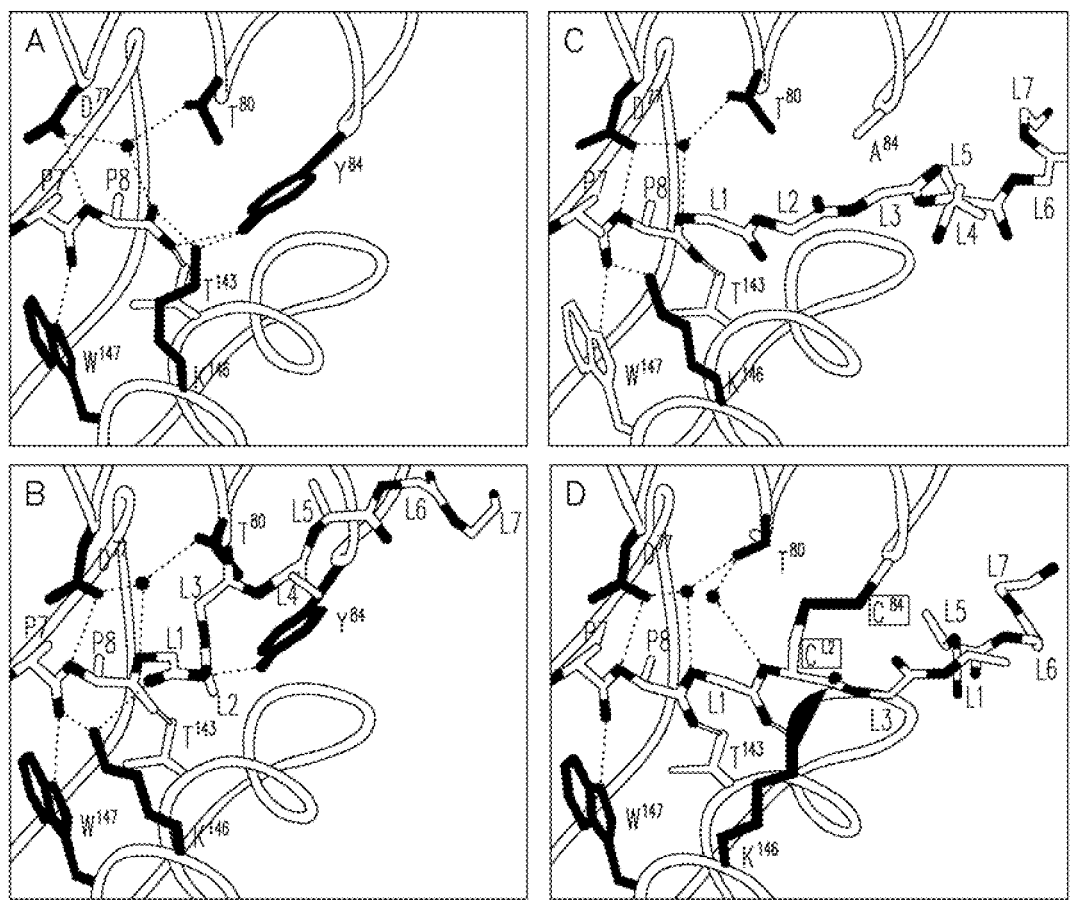
FIG. 10. Sequence-independent interactions with the Ova and PBL in each SCT at the C-terminal end of the $K^b$-groove, Heavy chain residues involved in hydrogen bonding to the main chain of Lys$^{P7}$ and Leu$^{P8}$ in $K^b$-Ova (A); Lys$^{P7}$, Leu$^{P8}$, Gly$^{PBL1}$ and Gly$^{PBL2}$ in $SCT^{WT}$ (B) and $SCT^{Y84A}$ (C); and Lys$^{P7}$, Leu$^{P8}$, Gly$^{PBL1}$ and Cys$^{PBL2}$ in $SCT^{Y84A-PBL2C}$ (D) are shown and colored in purple. Preserved hydrogen bonds are shown as small silver balls connecting atoms apart with reasonable distance and geometry, while novel ones are shown as small green balls. Preserved water molecules are colored in gray, while the additional water molecule in $SCT^{Y84C-PBL2C}$ is colored in green. The main chain traces of the peptide binding platforms are shown as thin cyan tubes. The complex is oriented as in FIG. 8B. For clarity PBL residues are labeled L1 through L7. Adapted from original color figure; panels highlight original colors against a dimmed background.
Figure 10B:
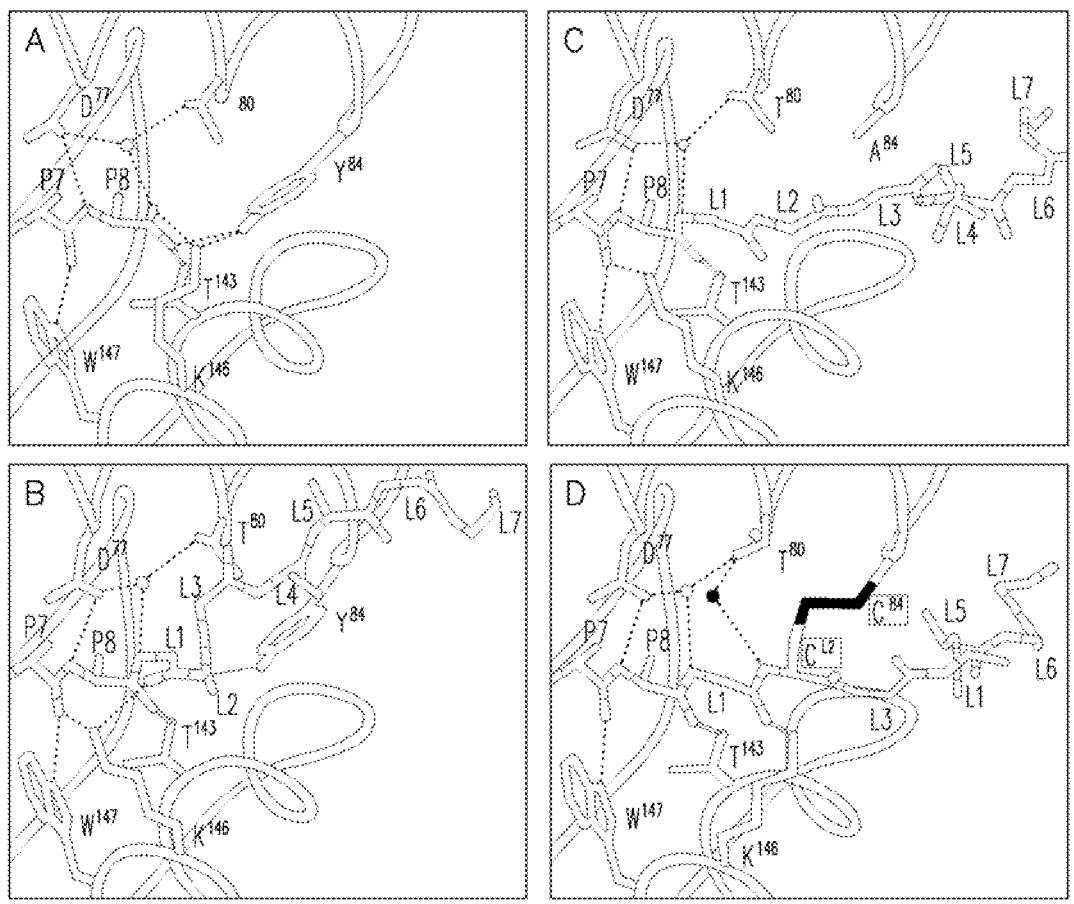
Figure 10C:
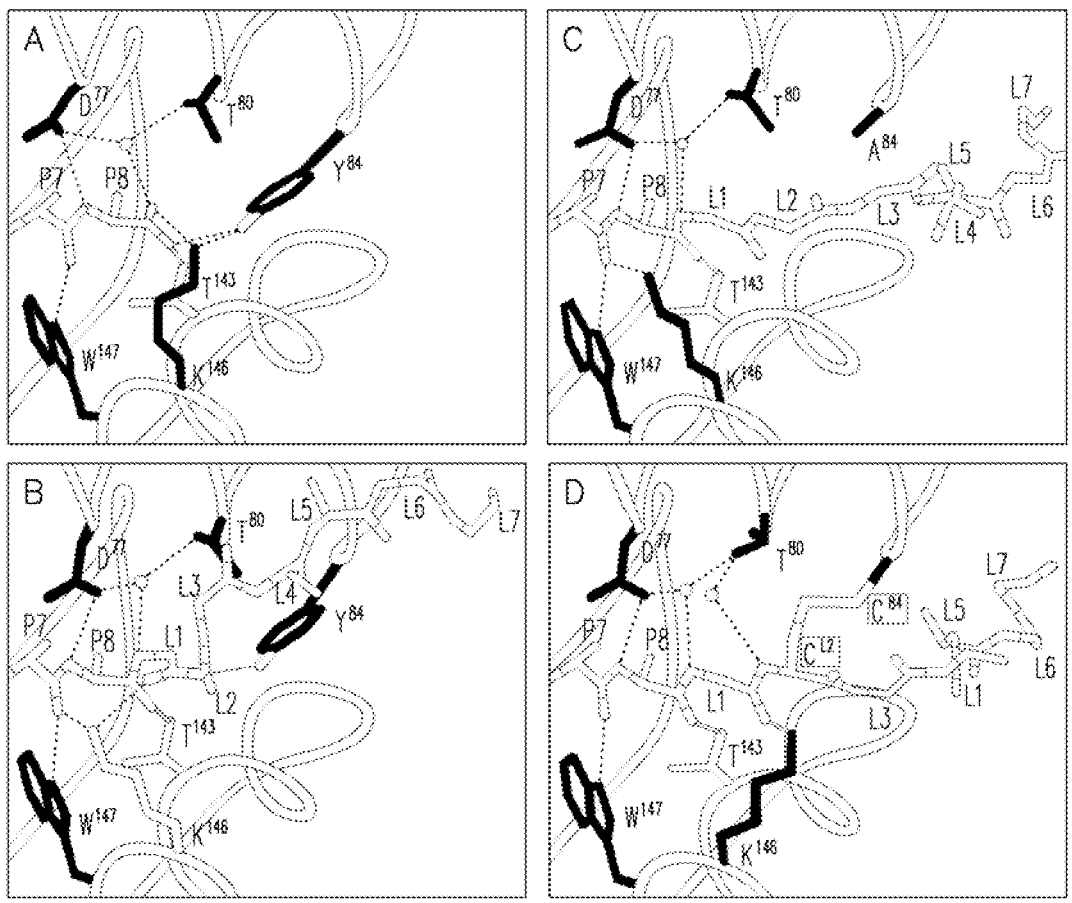
Figure 10D:
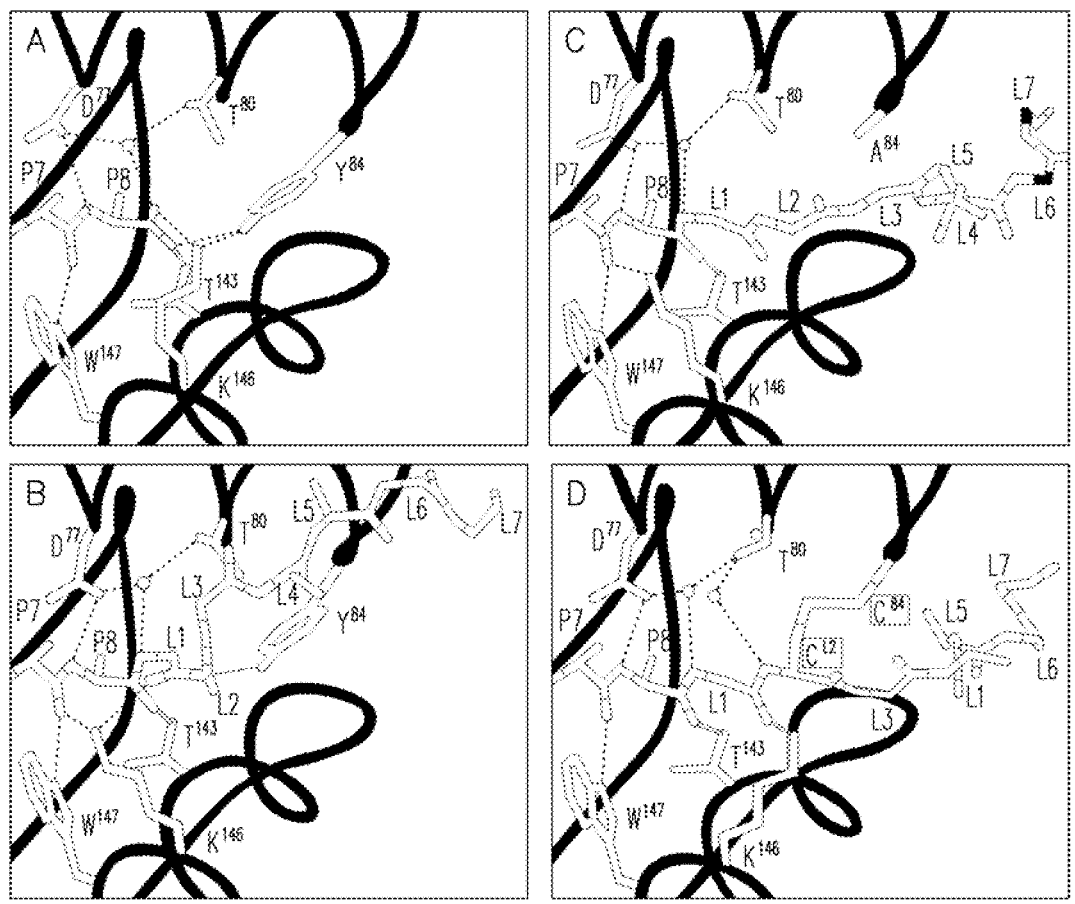
Figure 10E:
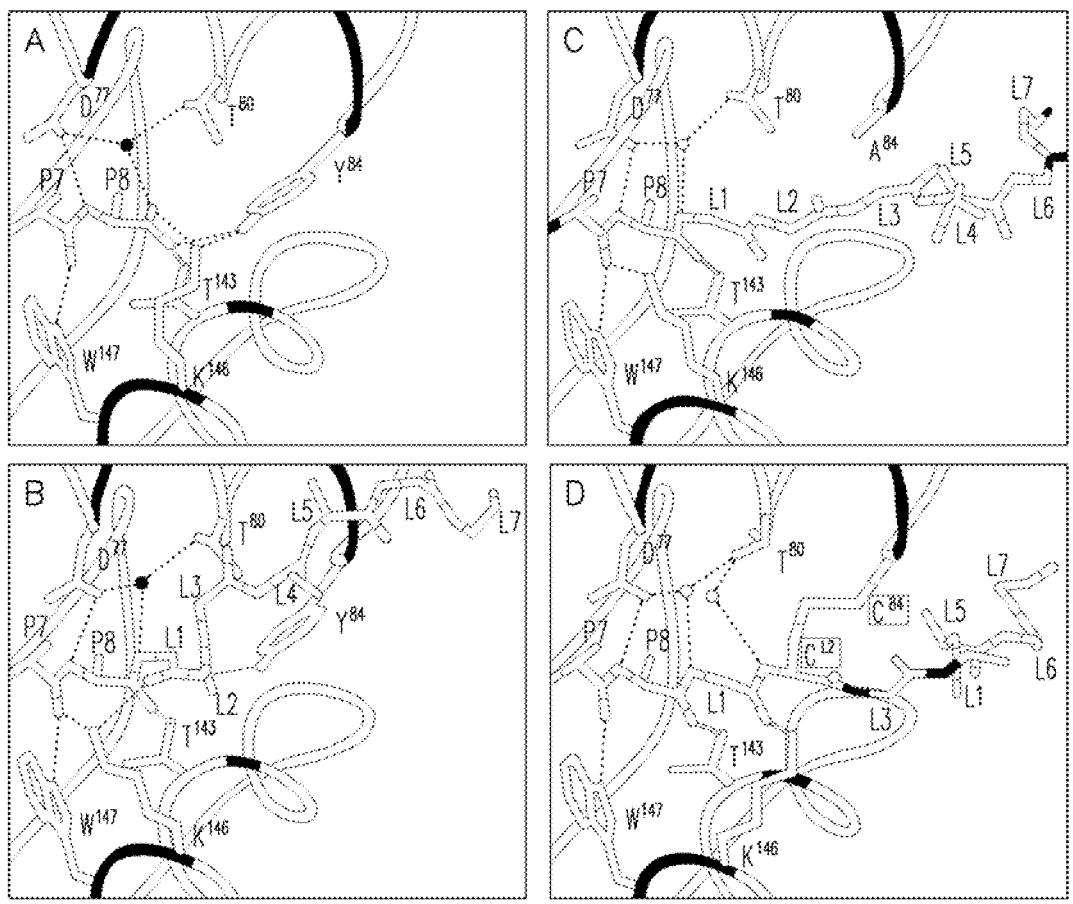

To visualize the structural changes in the binding grooves of each SCT construct we calculated solvent accessible surfaces (97) for a spherical probe with a radius of 1.4 Å for their α1α2 domains (FIGS. 9B, C, and D). For comparison the solvent, accessible surface of native K$^b$ is also shown (FIG. 9A), which reveals the way in which Tyr$^{84}$ (shown as a CPK model) closes the C-terminal end of the K$^b$ groove. In the SCT$^{WT}$ construct the peptide-β$_2$m linker adopts a near 90° turn at the P8-PBL1 peptide bond due to the obtrusive presence of Tyr$^{84}$. In this structure the linker passes over the C-terminal end of the α1 helix potentially interfering with antigen recognition events. Interestingly a similar protrusion was observed for a decamer peptide bound with its C-terminal residue outside of the binding groove of HLA-A2 as reported by Collins et al. (98). In contrast to the structure of SCT$^{WT}$, the structures of SCT$^{Y84A}$ and SCT$^{Y84C\text{-}PBL2C}$ (FIGS. 9C and D, respectively) clearly showed the creation of a channel that accommodates the peptide-β$_2$m linker away from the TCR-proximal surface of the α1 helix. Thus the K$^b$ groove opening by the Y84A and Y84C mutations not only optimized peptide MHC interactions within the SCT format but also minimized any possible steric hindrance of the linker on antigen recognition by allowing it to exit the peptide-binding platform away from putative TCR recognition elements.

Example 22

This example illustrates F-Pocket Hydrogen Bonding Interactions

One of the hallmarks of peptide binding by MHC class I proteins is the anchoring of the terminal regions of the peptide through conservative hydrogen bonding networks in the A and F pockets of the MHC (99). Since the SCT format and the mutations that we introduced could closely impact on anchoring of the C-terminus of the peptide we analyzed the bonding established in the F pockets of the SCT proteins (FIG. 10). In each SCT structure, the Gly$^{PBL1}$ amide nitrogen atom occupies nearly the same position as the terminal oxygen of native Ova. A structurally conserved water molecule, which mediates a number of hydrogen bonds between the peptide C terminus and conserved MHC residues, is present in all SCT structures. As in the native structure this water molecule is coordinated between the amide nitrogen of Gly$^{L1}$ (spatially equivalent to the terminal oxygen of Leu$^{P8}$ in the native complex), and Asp$^{77}$ and Thr$^{80}$ of the α1 helix. On the other hand Lys$^{146}$, which normally hydrogen bonds to Tyr$^{84}$ and the terminal oxygen atom of Ova adopts one of two conformations in the different SCT structures. In the SCT$^{WT}$, and SCT$^{Y84A}$ structures Lys$^{146}$ forms a hydrogen bond with the carbonyl oxygen atoms of Lys$^{P7}$, while in SCT$^{Y84C\text{-}PBL2C}$ it hydrogen bonds to the carbonyl oxygen of Gly$^{PBL1}$. Interestingly and unexpectedly, a second water molecule was located in the F pocket of SCT$^{Y84C\text{-}PBL2C}$, which is coordinated by the amide nitrogen atom of Cys$^{PBL2}$ and the Oδ1 oxygen atom of Thr$^{80}$.

Example 23

Figure 11A:
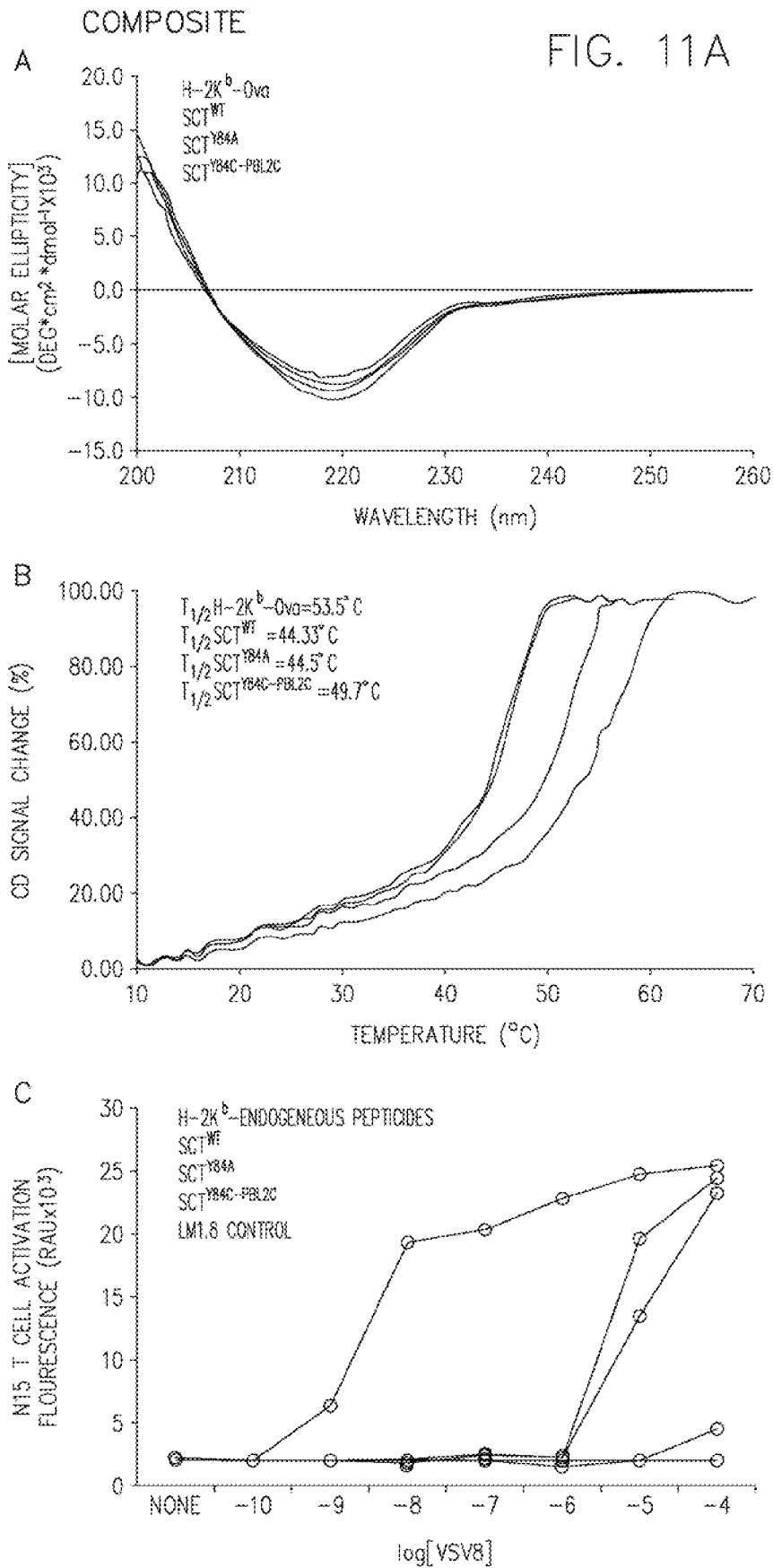
FIG. 11. Assessment of peptide-MHC association in each SCT protein. A, Far UV CD spectra of $SCT^{WT}$, $SCT^{Y84A}$, $SCT^{Y84C-PBL2C}$, and $K^b$-Ova. The measured CD signal is given as [Molar Ellipticity]$_r$, the molar ellipticity per residue. B, Thermostability as measured by CD. Increase in the CD signal at 220 nm as a function of temperature was normalized to a scale of 0 to 100. The $T_{1/2}$ for each protein is denoted in the legend. The introduction of the disulfide trap in the third SCT generation increases the observed $T_{1/2}$ by 5.2° C. C, N15 hybridoma activation to detect competitor VSV8 binding to native $K^b$ or SCT proteins. LM1.8 cells expressing the indicated constructs were incubated for 24 hours with increasing concentration of exogenous VSV8 peptide. TL-2 production was measured via proliferation of CTL L-2 cells, which was in turn detected by Alamar blue fluorescence at 590 nm. Adapted from original color figure, panels highlight original colors against a dimmed background.

This example illustrates stability of SCT$^{Y84C\text{-}PBL2C}$ over SCT$^{WT}$ and SCT$^{Y84A}$ An important goal of SCT design was to achieve a peptide-MHC assembly that is kinetically stable and resists peptide exchange by competitor peptides. Previous characterization of SCT constructs has shown that SCT$^{WT}$ proteins excluded tight-binding competitor peptides to a greater extent than native K$^b$ (10) loaded with endogenous peptides and this exclusion was enhanced by the Y84A mutation (11). However, the Ova portion of both SCT$^{WT}$ and SCT$^{Y84A}$ was competed by high concentrations of endogenous peptide. To similarly test the SCT$^{Y84C\text{-}PBL2C}$ protein, exogenous peptide binding to this construct was monitored by using a gain of recognition T cell assay (FIG. 11C). For this assay, a T cell hybridoma was used that expresses the N15 TCR specific for K$^b$-VSV8 complex (38, 39). The N15 hybridoma was readily activated when cells expressing K$^b$ were fed $10^{-9}$ M exogenous VSV8 peptide. On the order of $10^{-5}$ M VSV8 peptide was required to displace the Ova moiety from SCT$^{WT}$ and SCT$^{Y84A}$ proteins, although the latter was somewhat more refractory as previously noted (11). In contrast, $10^{-4}$ M of competitor VSV8 were unable to displace the disulfide-trapped Ova moiety from SCT$^{Y84C\text{-}PBL2C}$ protein (FIG. 11C). These results clearly show that the SCT$^{Y84C\text{-}PBL2C}$ protein forms an assembly in which the disulfide trap effectively prevents peptide dissociation. It is worth noting that the Ova peptide binds K$^b$ with a relatively high affinity. Thus a SCT incorporating Ova is highly efficient at excluding exogenous peptide even without the disulfide trap (FIG. 11C). In contrast the consequences of introducing a disulfide trap into an SCT with a relatively low affinity peptide are much more pronounced.

Figure 11B:
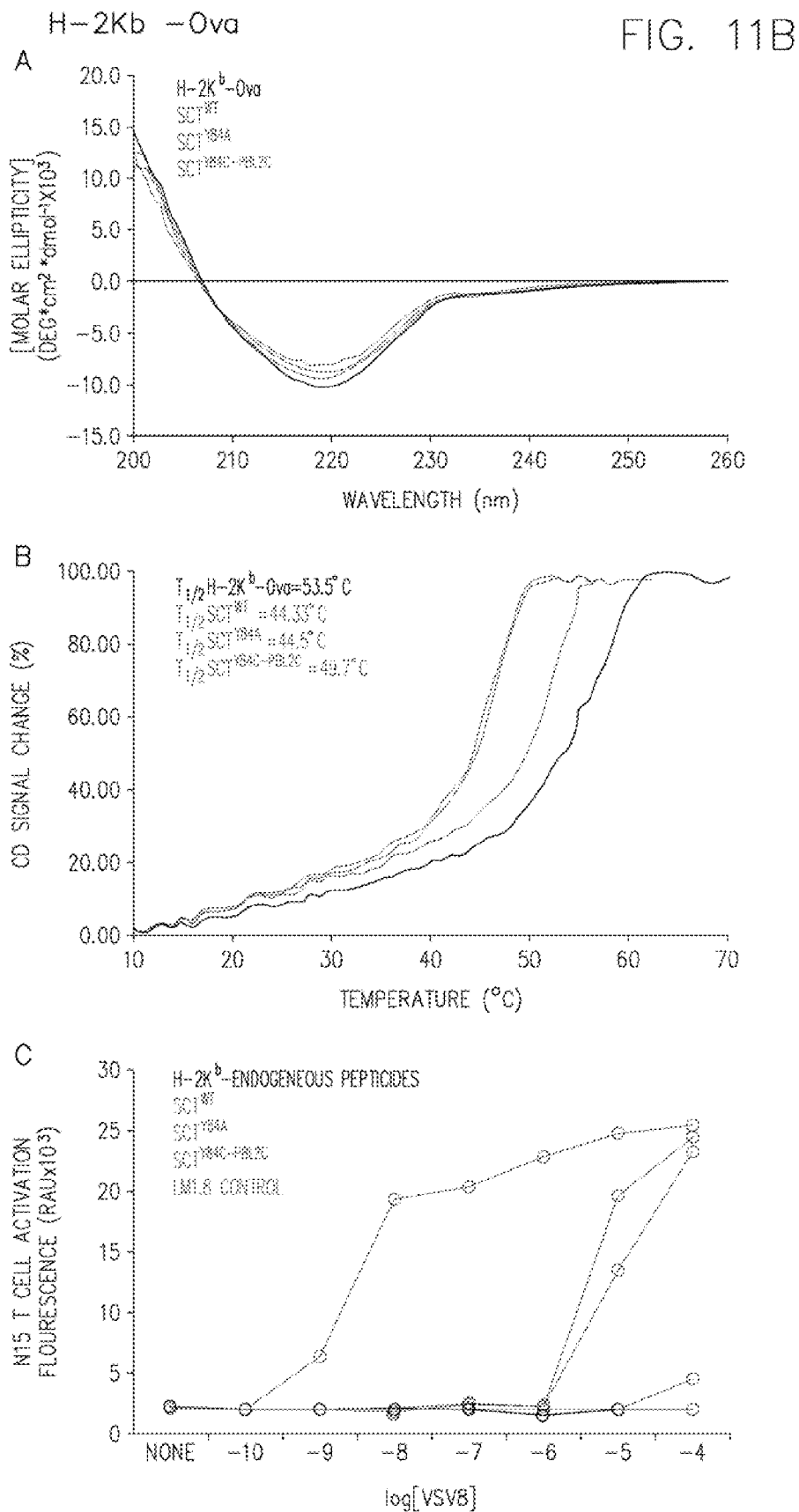
Figure 11D:
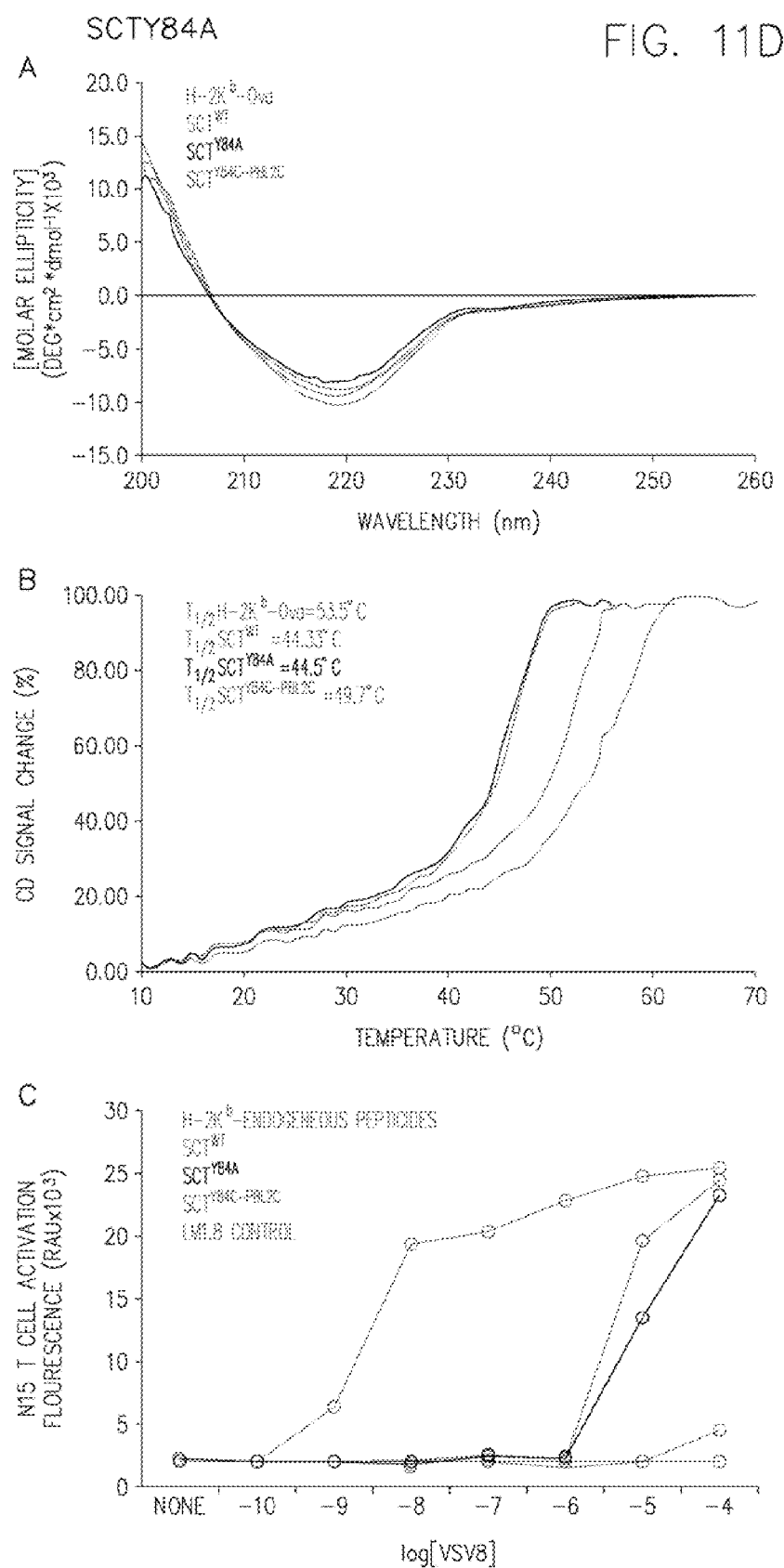
Figure 11E:
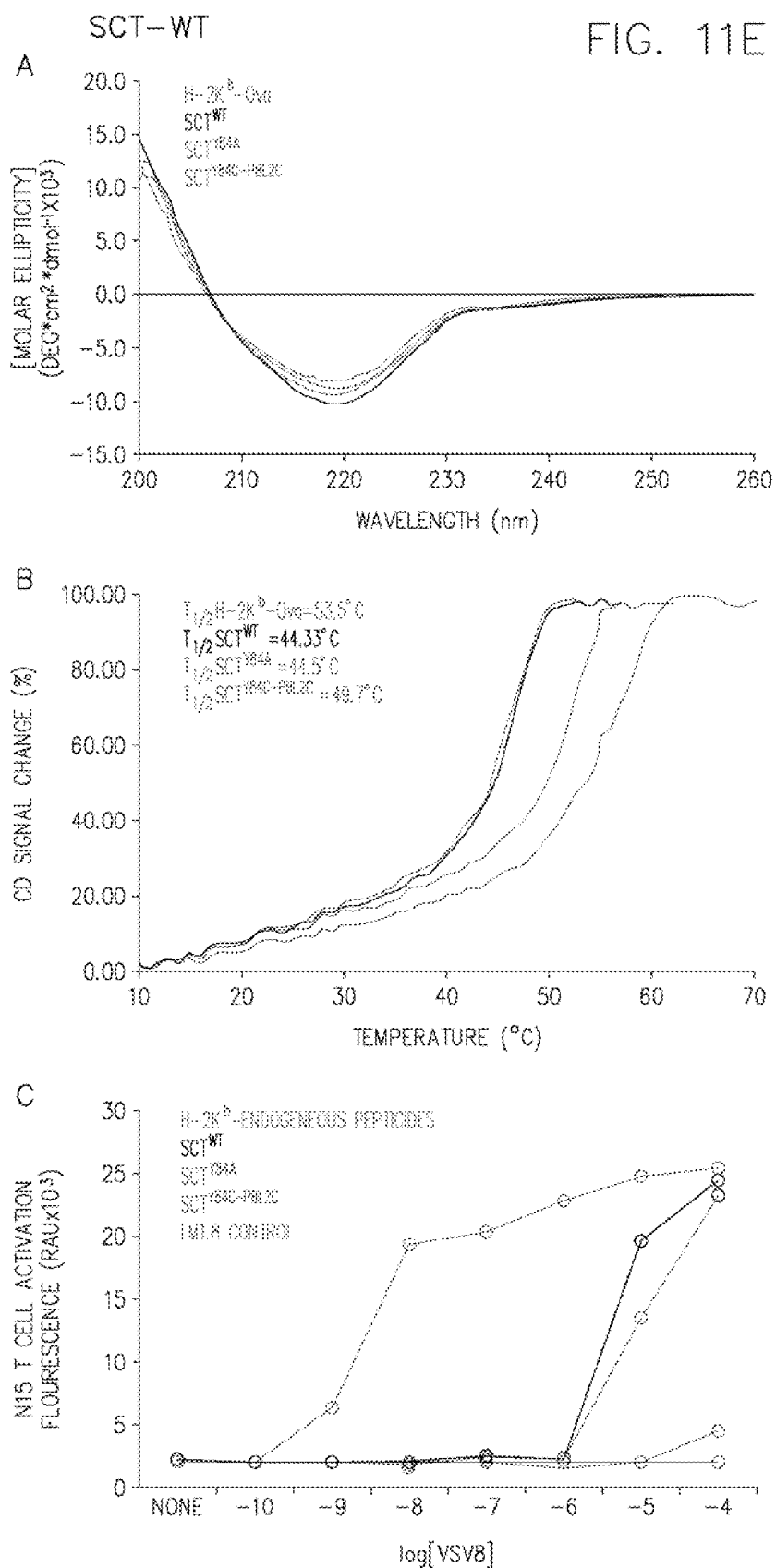

We also tested the thermostability of purified, recombinant SCTs by following their denaturation profiles as a function of temperature using CD spectroscopy (FIG. 11B). All SCT proteins had $T_{1/2}$ values (temperature at which the change in the CD signal is ½ of the total change) greater than 37° C., supporting the observation that they are all stable under physiological conditions (FIG. 12B). Reproducibly higher $T_{1/2}$ values were observed for the SCT$^{Y84C\text{-}PBL2C}$ protein (49.7° C.) when compared with those of SCT$^{WT}$ and SCT$^{Y84A}$ (44.3° C. and 44.4° C., respectively). This increase in $T_{1/2}$ is equivalent to the increase in $T_{1/2}$ observed when a better anchoring residue was introduced in a peptide bound to K$^{bm8}$ (100). These data along with the peptide competition analysis clearly show an improvement in peptide anchoring and exclusion of exogenous peptides by SCT$^{Y84C\text{-}PBL2C}$ compared to the previous two SCT design generations.

Example 24

This example illustrates generation of disulfide-trapped staining reagents.

In these experiments, generation of peptide-MHC tetramers in which the peptide is permanently attached to the class I heavy chain through a disulfide trap without a β$_2$-microglobulin (β$_2$m) is demonstrated. To generate these complexes, K$^b$ heavy chain carrying the Y84C mutation and a C-terminal biotinylation sequence was refolded with β$_2$m and a modified Ova peptide. This peptide was C-terminally extended to include a Gly-Cys sequence for disulfide bridge formation analogous to the one designed in SCT$^{Y84C\text{-}PBL2C}$. The formed disulfide-trap MHC complex was purified using size exclusion and anion exchange chromatographies. The formation of the engineered disulfide was confirmed by non-reducing SDS-PAGE and electrospray mass spectrometry of the intact disulfide-trap complex, which revealed the expected masses of unattached β$_2$m and a single mass peak of the K$^b$ heavy chain disulfide bonded to the extended Ova peptide. The pure complex was biotinylated at the C-terminal end of the heavy chain by incubation with BirA ligase. This biotin-labeled product was incubated with chromophore-conjugated streptavidin to generate the staining tetramer through the tight association of streptavidin to four biotinylated MHC proteins.

To demonstrate the feasibility and validity of the disulfide-trap tetramers, we tested their T cell binding specificity. The disulfide-trap tetramers were compared directly with conventional $K^b$-Ova tetramers at the same molar concentration of MHC. First, we confirmed tetramer binding to T cells from OT-1 transgenic mice (FIG. 12A).

Example 25

This example illustrates that T cells that respond to the native class I complex also recognize the disulfide bond engineered class I tetramers.

In these experiments, B6 mice were, infected with a strain of *Listeria monocytogenes* that expresses ovalbumin. During this infection the mice mount a vigorous response in which a large fraction (5-10%) of CD8 T are specific for the Ova peptide presented by $K^b$ (101). To determine the extent of overlap in CD8 T cell populations that recognize each type of MHC complex, tetramers of both conventional and disulfide-trap configurations were used to stain splenocytes from infected mice (FIG. 12B). We found that similar numbers of CD8 T cells were detected by each tetramer alone. More significantly, when conventional and disulfide-trap tetramers linked to different fluorophores were used to stain simultaneously B6 splenocytes, the same subset of antigen-specific T cells bound both tetramers. These results indicate that the engineered disulfide bond can be used to make more stable tetramers that accurately enumerate pathogen-specific T cells.

REFERENCES

1. Yewdell, J. W., and J. R. Bennink. 1999. Immunodominance in major histocompatibility complex class I-restricted T lymphocyte responses. Annu Rev Immunol 17:51.
2. Connolly, J. M. 1994. The peptide p2Ca is immunodominant in allorecognition of Ld by beta chain variable region V beta 8+ but not V beta 8− strains. Proc Natl Acad Sci USA 91:11482.
3. La Gruta, N. L., K. Kedzierska, K. Pang, R. Webby, M. Davenport, W. Chen, S. J. Turner, and P. C. Doherty. 2006. A virus-specific CD8+ T cell immunodominance hierarchy determined by antigen dose and precursor frequencies. Proc Natl Acad Sci USA 103:994.
4. Huang, C. H., S. Peng, L. He, Y. C. Tsai, D. A. Boyd, T. H. Hansen, T. C. Wu, and C. F. Hung. 2005. Cancer immunotherapy using a DNA vaccine encoding a single-chain trimer of MHC class I linked to an HPV-16 E6 immunodominant CTL epitope. Gene Ther. 12: 1180.
5. Yewdell, J. W., and M. Del Val. 2004. Immunodominance in TCD8+ responses to viruses; cell biology, cellular immunology, and mathematical models. Immunity 21:149.
6. Altman, J. D., P. A. H. Moss, P. J. R. Goulder, D. H. Barouch, M. G. McHeyzer-Williams, J. I. Bell, A. J. McMichael, and M. M. Davis. 1996. Phenotypic Analysis of Antigen-Specific T Lymphocytes, Science 274:94.
7. Fu, T. M., A. Friedman, J. B. Ulmer, M. A. Liu, and J. J. Donnelly. 1997. Protective cellular immunity: cytotoxic T-lymphocyte responses against dominant and recessive epitopes of influenza virus nucleoprotein induced by DNA immunization. J Virol 71:2715.
8. Chen, Y., R. G. Webster, and D. L. Woodland. 1998. Induction of CD8+ T cell responses to dominant and subdominant epitopes and protective immunity to Sendai virus infection by DNA vaccination. J Immunol 160:2425.
9. van der Most, R. G., K. Murali-Krishna, J. L. Whitton, C. Oseroff, J. Alexander, S. Southwood, J. Sidney, R. W. Chesnut, A. Sette, and R. Ahmed. 1998. Identification of Db- and Kb-restricted subdominant cytotoxic T-cell responses in lymphocytic choriomeningitis virus-infected mice. Virology 240:158.
10. Yu, Y. Y., N. Netuschil, L. Lybarger, J. M. Connolly, and T. H. Hansen. 2002, Cutting edge: single-chain trimers of MHC class I molecules form stable structures that potently stimulate antigen-specific T cells and B cells. J Immunol 168:3145.
11. Lybarger, L., Y. Y, Yu, M. J. Miley, D. H. Fremont, N. Myers, T. Primeau, S. M. Truscott, J. M. Connolly, and T. H. Hansen. 2003, Enhanced immune presentation of a single-chain major histocompatibility complex class I molecule engineered to optimize linkage of a C-terminally extended peptide. J Biol Chem 278:27105.
12. Chen, W., S. Khilko, J. Fecondo, D. H. Margulies, and J. McCluskey, 1994. Determinant selection of major histocompatibility complex class I-restricted antigenic peptides is explained by class I-peptide affinity and is strongly influenced by nondominant anchor residues. J Exp Med 180: 1471.
13. Primeau, T., N. B. Myers, Y. Y. Yu, L. Lybarger, X. Wang, S. M. Truscott, T. H. Hansen, and J. M. Connolly. 2005. Applications of major histocompatibility complex class I molecules expressed as single chains. Immunol Res 32:109.
14. Beck, J. C., T. H. Hansen, S. E. Cullen, and D. R. Lee. 1986. Slower processing, weaker beta 2-M association, and lower surface expression of H-2Ld are influenced by its amino terminus. J Immunol 137:916.
15. Lie, W. R., N. B. Myers, J. Gorka, R. J. Rubocki, J. M. Connolly, and T. H. Hansen. 1990. Peptide ligand-induced conformation and surface expression of the Ld class I MHC molecule. Nature 344:439.
16. Jaramillo, A., K. Narayanan, L. G. Campbell, N. D. Benshoff, L. Lybarger, T. H. Hansen, T. P. Fleming, J. R. Dietz, and T. Mohanakumar. 2004. Recognition of HLA-A2-restricted mammaglobin-A-derived epitopes by CD8+ cytotoxic T lymphocytes from breast cancer patients. Breast Cancer Res Treat 88:29,
17. Kim, S., et al. Nature 436, 709-713, 2005.
18. Crew, M. D., M. J. Cannon, B. Phanavanh, and C. N. Garcia-Borges, 2005. An HLA-E single chain trimer inhibits human NK cell reactivity towards porcine cells. Mol Immunol 42:1205.
19. Choudhuri, K., D. Wiseman, M. H. Brown, K. Gould, and P. A. van der Merwe. 2005. T-cell receptor triggering is critically dependent on the dimensions of its peptide-MHC ligand. Nature 436:578.
20. Lybarger, L., X. Wang, M. R. Harris, H. W. t. Virgin, and T. H. Hansen, 2003. Virus subversion of the MHC class I peptide-loading complex, immunity 18:121.
21. Pretell, J., R. S. Greenfield, and S. S. Tevethia. 1979. Biology of simian virus 40 (SV40) transplantation antigen (TrAg). V In vitro demonstration of SV40 TrAg in SV40 infected nonpermissive mouse cells by the lymphocyte mediated cytotoxicity assay. Virology 97:32.
22. Jaulin, C., P. Romero, I. F. Luescher, J. L. Casanova, A. Prochnicka-Chalufour, P. Langlade-Demoyen, J. L. Maryanski, and P. Kourilsky. 1992. Most residues on the floor of the antigen binding site of the class I MHC molecule H-2Kd influence peptide presentation. Int Immunol 4:943, 23. Hammerling, G. J., E. Rusch, N. Tada, S. Kimura, and U. Hammerling. 1982. Localization of allodeterminants on H-2Kb antigens determined with monoclonal antibodies and H-2 mutant mice. Proc Natl Acad Sci USA 79:4737.
24. Porgador, A., J. W. Yewdell, Y. Deng, J. R. Bennink, and R. N. Germain. 1997. Localization, quantitation, and in situ detection of specific peptide-MHC class I complexes using a monoclonal antibody. Immunity 6:715,
25. Yu, Y. Y., et al., Int Immunol 11:1897-1906, 1999.
26. Carbone, F. R., and M. J. Bevan. 1989. Induction of ovalbumin-specific cytotoxic T cells by in vivo peptide immunization. J Exp Med 169:603.
27. Udaka, K., K. H. Wiesmuller, S. Kienle, G. Jung, and P. Walden. 1996. Self-MHC-restricted peptides recognized by an alloreactive T lymphocyte clone. J Immunol 157: 670.
28. Van Sleek, G. M, and S. G. Nathenson. 1990. Isolation of an endogenously processed immunodominant viral peptide from the class I H-2Kb molecule. Nature 348:213,
29. Udaka, K., T. J. Tsomides, and H. N. Eisen. 1992. A naturally occurring peptide recognized by alloreactive CD8+ cytotoxic T lymphocytes in association with a class I MHC protein. Cell 69:989.
30. Udaka, K., T. J. Tsomides, P. Walden, N. Fukusen, and H. N. Eisen. 1993. A ubiquitous protein is the source of naturally occurring peptides that are recognized by a CD8+ T-cell clone. Proc Natl Acad Sci USA 90:11272.
31. Sykulev, Y., A. Brunmark, T. J. Tsomides, S. Kageyama, M. Jackson, P. A. Peterson, and H. N. Eisen. 1994. High-affinity reactions between antigen-specific T-cell receptors and peptides associated with allogeneic and syngeneic major histocompatibility complex class I proteins. Proc Natl Acad Sci USA. 91:11487.
32. Reddehase, M. J., et al., Nature 337: 651-653, 1989.
33. Wang, X., R. Connors, M. R. Harris, T. H. Hansen, and L. Lybarger. 2005. Requirements for the selective degradation of endoplasmic reticulum-resident major histocompatibility complex class I proteins by the viral immune evasion molecule mK3. J Virol 79:4099.
34. Holler, P. D., P. O. Holman, E. V. Shusta, S. O'Herrin, K. D. Wittrup, and D. M. Kranz. 2000. In vitro evolution of a T cell receptor with high affinity for peptide/MHC. Proc Natl Acad Sci USA 97:5387.
35. Holler, P. D., A. R. Lim, B. K. Cho, L. A. Rund, and D. M. Kranz. 2001. CD8(–) T cell transfectants that express a high affinity T cell receptor exhibit enhanced peptide-dependent activation. J Exp Med 194:1043.
36. Holler, P. D., L. K. Chlewicki, and D. M. Kranz. 2003. TCRs with high affinity for foreign pMHC show self-reactivity. Nat Immunol 4:55.
37. Harris, M. R., et al., Int'l. Immunol. 13: 1275-1282, 2001.
38. Letourneur, F., and B. Malissen. 1989. Derivation of a T cell hybridoma variant deprived of functional T cell receptor alpha and beta chain transcripts reveals a nonfunctional alpha-mRNA of BW5147 origin. Eur J Immunol 19:2269.
39. Chang, H. C., A. Smolyar, R. Spoerl, T. Witte, Y. Yao, E. C. Goyarts, S. G. Nathenson, and E. L. Reinherz. 1997. Topology of T cell receptor-peptide/class I MHC interaction defined by charge reversal complementation and functional analysis. J Mol Biol 271:278.
40. Hogquist, K. A., S. C. Jameson, W. R. Heath, J. L. Howard, M. J. Bevan, and F. R. Carbone. 1994. T cell receptor antagonist peptides induce positive selection. Cell 76:17.
41. Fremont, D. H., E. A. Stura, M. Matsumura, P. A. Peterson, and I. A. Wilson. 1995. Crystal structure of an H-2Kb-ovalbumin peptide complex reveals the interplay of primary and secondary anchor positions in the major histocompatibility complex binding groove. Proc Natl Acad Sci USA 92:2479.
42. Kersh, G. J., M. J. Miley, C. A. Nelson, A. Grakoui, S. Horvath, D. L. Donermeyer, J. Kappler, P. M. Allen, and D. H. Fremont. 2001. Structural and functional consequences of altering a peptide MHC anchor residue. J Immunol 166:3345.
43. Kozono, H., J. White, J. Clements, P. Marrack, and J. Kappler. 1994. Production of soluble MHC class II proteins with covalently bound single peptides. Nature 369:151.
44. Fremont, D. H., W. A. Hendrickson, P. Marrack, and J. Kappler, 1996. Structures of an MHC class II molecule with covalently bound single peptides. Science 272:1001.
45. Messaoudi, I., J. LeMaoult, and J. Nikolic-Zugic. 1999. The mode of ligand recognition by two peptide MHC class I-specific monoclonal antibodies. J Immunol 163:3286.
46. Oliver, J. D., F. J. van der Wal, N. J. Bulleid, and S. High. 1997. Interaction of the Thiol-Dependent Reductase ERp57 with Nascent Glycoproteins. Science 275:86.
47. Molinari, M. and A. Helenius. 1999. Glycoproteins form mixed disulphides with oxidoreductases during folding in living cells. Nature 402:90,
48. Cresswell, P., B. Aranachalam, N. Bangia, T. Dick, G. Diedrich, E. Hughes, and M. Maric. 1999, Thiol oxidation and reduction in MHC-restricted antigen processing and presentation. Immunol Res 19:191.
49. Karttunen, J., S. Sanderson, and N. Shastri. 1992. Detection of rare antigen-presenting cells by the lacZ T-cell activation assay suggests an expression cloning strategy for T-cell antigens. Proc Natl Acad Sci USA 89:6020.
50. Howarth, M., A. Williams, A. B Tolstrup, and T. Elliott. 2004. Tapasin enhances MHC class I peptide presentation according to peptide half-life. Proc Natl Acad Sci USA 101:11737.
51. Lipford, G. B., S. Bauer, H. Wagner, and K. Heeg. 1995. In vivo CTL induction with point-substituted ovalbumin peptides: immunogenicity correlates with peptide-induced MHC class I stability. Vaccine 13:313.
52. Saito, Y., P. A. Peterson, and M. Matsumura, 1993. Quantitation of peptide anchor residue contributions to class I major histocompatibility complex molecule binding. J Biol Chem 268:2.1309.
53. Balendiran, G. K., J. C. Solheim, A. C. Young, T. H. Hansen, S. G. Nathenson, and J. C. Sacchettini. 1997. The three-dimensional structure of an H-2Ld-peptide complex explains the unique interaction of Ld with beta-2 microglobulin and peptide. Proc Natl Acad Sci USA 94:6880.
54. Lie, W. R., N. B. Myers, J. M. Connolly, J. Gorka, D. R. Lee, and T. H. Hansen. 1991. The specific binding of peptide ligand to Ld class I major histocompatibility complex molecules determines their antigenic structure. J Exp Med 173: 449-459, 1991.
55. Smith, J. D., et al., J. Exp. Med. 178: 2035-2046, 1993.
56. Myers, N. B., M. R. Harris, J. M Connolly, L. Lybarger, Y. Y. Yu, and T. H. Hansen. 2000. J Immunol 165: 5656-5663, 2000.
57. Sykulev, Y., A. Brunmark, M. Jackson, R. I. Cohen, P. A. Peterson, and H. N. Eisen. 1994, Kinetics and affinity of reactions between an antigen-specific T cell receptor and peptide-MHC complexes. Immunity 1:15.
58. Sykulev, Y., R. J. Cohen, and H. N. Eisen. 1995. The law of mass action governs antigen-stimulated cytolytic activity of CD8+ cytotoxic T lymphocytes. Proc Natl Acad Sci USA 92:11990.

59. Ljunggren, H. G., N. J. Stam, C. Ohlen, J. J. Neefjes, P. Hoglund, M. T. Heemels, J. Bastin, T. N. Schumacher, A. Townsend, K. Karre, and et al. 1990. Empty MHC class I molecules come out in the cold. Nature 346:476.
60. Kageyama, S., T. J. Tsomides, Y. Sykulev, and H. N. Eisen. 1995. Variations in the number of peptide-MHC class I complexes required to activate cytotoxic T cell responses. J Immunol 154:567.
61. Ignatowicz, L., J. Kappler, and P. Marrack. 1996. The repertoire of T cells shaped by a single MHC/peptide ligand. Cell 84:521.
62. Barton, G. M., and A. Y. Rudensky. 1999. Requirement for diverse, low-abundance peptides in positive selection of T cells. Science 283:67.
63. Huseby, E. S., J. White, F. Crawford, T. Vass, D. Becker, C. Pinilla, P. Marrack, and J. W. Kappler. 2005. How the T cell repertoire becomes peptide and MHC specific. Cell 122:247.
64. Peng, S., H. Ji, C. Trimble, L. He, Y. C. Tsai, J. Yeatermeyer, D. A, Boyd, C. F. Hung, and T. C. Wu. 2004. Development of a DNA vaccine targeting human papillomavirus type 16oncoprotein E6. J Virol 78:8468.
65. Altman, J. D. 2004. Flow cytometry applications of MHC tetramers. Methods Cell Biol 75:433.
66. Ogg, G. S., P. R. Dunbar, V. Cerundolo, A. I. McMichael, N. R. Lemoine, and P. Savage. 2000. Sensitization of tumour cells to lysis by virus-specific CTL using antibody-targeted MHC class I/peptide complexes. Br J Cancer 82:1058.
67. Robert, B., P. Guillaume, I. Luescher, P. Romero, and J. P. Mach. 2000. Antibody-conjugated MHC class I tetramers can target tumor cells for specific lysis by T lymphocytes. Eur Immunol 30:3165
68. Lev, A., R. Noy, K. Oved, H. Novak, D. Segal, P. Walden, D. Zehn, and Y. Reiter. 2004. Tumor-specific Ab-mediated targeting of MHC-peptide complexes induces regression of human tumor xenografts in vivo. Proc Natl Acad Sci USA 101; 9051.
69. Townsend, A., and Bodmer, H. (1989) Annu Rev Immunol 7, 601-624.
70. Kourilsky, P., and Claverie, J. M. (1989) Adv Immunol 45, 107-193.
71. Bjorkman, P. J., and Parham, P. (1990) Annu Rev Biochem 59, 253-288.
72. Tsomides, T. J., and Eisen, H. N. (1991) J Biol Chem 266, 3357-3360.
73. Jones, E. Y. (1997) Curr Opin Immunol 9, 75-79.
74. Madden, D. R. (1995) Annu Rev Immunol 13, 587-622.
75. Wilson, I. A., and Fremont, D. H. (1993) Semin Immunol 5, 75-80,
76. Natarajan, K., Li, H., Mariuzza, R. A., and Margulies, D. H. (1999) Rev Immunogenet 1, 32-46.
77. Young, A. C., Nathenson, S. G., and Sacchettini, J. C. (1995) Faseb J 9, 26-36.
78. Lipford, G. B., Bauer, S., Wagner, H., and Heeg, K. (1995) Vaccine. 13, 313-320.
79. Eisenlohr, L. C, Yewdell, J. W., and Bennink, J. R. (1992) J Exp Med. 175, 481-487.
80. Del Val, M., Schlicht, H. J., Ruppert, T., Reddehase, M. J., and Koszinowski, U. H. (1991) Cell. 66, 1145-1153.
81. Heemels, M. T., and Ploegh, H. (1995) Annu Rev Biochem. 64, 463-491.
82. Deng, Y., Yewdell, J. W., Eisenlohr, L. C., and Bennink, J. R. (1997) J Immunol. 158, 1507-1515.
83. Chen, Y., Webster, R. G., and Woodland, D. L. (1998) J Immunol. 160, 2425-2432.
84. Tsai, V., Southwood, S., Sidney, J., Sakaguchi, K., Kawakami, Y., Appella, E., Sette, A., and Celis, E. (1997) J Immunol. 158, 1796-1802.
85. Meier, A., Reker, S., Svane, I. M., Holten-Andersen, L., Becker, J. C., Sondergaard, I., Andersen, M. H., and Thor Straten, P. (2005) Cancer Immunol Immunother. 54, 219-228. Epub 2004 October 2002.
86. Yee, C, Savage, P. A., Lee, P. P., Davis, M. M., and Greenberg, P. D. (1999) J Immunol. 162, 2227-2234.
87. Romero, P., Dunbar, P. R., Valmori, D., Pittet, M, Ogg, G. S., Rimoldi, D., Chen, J. L., Lienard, D., Cerottini, J. C., and Cerundolo, V. (1998) J Exp Med. 188, 1641-1650.
88. O'Herrin, S. M, Slansky, J. E., Tang, Q., Markiewicz, M. A., Gajewski, T. F., Pardoll, D. M., Schneck, J. P., and Bluestone, J. A. (2001) J Immunol. 167, 2555-2560.
89. Greten, T. F., Slansky, J. E., Kubota, R., Soldan, S. S., Jaffee, E. M., Leist, T. P., Pardoll, D, M., Jacobson, S., and Schneck, J. P. (1998) Proc Natl Acad Sci USA. 95, 7568-7573.
90. Kawakami, Y., Eliyahu, S., Jennings, C, Sakaguchi, K., Kang, X., Southwood, S., Robbins, P. F., Sette, A., Appella, E., and Rosenberg, S. A. (1995) J Immunol. 154, 3961-3968.
91. Mitaksov, V., and Fremont, D. H. (2006) J Biol Chem. 281, 10618-10625. Epub 12006 February 10610.
92. (1994) Acta Crystallogr D Biol Crystallogr. 50, 760-763.
93. Brunger, A. T., Adams, P. D., Gore, G. M., DeLano, W. L., Gros, P., Grosse-Kunstleve, R. W., Jiang, J. S., Kuszewski, J., Nilges, M., Pannu, N. S., Read, R. J., Rice, L. M., Simonson, T., and Warren, G. L. (1998) Acta Crystallogr D Biol Crystallogr. 54, 905-921.
94. Carson, M. (1987) J Mol Graphics 5, 103-106
95. McDonald, I. K., and Thornton, J. M. (1994) J Mol Biol 238, 777-793
96. Fremont, D. R., Stura, E. A., Matsumura, M., Peterson, P. A., and Wilson, I. A. (1995) Proc Natl Acad Sci USA. 92, 2479-2483.
97. Connolly, M. L. (1983) Science. 221, 709-713.
98. Collins, E. J., Garboczi, D. N., and Wiley, D. C. (1994) Nature. 371, 626-629.
99. Matsumura, M., Fremont, D. H., Peterson, P. A., and Wilson, I. A. (1992) Science. 257, 927-934.
100. Miley, M. J., Messaoudi, I., Metzner, B. M., Wu, Y., Nikolich-Zugich, J., and Fremont, D. H. (2004) J Exp Med. 200, 1445-1454. Epub 2004 November 1422.
101. Pope, C., Kim, S. K., Marzo, A., Masopust, D., Williams, K., Jiang, J., Shen, H., and Lefrancois, L. (2001) J Immunol. 166, 3402-3409.
102. Greten, T. F., Korangy, F., Neumann, G., Wedemeyer, H., Schlote, K., Heller, A., Scheffer, S., Pardoll, D. M., Garbe, A. T, Schneck, J. P., and Manns, M. P. (2002) J Immunol Methods. 271, 125-135.
103. Oved, K., Lev, A., Noy, R., Segal, D., and Reiter, Y. (2005) Cancer Immunol Immunother. 54, 867-879. 2005.
104. Hirel, P. H., Schmitter, M. J., Dessen, P., Fayat, G, and Blanquet, S. (1989) Proc Natl Acad Sci USA. 86, 8247-8251.
105. Lathrop, B. K., Burack, W. R., Biltonen, R. L., and Rule, G. S. (1992) Protein Expr Purif. 3, 512-517.
106. Parkhurst, M. R. et al., J. Immunol. 157, 2539-2548 (1996).
107. Kannagi, M. et al., J. Virol. 66, 2928-2933 (1992).
108. Huet, S. et al., Int'l. Immunol. 2, 311-316 (1990).
109. Brodsky, F. M., et al., Immunol. Rev. 47, 3-61, 1979.
110. Ellis, S. A., et al. Hum. Immunol. 5, 49-59, 1982.
111. Stam, N. J. et al., Int'l. Immunol 2, 113-125, 1990.

112. Carreno, B. M., et al., Proc. Nat'l Acad. Sci. USA 87, 3420-3424, 1990.
113. Linette, G. P., et al., Clin. Cancer Res. 11, 7692-7699, 2005.
114. Kawakami, Y., et al., Proc. Nat'l. Acad. Sci. USA 91, 6458-6462, 1994.
115. Poiesz, B. J., et al., Proc. Nat'l. Acad. Sci. USA 77, 7415-7419, 1980.
116. Granfors, K., et al., Arthritis Rheum. 46, 606-613, 2002.
117. Stevenson, F. K. et al., Proc Natl Acad Sci USA 101 Suppl 2, 14646-14652, 2004.
118. Donnelly, F. K., et al., J. Immunol. 175, 633-639, 2005.
119. Truscott, S. M. Dissertation, 1-191. Washington University in St. Louis, 2007.
120. Parker, K. C., et al., J. Immunol. 152, 163-175, 1994.

All publications, patents, patent applications and other references cited in this application are herein incorporated by reference in their entirety as if each individual publication, patent, patent application or other reference were specifically and individually indicated to be incorporated by reference.

TABLE 3

Data collection, refinement, and structure comparisons statistics

|  | $SCT^{WT}$ | $SCT^{Y84A}$ | $SCT^{Y84C-PBL2C}$ |
|---|---|---|---|
| Data collection | | | |
| Space group | $P2_1$ | $P2_1$ | $P2_1$ |
| Cell dimensions | | | |
| a, b, c (Å) | 66.2, 89.6, 88.5 | 66.1, 89.3, 88.5 | 66.6, 89.1, 88.6 |
| $\alpha = \gamma = 90, \beta$ (°) | 111.0 | 111.0 | 110.9 |
| No. of Molecules Per ASU | | | |
| Resolution (Å) | 20.0-2.00 (2.07-2.00)$^b$ | 20-2.00 (2.07-2.0) | 20-1.80 (1.86-1.80) |
| $R_{sym}{}^a$ | 7.5 (47.3) | 9.3 (53.5) | 5.8 (53.3) |
| I/σI | 23.4 (3.80) | 17.7 (3.07) | 30.3 (3.39) |
| Completeness (%) | 98.4 (97.2) | 99.9 (99.7) | 99.9 (100) |
| Redundancy | 6.8 | 6.3 | 6.8 |
| Refinement | | | |
| Resolution (Å) | 20.0-2.00 (2.07-2.00) | 20.0-2.00 (2.07-2.00) | 20.0-1.80 (1.86-1.80) |
| No. reflections | 64087 (5963) | 64727 (6111) | 89351 (8411) |
| $R_{work}/R_{free}{}^b$ | 21.5(34.1)/25.3(35.1) | 21.0(30.8)/25.2(34.7) | 20.8(33.3)/23.9(34.2) |
| No. atoms | | | |
| Protein | 6396 | 6382 | 6388 |
| Water | 639 | 700 | 755 |
| β-factors (Å$^2$) | | | |
| Protein | 35.8 | 30.2 | 34.9 |
| Water | 44.4 | 39.8 | 45.2 |
| R.m.s.d. from ideal values | | | |
| Bond lengths (Å) | 0.0088 | 0.0086 | 0.0093 |
| Bond Angles (°) | 1.56 | 1.55 | 1.678 |
| Structural Comparisons$^d$ | | | |
| R.m.s.d. (Å) from 1VAC(c2) | | | |
| $K^b$-Ova/HC/α1α2/β$_2$m/Ova | 1.96/1.15/0.61/0.98/0.52 | 2.15/1.34/0.78/0.83/0.48 | 2.15/1.37/0.81/0.97/0.51 |
| R.m.s.d. (Å) from 1TGM(p2.) | | | |
| $K^b$/HC/α1α2/β$_2$m | 0.79/0.72/0.55/0.88 | 0.64/0.68/0.46/0.45 | 0.72/0.66/0.55/0.82 |

$^a$Statistics as defined in SCALEPACK
$^b$Values in parentheses are for data in the highest resolution shell
$^c$Statistics as defined in CNS
$^d$R.m.s.d. values calculated based on an alignment of main-chain atoms of the indicated complexes or domains using Lsqkab in CCP4

TABLE 4

Applications of HLA complexes constructed as SCTs

| HLA allele | Peptide | Origin | Sequence | Mammalian cell surface expression | Immune receptor engagement | DNA vaccine | Recombinant multimers for flow cytometry | References |
|---|---|---|---|---|---|---|---|---|
| A*0201 | G280-9V | melanoma | YLEPGPVTV (SEQ ID NO: 5) | Yes (shown here) | TCR | | • | * Oved, K., et al. |
| A*0201 | TAX | HTLV | LLFGYPVYV (SEQ ID NO: 6) | Yes (shown here) | TCR | | • | * Greten, et al. |
| A*0201 | M1 | Influenza A | GILGFVFTL (SEQ ID NO: 3) | Yes | TCR | | | Greten, et al. |

TABLE 4-continued

Applications of HLA complexes constructed as SCTs

| HLA allele | Peptide | Origin | Sequence | Mammalian cell surface expression | Immune receptor engagement | DNA vaccine | Recombinant multimers for flow cytometry | References |
|---|---|---|---|---|---|---|---|---|
| A*0201 | pp65 | CMV | NLVPMVATV (SEQ ID NO: 1) | Yes | TCR | | • | Greten, et al. |
| A*0201 | G209-2M | Melanoma | IMDQVPFSV (SEQ ID NO: 4) | n.d. | TCR | | • | Oved, K., et al. |
| A*0201 | GLC$_{280-288}$ | EBV | GLCTLVAML (SEQ ID NO: 2) | n.d. | TCR | | • | Oved, K., et al. |
| A*0201 | MAM-A2.1 | Mammaglobin (breast cancer) | LIYDSSLCDL (SEQ ID NO: 7) | n.s. | TCR | • | | Jaramillo, et al. |
| A*0201 | HBcAg$_{18-27}$ HBcAg$_{107-115}$ | Hepatitis B virus | FLPSDFFPSV (SEQ ID NO: 8) CLTFGRETV (SEQ ID NO: 9) | Yes | TCR | • | | Zhang, et al. |
| A*0201 | HIVgag | HIV | SLYNTVATL (SEQ ID NO: 10) | Yes | TCR | • | | Zhang, et al. |
| A*0201 | Hmeso$_{540-549}$ | Mesothelin (ovarian cancer) | KLLGPHVEGL (SEQ ID NO: 11) | n.s. | TCR | • | | Hung, et al. |
| B*2705 | NP$_{383-391}$ | Influenza A | SRYWAIRTR (SEQ ID NO: 12) | Yes (shown here) | TCR | • | | * |
| HLA-E | Sequence found within the signal peptide of many HLA-C alleles | | VMAPRTLIL (SEQ ID NO: 12) | Yes | NK | | | Crew, et al. |

What is claimed is:

1. A disulfide trap comprising, in amino terminal-to-carboxy terminal order, an MHC class I ligand peptide, a first linker, said first linker comprising a first cysteine, a β2-microglobulin, a second linker, and an MHC class I heavy chain sequence comprising a second cysteine, wherein said second cysteine is a substitution of an amino acid of the MHC class I heavy chain selected from the group consisting of T80C, Y84C and N86C, and wherein the first cysteine and the second cysteine comprise a disulfide bridge.

2. A disulfide trap in accordance with claim 1, wherein the MHC class I ligand peptide comprises an MHC class I antigen peptide.

3. A disulfide trap in accordance with claim 2, wherein the MHC class I antigen peptide is an MHC class I self peptide.

4. A disulfide trap in accordance with claim 2, wherein the MHC class I antigen peptide is an MHC class I tumor peptide.

5. A disulfide trap in accordance with claim 1, wherein the MHC class I heavy chain sequence is a human MHC class I heavy chain sequence.

6. A disulfide trap in accordance with claim 1, wherein the MHC class I heavy chain sequence is a murine MHC class I heavy chain sequence.

7. A disulfide trap in accordance with claim 1, wherein the MHC class I ligand peptide comprises from about 8 amino acids up to about 13 contiguous amino acid residues.

8. A disulfide trap in accordance with claim 1, wherein the MHC class I ligand peptide comprises 9 contiguous amino acids.

9. A disulfide trap in accordance with claim 5, wherein the human MHC class I heavy chain sequence is selected from the group consisting of an HLA-A MHC class I heavy chain sequence and an HLA-B MHC class I heavy chain sequence.

10. A disulfide trap in accordance with claim 5, wherein the human MHC class I heavy chain sequence is an HLA heavy chain sequence selected from the group consisting of an HLA-A, HLA-B and HLA-C heavy chain sequence.

11. A disulfide trap in accordance with claim 1, wherein the MHC class I heavy chain sequence is a murine heavy chain sequence selected from the group consisting of an MHC-K, MHC-D and MHC-L murine heavy chain class I sequence.

12. A disulfide trap in accordance with claim 1, wherein the first cysteine is the first, second or third amino acid of the linker.

13. A disulfide trap in accordance with claim 1, wherein the second linker comprises at least about 15 amino acids up to 20 amino acids, and wherein at least about 80 percent of the amino acids comprising the second linker are glycines.

14. A disulfide trap in accordance with claim 1, further comprising a leader peptide.

15. An MHC/peptide multimer comprising a disulfide trap of claim 1.

16. An MHC/peptide multimer in accordance with claim 15, further comprising a label.

17. An MHC/peptide multimer in accordance with claim 16, wherein the label is selected from the group consisting of a hapten, a radioisotope and a fluorophore.

18. An MHC/peptide multimer in accordance with claim 17, wherein the radioisotope is selected from the group consisting of $H^3$, $P^{32}$, $P^{33}$, $S^{35}$, $C^{14}$, $I^{125}$ and $I^{131}$.

19. An MHC/peptide multimer in accordance with claim 15, wherein the multimer is a tetramer.

20. A disulfide trap single chain trimer in accordance with claim 1, wherein the first linker comprises at least 1 up to 15 amino acids and comprises the first cysteine, and the second linker comprises at least 15 amino acids up to 20 amino acids, and wherein at least 80 percent of the amino acids comprising the second linker are glycines.

21. A disulfide trap in accordance with claim 20, wherein the first cysteine is the first, second or third amino acid of the linker.

22. A disulfide trap in accordance with claim 1, wherein the MHC class I heavy chain comprises a non-covalent binding site for the MHC ligand peptide.

* * * * *